United States Patent [19]

Heym et al.

[11] Patent Number: 6,124,098

[45] Date of Patent: Sep. 26, 2000

[54] RAPID DETECTION OF ANTIBIOTIC RESISTANCE IN MYCOBACTERIUM TUBERCULOSIS

[75] Inventors: Beate Heym, Ville d'Avray; Stewart Cole, Clamart, both of France; Douglas Young, Ruislip; Ying Zhang, London, both of United Kingdom; Nadine Honore, Colombes, France; Amalio Telenti, Gerzensee; Thomas Bodmer, Ersigen, both of Switzerland

[73] Assignees: Institut Pasteur, Paris, France; Medical Research Council, London, United Kingdom; Assistance Publique; Universite Pierre et Marie Curie (Paris VI), both of Paris, France; Universite de Berne, Berne, Switzerland

[21] Appl. No.: 09/082,614

[22] Filed: May 20, 1998

Related U.S. Application Data

[63] Continuation of application No. 08/313,175, filed as application No. PCT/EP01/01063, Apr. 30, 1993, Pat. No. 5,851,763, which is a continuation of application No. 07/929,206, Aug. 14, 1992, Pat. No. 5,633,131, which is a continuation-in-part of application No. 07/875,940, Apr. 30, 1992, abandoned.

[30] Foreign Application Priority Data

Sep. 17, 1992 [FR] France ................................ 92/11098
Apr. 16, 1993 [FR] France ................................ 93/04545

[51] Int. Cl.[7] .............................. C12Q 1/68; C12P 19/34; G01N 33/509; C07H 21/04
[52] U.S. Cl. ......................... 435/6; 435/7.32; 435/91.1; 435/91.2; 536/23.1; 536/23.2
[58] Field of Search .............................. 435/6, 7.32, 91.1, 435/91.2; 536/23.1, 23.2

[56] References Cited

U.S. PATENT DOCUMENTS 4,683,195  7/1987  Mullis et al. ................................ 435/6
5,633,131  5/1997  Heym et al. .
5,871,912  2/1999  Heym et al. ................................ 435/6

FOREIGN PATENT DOCUMENTS 0 223 156      5/1987   European Pat. Off. .
WO9104036      4/1991   WIPO .
WO 9 106 674   5/1991   WIPO .
WO 95 33 074   12/1995  WIPO .

OTHER PUBLICATIONS

Heym et al. (1992), Research in Microbiology, vol. 143, No. 7, pp. 721–730.

Jin et al. (1988), Journal of Molecular Biology, vol. 202, No. 1, pp. 45–58.

Sriprakash et al. (1970), The Journal of General Microbiology, vol. 60, No. 1, pp. 125–132.

Telenti et al. (1993), The Lancet, vol. 341, No. 8846, pp. 647–650.

Zhang et al. (1992), Nature, vol. 358, No. 6387, pp. 591–593.

Prescott et al Microbiology pp. 253–256, 1990.

CDC MMWP vol. 39 No. 22 pp. 369–372, 1990.

Devi et al Biochem J. vol. 149 pp. 187–197, 1975.

*Primary Examiner*—Kenneth R. Horlick
*Assistant Examiner*—Jeffrey Siew
*Attorney, Agent, or Firm*—Finnegan, Henderson, Farabow, Garrett & Dunner, L.L.P.

[57] ABSTRACT

A nucleotide sequence encoding a katG/lacZ fusion protein is useful for assaying the enzymatic activity of the katG gene product. A process of selecting a compound that is toxic against an isoniazid-resistant mycobaterial strain comprises incubating a catalase peroxidase enzyme with an isoniazid to produce a compound that restores isoniazid susceptability to the isoniazid-resistant mycobaterial strain.

9 Claims, 26 Drawing Sheets

1  2  3  4  5          1  2  3  4  5

```
<---------- lacZ'------------>
 M  T  M  I  T  P  S  L  H  A  C  R  S  T  L  E  D  P  H  P  T  L  R
ATGACCATGATTACGCCAAGCTTGCATGCCTGCAGGTCGACTCTAGAGGATCCCCATCCGACACTTCGCG
         10        20        30        40        50        60        70 katG------>
 M  S  T  S  D  D  -  -  I  H  N  T  T  A  T  G  K  C  P  F  H  Q  G
 *  :        *  :              *  :     *  :  :     :        :
 M  P  E  Q  H  P  P  I  T  E  T  T  T  G  A  A  S  N  G  C  P  V  V
GTGCCCGAGCAACACCCCACCATTACAGAGAAACCACCGGAGCCGCTAGCAACGGCTGTCCCGTCGTGG
        130       140       150       160       170       180       190

N  Q  L  R  V  D  L  L  N  Q  H  S  N  R  S  N  P  L  G  E  D  F  D
 *  :        *  :  :        *  :  :     *  :  :     *  :  :     *  :  *
 N  R  L  N  L  K  V  L  H  Q  N  P  A  V  A  D  P  M  G  A  A  F  D
AACCGGCTCAATCTGAAGGTACTGCACCAAAACCCGGCTGTCGCTGACCCGATGGGTGCGGCGTTCGACT
        250       260       270       280       290       300       310

FIG. 2C(I)
```

```
D   H   I   R   D   H   S   P   I   T   P   T   P   G   R   N   A
ATCACATCCGTGATCACAGCCCGATAACACCAACTCCTGGAAGGAATGCT              E.coli
            80              90              100             110             120

G   H   D   Q   S   A   G   A   G   T   T   T   T   R   D   W   W   P       E.coli
*   :           *       :           *   :           *       *   *   *       
G   H   M   K   Y   P   V   E   G   G   G   N   Q   D   W   W   P       M.tub
GTCATATGAAATACCCCGTCGAGGGCGGAAACCAGGACTGGTGGCCC
            200             210             220             230             240

Y   R   K   E   F   S   K   L   D   Y   Y   G   L   K   K   D   L       E.coli (SEQ ID NO:44)
*       :       :   *   :               :   :       *   :   :       
Y   A   A   E   V   A   T   S   R   L   D   A   L   T   R   D   I       M.tub (SEQ ID NO:43)
ATGCCGCGGAGGTCGCGACCAGTCGACTTGACGCCCTGACGCGGGACATC                         M.tub (SEQ ID NO:42)
                                                                           E.coli (SEQ ID NO:43)... 
            320             330             340             350             360
```

FIG. 2C(2)

| | | | | |
|---|---|---|---|---|
| GGTACCGTGA | GGGCGATGGGT | GGCCCGGGGC | CCGGCTGTCT | GGTAAGCGCCG | GCCGCAAAAC | 60 |
| AGCTGTACTC | TCGAATCCCA | GTTAGTAACA | ATGTGCTATG | GAATCTCCAA | TGACGAGCAC | 120 |
| ACTTCACCGA | ACCCCATTAG | CCACCGCGGG | GCTGGCGCTC | GTAGTGGCGC | TGGGTGGCTG | 180 |
| CGGGGGCGGG | GGCGGTGACA | GTCGAGAGAC | ACCGCCATAC | GTGCCGAAAG | CGACGACCGT | 240 |
| CGACGCAACA | ACGCCGGGCG | CGGCCGCCGA | GCCACTGACG | ATCGCCAGTC | CCATGTTCGC | 300 |
| CGACGGCGCC | CCGATCCCGG | TGCAATTCAG | CTGCAAGGGG | GCCAACGTGG | CCGCCACCGT | 360 |
| TGACGTGGTC | GTCGCCCGCG | GCGAGCGAAC | TGGCACTCGT | CGTCGATGAC | CCCGACGCGG | 420 |
| TCGGCGGACT | GTACGTGCAC | TGGATCGTGA | CCGGAATCGC | CCCTGGCTCT | GGCAGCACGG | 480 |
| CGGATGGTCA | GACTCCTGCT | GGTGGGCACA | GCGTGCCGAA | TTCTGGTGGT | CGGCAAGGAT | 540 |
| ACTTCGGTCC | ATGCCCGCCG | GCGGGCACCG | GGACACACCA | CTACCGGTTT | ACCCTCTACC | 600 |
| ACCTTCCTGT | CGGCCTCCAG | CTGCCACCGG | AGGCCACGGG | AGTCCAAGCG | GCACAGGCGA | 660 |
| TAGCACAGGC | CGCCAGCGAC | AGGCCCGCGT | CGTCGGCACA | TTCGAAGGCT | GACGCCGCGG | 720 |
| CATCCCTGGC | GAGGTGGTCG | AAACCCTGGC | TTCTCCAATT | GCGCCTGGCG | ACAATGATCA | 780 |
| ATATGGAATC | GACAGTGGCG | CACGCCATTC | ACCGGTTCGC | ACTGGCCATC | TTGGGCTGG | 840 |
| CGCTCCCCGT | GGGCGCTAGTT | GCCTACGGTG | GCAACGGTGA | CAGTCGAAAG | GCGGCGGCCG | 900 |
| TGGCGCCGAA | AGCAGCAGCG | CTCGGTCGGA | GTATGCCCGA | CCCGGAACAG | GGCGATGTAC | 960 |
| TGACAATCAG | CAGTCCGGCA | TTCGCGGCC | TGGTCGGGCG | GTGCGCCGAT | TACACCTGCA | 1020 |
| AAGGAGCCAA | TATCGCGGCC | TCCGTTGACC | TGGTCGGGCG | CCCGGAACAG | CGCACTCGTT | 1080 |
| GTCGATGATC | CGGACCACCT | CGGAACCTT | ACGTCCATTG | GATCGTGATC | GGATCGCCC | 1140 |
| CTGGTGCTGG | CAGCAGCCGA | TGGTGAGACT | CCCGGTGGCG | GAATCAGCCT | GCCGAACTCC | 1200 |
| AGCGGTCAGC | CCGCATACAC | CGGCCCCTGC | CGGCCGGGAC | GCACCGGCGG | ACACCACTAC | 1260 |

FIG. 6A-1

```
CGGTTTACCC TCTACCACCT TCCTGCCGTG CCTCCACTCG CGGGACTGGC TGGGACACAA    1320
GCGGCGGGG  TGATCGCGCA GGCCGCCACC ATGCAGGCCC GGCTCATCCG AACATACGAA    1380
GGCTGATCCA CCCGCCATCC CACGATCCAG CGGCCCCGGG CGATCGGGTC CTAGCAGACG    1440
CCTGTCACGC TAGCCAAAGT CTTGACTGAT TCCAGAAAAG GGAGTCATAT TGTCTAGTGT    1500
GTCCTCTATA CCGGACTACG CCGAACAGCT CCGGACGGCC GACCTGCCGC TGACCCGACC    1560
GCGCGTCGCC GTCCTGGAAG CAGTGAATGC GCATCCACAC GCCGACACGG AAACGATTTT    1620
CGGTGCCGTG CGTTTTGCGC TGCCCGACGT ATCCGGCAAG CCGTGTACGA CGTGCTGCAT    1680
GCCCTGACCG CCGCGGGCTT GGTGCGAAAG ATCCAACCCT CGGGCTCCGT CGCGCGCTAC    1740
GAGTCCAGGG TCGGCGACAA CCACCATCAC ATCGTCTGCC GGTCTTGCGG GGTTATCGCC    1800
GATGTCGACT GTGCTGTTGG CGAGGCACCC TGTCTGACGG CCTCGACCA  TAACGGCTTC    1860
CTGTTGGACG AGGCGGAGGT CATCTACTGG GGTCTATGTC CTGATTGTTC GATATCCGAC    1920
ACTTCGCGAT CACATCCGTG ATCACAGCCC GATAACACCA ACTCCTGGAA GGAATGCTGT    1980
GCCCGAGCAA CACCCACCCA TTACAGAAAC CACCACCGGA GCCGCTAGCA ACGGCTGTCC    2040
CGTCGTGGGT CATATGAAAT ACCCCGTCGA GGGCGGCGAA AACCAGGACT GGTGGCCCAA    2100
CCGGCTCAAT CTGAAGGTAC TGCACCAAAA CCCGGCCCGTC GCTGACCCGA TGGGTGCGGC    2160
GTTCGACTAT GCCGCGGAGG TCGCGGACCAG GCCCTTGAC  GCCCTGACGC GGGACATCGA    2220
GGAAGTGATG ACCACCTCGC AGCCGTGGTG GCCGCCGCAC TACGGCCACT ACGGGCCGCT    2280
GTTTATCCGG ATGGCGTGGC ACGCCTGCCGG CACCTACCGC ATCCACGACG GCCGGGGCGG    2340
CGCCGGGGC  GGCATGCAGC GGTTCGCGCC GCTTAACAGC TGGCCCGACA ACGCCAGCTT    2400
GGACAAGGCG CGCCGGCTGC TGTGGCCGGT CAAGAAGAAG TACGGCAAGA AGCTCTCATG    2460
GGCGGACCTG ATTGTTTTCG CCGGCAACCG CTGCGCTCGG AATCGATGGG CTTCAAGACG    2520
TTCGGGTTCG GCTTCGGGCG TCGACCAGTG GGAGACCGAT GAGGTCTATT GGGGCAAGGA    2580
```

FIG. 6A-2

| | | | | | |
|---|---|---|---|---|---|
|AGCCACCTGG|CTCGGCGATG|ACGGTTACAG|CGTAAGCCAT|CTGGAGAACC|CGCTGGCCGC|2640|
|GGTGCAGATG|GGGCTGATCT|ACGTGAACCC|GGAGGCGCCG|AACGGCAACC|CGGACCCCAT|2700|
|GGCCGCGGCG|GTCGACATTC|GCGAGACGTT|TCGGCGCATG|GCCATGAACG|ACGTCGAAAC|2760|
|AGCGGCGCTG|ATCGTCGGCG|GTCACACTTT|CGGTAAGACC|CATGGCGCCG|GCCCGGCCGA|2820|
|TCTGGTCGGC|CCCGAACCCG|AGCCTGCTCC|GCTGGAGCAG|ATGGGCTTGG|GCTGGAAGAG|2880|
|CTCGTATGGC|ACCGGAACCG|GTAAGGACGC|GATCACCAGC|GGCATCGAGG|TCGTATGGAC|2940|
|GAACACCCCG|ACGAAATGGG|ACAACAGTTT|CCTCGAGATC|CTGTACGGCT|ACGAGTGGGA|3000|
|GCTGACGAAG|AGCCCTGCTG|GCGCTTGGCA|ATACACCGCC|AAGGACGGCG|CCGGTGCCGG|3060|
|CACCATCCCG|GACCCCGTTCG|GCGGGCCAGG|GCGCTCCCCG|ACGATGCTGG|CCACTGACCT|3120|
|CTCGCTGCGG|GTGGATCCGA|TCTATGAGCG|GATCACGCGT|CGCTGGCTGG|AACACCCCGA|3180|
|GGAATTGGCC|GACGAGTTCC|GCAAGGCCTG|GTACAAGCTG|ATCCACCGAG|ACATGGGTCC|3240|
|CGTTGCGAGA|TACCTTGGGC|CGCTGGTCCC|CAAGCAGACC|CTGCTGTGGC|AGGATCCGGT|3300|
|CCCTGCGGTC|AGCACGACCT|CGTCGGCGAA|GCAGATTGCC|AGCCTTAAGA|GCCAGATCCG|3360|
|GGCATCGGGA|TTGACTGTCT|CACAGCTAGT|TTCGACCGCA|TGGGCGGCGG|CGTCGTCGTT|3420|
|CCGTGGTAGC|GACAAGCGCG|GCGGCGCCAA|CGGTGGTCGC|ATCCGCCTGC|AGCCACAAGT|3480|
|CGGGTGGGAG|GTCAACGACC|CCGACGGATC|TGCCGCAAGGT|CATTCCGCACC|CTGAAGAGAT|3540|
|CCAGGAGTCA|TTCACTCGGC|GCGGAACAT|CAAAGTGTCC|TTCGCCGACC|TCGTCGTGCT|3600|
|CGGTGGCTGT|GCGCCACTAG|AGAAAGCAGC|AAAGGCGGCT|GGCCACAACA|TCACGGTGCC|3660|
|CTTCACCCCG|GGCCCGCACG|ATGCGTCGCA|GGAACAAACC|GACGTGGAAT|CCTTTGCCGT|3720|
|GCTGGAGCCC|AAGGCAGATG|GCTTCCGAAA|CTACCTCGGA|AAGGGCAACC|GTTGCCGGCC|3780|
|GAGTACATCG|CTGCTCGACA|AGGCGAACCT|GCTTACGCTC|AGTGCCCCTG|AGATGACGGT|3840|
|GCTGGTAGGT|GGCCTGCCGCG|TCCTCGGCCG|AAACTACAAG|CGCTTACCCGC|TGGGCGTGTT|3900|

FIG. 6A-3

```
CACCGAGGCC  TCCGAGTCAC  TGACCAACGA  CTTCTTCGTG  AACCTGCTCG  ACATGGGTAT   3960
CACCTGGGAG  CCCTCGCCAG  CAGATGACGG  GACCTACCAG  GGCAAGGATG  GCAGTGGCAA   4020
GGTGAAGTGG  ACCGGCAGCC  GCGTGGACCT  GGTCTTCGGG  TCCAACTCGG  AGTTGCGGGC   4080
GCTTGTCGAG  GTCTATGCGC  CGATGACGCG  GCAGGCGAAG  TTCGTGACAG  GATTCGTCGC   4140
TGCGTGGGAC  AAGGTGATGA  ACCTCGACAG  GTTCGACGTG  CGCTGATTCG  GGTTGATCGG   4200
CCCTGCCCGC  CGATCAACCA  CAACCCGCCG  CAGCACCCCG  CGAGCTGACC  GGCTCGCGGG   4260
GTGCTGGTGT  TTGCCCGGCG  CGATTTGTCA  GACCCCGCGT  GCATGGTGGT  CGCACGGACG   4320
CACGAGACGG  GGATGACGAG  ACGGGGATGA  GGAGAAAGGG  CGCCGAAATG  TGCTGGATGT   4380
GCGATCACCC  GGAAGCCACC  GCCGAGGAGT  ACCTCGACGA  GGTGTACGGG  ATAATGCTCA   4440
TGCATGGCTG  GGCGGTACAG  CACGTGGAGT  GCGAGCGACG  GCCATTTGCC  TACACGGTTG   4500
GTCTAACCCG  GCGCGGCTTG  CCCGAACTGG  TGGTGACTGG  CCTCTCGCCA  CGACCGTGGGC  4560
AGCGGGTTGTT GAACATGCCG  TCGAGGGCTC  TGGTCGGGTGA  CTTGCTGACT  CCCGGTATGT   4620
AGACCACCCT  CAAAGCCGGC  CCTCTTGTCG  AAACGGTCCA  GGCTACACAT  CCGGACGCGC   4680
ATTTGTATTG  TGCGATCGCC  ATCTTTGCGC  ACAAGGTGAC  GGCCTTGCAG  TTGGTGTGGG   4740
CCGACCGCGT  GGTCGCTGGC  CGTGGGGCGGC  GGACTTCGAC  GAAGGTCGCG  GTACC (SEQ ID NO:45)  4795
```

```
      1241                  1251             1261         1271             1281          1291
      CAGCCTGCCG  AACTCCAGCG  GTCAGCCCGC  ATACACCGGC  CCCTGCCCGC  CGGCGGGCAC
      **********  ** ** ****  *** **  *    *** *****  ** ******  **********
      CAGCCGTGCCG AATTCTGGTG GTCGGGCAAGG ATACTTCGGT CCATGCCCGC CGGCGGGCAC
541                      561              571          581
1301                    1311             1321         1331             1341          1351
      CGGGACACAC  CACTACCGGT  TTACCCTCTA  CCACCTTCCT  GCCGTGCCTC  CA-CTCGC---
      **********  **********  **********  **********  * **  ****  ** **
      CGGGACACAC  CACTACCGGT  TTACCCTCTA  CCACCTTCCT  GTCGCGC-TC  CAGCT-GCCA
601                      611              621          631              641           651
1361                    1371             1381         1391             1401          1411
      ---GGGACTGG CT--GGGA-- CACAAGCGC  GCGGGTGATC  GCGCAGGCCG  CCACCATG-C
      ***          *          ****      ** ***      ***  ****   ***   *
      CCGGGA---G  CCACGGGAGT C-CAAGCGGC ACAGGCGGC   GCACAGGCCG  CCAGC---GAC
661                      681              691          701              711
1421                    1431             1441         1451             1461
      AGGCCCGGCT  CATCGGAACA  TACGAAAGGCT GATCCCACCCG CCATCC        (SEQ ID NO:46)
      **********  **********  ***
      AGGCCCGGGCT CGTCGGCACA                                       (SEQ ID NO:47)
721                      731              741          751              761
```

FIG. 6B-2

```
           1                                                                        70
MTKATG     MPEQHPPITE TTTGAASNGC PVVGHMKYPV EGGGNQDWP NRLNLKVLHQ NPAVADPMGA AFDYAAEVAT
ECKATG     ..MSTSDDIH NTTATGKCPF HQGGHDQSAG AGTTRDWWP NQLRVDLLNQ HSNRSNPLGE DFDYRKEF..
STKATG     ..MSTTDDTH NTLSTGKCPF HQGGHDRSAG AGTASRDWWP NQLRVDLLNQ HSNRSNPLGE DFDYRKEF..
BSPERA     ....MENQ   NRQNAAQCPF HESVTNQSS. NRTTNKDWP  NQLNLSILHQ HDRKTNPHDE EFNYAEEFQ.
 (CCP)                               ..TTPLHV ASVEKGRSYE DFQ......
CONSENSUS  --MST-DDTH NTT----KCPF HQGGHDQSAG AGTTNRDWP  NQL--DLLHQ HSNRSNPLGE DFDY-KEF--

71                                                                       140
MTKATG     SRLD...ALT RDIEEVMTTS QPWWPADYGH YGPLFIRMAW HAAGTYRIHD GRGGAGGGMQ RFAPLNSWPD
ECKATG     SKLDYY.GLK KDLKALLTES QPWWPADWGS YAGLFIRMAW HGAGTYRSID GRGGAGRGQQ RFAPLNSWPD
STKATG     SKLDYYSALK GDLKALLTDS QPWWPADWGS YVGLFIRMAW HGAGTYRSID GRGGAGRGQQ RFAPLNSWPD
BSPERA     .KLDYW.ALK EDLRKLMTES QDWWPADYGH YGPLFIRMAW HSAGTYRIGD GRGGASTGTQ RFAPLNSWPD
 (CCP)     .KVYNAIALK .......LRED DEY...DNYIG YGPVLVRLAM HISGTWDKHD NTGGSYGGTY RFKKEFNDPS
CONSENSUS  SKLDYY-ALK -DLKALLTES QPWWPADYG- YGPLFIRMAW HGAGTYR---D GRGGAG-G-Q RFAPLNSWPD
                                              R  W        H(108)

141                                                                      210
MTKATG     NASLDKARRL LWPVKKKYGK KISWADLIVF AGNRCARNRW ASRRSGSASG ....VDQWETD .EVYWGKEAT
ECKATG     NVSLDKARRL LWPIKQKYGQ KISWADLFIL AGNVALENSG FRTFGFGAGR ....EDVWEPD LDVNWGDEKA
STKATG     TVSLDKARRL LWPIKQKYGQ KISWADLFIL AGNVALENSG FRTFGFGAGR ....EDVWEPD LDVNWGDEKA
BSPERA     NANLDKARRC YGRSKRNTGT K.SLGPICSF WRAMSLLNRW VEKRLDSAAG PLTSGIRKKT FIGDRKKSGS
 (CCP)     NAGLQNGFKF LEPIHKEFP. WISSGDLFSL GGVTAVQEMQ GPKIPWRCGR VDTPEDTTPD ......NG
CONSENSUS  NASLDKARRL LWPIK-KYGQ KISWADLFIL AGNVALEN-- FR--GF-AGR --TEDVWEPD LDVNWG-EKA
                 R W             N(138)

211                                                                      280
MTKATG     WLGDDGYSVS DLENPLAAVQ MGLIYVNPEA PNGNPDPMAA AVDIRETFRR MAMNDVETAA LIVGGHTFGK
ECKATG     WLTHR.HPEA LAKAPLGATE MGLIYVNPEG PDHSGEPLSA AAAIRATFGN MGMNDEETVA LIAGGHTLGK
STKATG     WLTHR.HPEA LAKAPLGATE MDLIYVTPEG PNHSGEPLSA AAAIRATFGN MGMNDEETVA LIAGGHTLGK
BSPERA     PLNAIPVIAS SKTRSPRANG VNLRQPRRAG RQAGSKSRGI SA...ETFRR MGMNDEETVA LIAGGHTLGK
 (CCP)     RL....      LAKAPLGATE MGLIYVNPEG ..PDADKD AGYVRTFFQR LNMNDREVVA LM.GAHALGK
CONSENSUS  WLTHR-HPE- LAKAPLGATE MGLIYVNPEG PNHS--PLSA AAAIR-TF-R MGMNDEETVA LIAGGHTLGK
                                                                                H(269)

281                                                                      350
MTKATG     THGAGPADLV GPEPEAAPLE QMGLGWKSSY GTGTGKDAIT SGIEVVWNT PTKWDNSFLE ILYGYEWELT
ECKATG     THGAGPTSVG GPDPEAAPIE EQGLGWASTY GSGVGADAIT SGLEVVWTQT PTQWSNYFFE NLFKYEWVQT
STKATG     THGAGPAAASHV GADPEAAPIE AQGLGWASSY GSGVGADAIT SGLEVVWTQT PTQWSNYFFE NLFKYEWVQT
BSPERA     AHRGGPATHV GPEPEAAPIE AQGLGWISSY GKGKGSDTIT SGIEGAWTPT PTQWDTSYFD MLFGYDWWLT
 (CCP)     TH.....      GP-PEAAPIE SGYEGPWGAA NNVFTNEFYL NLLNEDWKLE
CONSENSUS  THGAGPASHV GP-PEAAPIE AQGLGWASSY GSGVGADAIT SG-EVVWTQT PTQW-N-FFE NLF-YEWVLT
            TH(275)                                                W(320)

351                                                                      420
MTKATG     KSPAGAWQYT AKDGAGAGTI PDPFGGPGR. ..SPTMLATD LSLRVDPIYE RITRRWLEHP EELADEFRKA
ECKATG     RSPAGAIQFE AVD...APEII PDPDPDSKKR KPTMLVTD LTLRFDPEFE KISRRFLNDP QAFNEAFARA
STKATG     RSPAGAIQFE AVD...APDII PDPFDPSKKR XXKPTMLVTD LTLRFDPEFE KISRRFLNDP QAFNEAFARA
BSPERA     KSPAGAWQWM AVDPDEKDLA PDAEDPSKK. .VPTMMMTD LALRFDPHQNP EEFAEAFARA
 (CCP)     KNDANNEQWD SKSGY.... ..... ..... .MMLPTD YSLIQDPKYL SIVKEYANDQ DKFFKDFSKA
CONSENSUS  KSPAGA-Q-E AVDG-APDII PDPFDPSKKR --KPTMLVTD L-LRFDPEYE KISRRFLNDP E-F-EAFARA
                                                      D(380)
```

FIG. 8A

```
           421                                                                            490
MTKATG   WYKLIHRDM. ........ .....GPVARYL GPLVPKQTLL WQDPVPAVST TSSAKQIASL KSQIRASGLT VSQLVSTAWA
ECKATG   WFKLTHRDM. ........ .....GPKSRYI GPEVPKEDLI WQDPLPQPIY NPTEQDIIDL KFAIADSGLS VSELVSVAWA  (SEQ ID NO:52)
STKATG   WFKLTHRDM. ........ .....GPKARYI GPEVPKEDLI WQDPLPQPLY QPTQEDIINL KAAIAASGLS ISEMVSVAWA
BSPERA   WFKLTHRDM. ........ .....GPKTRYL GPEVPKEDFI WQDPIPEVDY ELTEAEIEEI KAKILNSGLT VSELVKTAWA
  (CCP)  FEKLLENGIT FPKDAPSPFI ........... FKTLEEQGL. ........   ......... .........  .........
CONSENSUS WFKLTHRDM- ---------- ---GPK-RYI GPEVPKEDLI WQDP-PQ---Y -PTE-DII-L KAAIAASGL- VSELVS-AWA 491                                                                            560
MTKATG   AASSFRGSDK RGGA.NGGRI RLQPQVGWEV NDPDGSAQGH SHPEEIQESF TRRGNIKVSF ADLVVLGGCA
ECKATG   SASTFRGGDK RGGA.NGARL ALMPQRDWDV N..AAAVRAL PVLEKIQ... ...KESGKASL ADIIVLAGVV
STKATG   SASTFRGGDK RGGA.NGARL ALAPQRDWDV N..AVAARVL PVLEEIQ... ...KTTNKASL ADIIVLAGVV
BSPERA   SAA..RSATR ISAATNGRRI RLAPQKDWEV NEPERLAKVL SVLRGHPA.. ...RTAEKSKH RRLDRLGGTL
  (CCP)  ......... ......... ......... ......... ......... ......... .........
CONSENSUS SASTFRGGDK RGGA-NGAR- -LAPQRDW-V N-P--AARVL -VLEEIQ--- ---T--KASL AD-IVL-GVV 561                                                                            630
MTKATG   PLEKAAKAAG HNITVPF... TPGPHDASQE QTDVESFAVL EPKADGFRN. ...YLGKGNR CRPSTSLLDK
ECKATG   GVEKAASAAG LSIHVPF... APGRVDARQD QTDIEMFELL EPIADGFRN. ...YRARLDV STTESLLIDK
STKATG   GIEQAAAAAR VSIHVPF... PPGRVDARHD QTDIEMFSLL EPIADGFRN. ...YRARLDV STTESLLIDK
BSPERA   RWKRQPATPA LMSKCHFSLA AAMRHKSKPM SKALPCWNRS QMASATIKSK STRFRRKSCS STKPSSSADR
  (CCP)  ......... ......... ......... ......... ......... ......... .........
CONSENSUS G-EKAAAAAG LSIHVPF--- APGR-DARQD QTDIEMF-LL EPIADGFRN- ---YRA-LDV STTES-LIDK 631                                                                            700
MTKATG   ANLLTLSAPE MTVLVGGLRV LGANYKRLPL GVFTEASESL TNDFFVNLLD MGITWEPSPA DDGTYQGKD.
ECKATG   AQQLLTTAPE MTALVGGMRV LGGNFDGSKN GVFTDRGVL STDFFANLLD MRYEWKAIDE SKELFEGRDR
STKATG   AQQLLTLAPE MTVLVGGMRV LGTNFDGSQN GVFTDKPGVL STDFFANLLD MRYEWKPTDD ANELFEGRDR
BSPERA   PRNDGLSWR. ......FAR VGPNYRHLPH GVFTDRIGVL TNDFFVNLLD MNYEWVPTDS ..GIYEIRDR
  (CCP)  ......... ......... ......... ......... ......... ......... .........
CONSENSUS A-QLTL-APE MTVLVGGMRV LG-N-DG-PN GVFTDR-GVL -NDFFVNLLD MRYEWKPTD- ---L-EGRDR 701                  767
MTKATG   GSGKVKWNTGS ELRALVEVYA PMTRQAKFVT GFVAAWDKVM NLDRFDVR.. .....       (SEQ ID NO:48)
ECKATG   ETGEVKFTAS VLRAVAEVYA SSDAHEKFVK DFVAAWVKVM NLDRFDLL.. .....       (SEQ ID NO:49)
STKATG   LTGEVKYTAT VLRALAEVYA CSDAHEKFVK DFVAAWVKVM NLDRFDLQ.. .....       (SEQ ID NO:50)
BSPERA   KTGEVRWTAT RVDLIFGSNS ILRSYAEFYA QDDNQEKFVR DFINAWVKVM NADRFDLVKK ARESVTA     (SEQ ID NO:51)
  (CCP)  ......... ......... ......... ......... ......... .........                (SEQ ID NO:53)
CONSENSUS -TGEVKWTA- R-DLVFGSNS VLRALAEVYA -SDA-EKFVK DFVAAWVKVM NLDRFDL--- -----
```

FIG. 8B

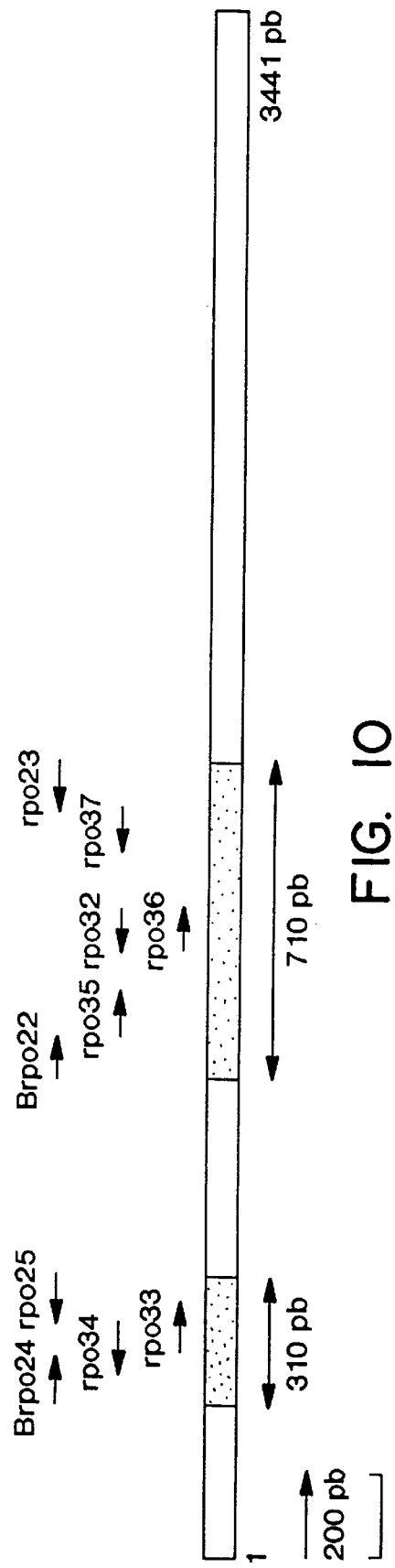

CAG TTC ATG GAT CAG AAC AAC CCT CTG TCG GGC CTG ACC CAC AAG CGC CGG CTG TCG (SEQ ID NO:54)

rpoB1,2,4,5,6,7 → TTG
rpoB3          ATG
rpoB8  TTC AAG
rpoB9          TTC

FIG. 11A

```
Frequence              1       1 4  4 2 4             2         3       4 1  3 1 1
                                L P  N V DQ            F         Y       C S  F  P
                               ∨ ∨   ∨                ↓         ↓       ∨ ∨  ∨ Δ
E.Coli      505  F F G S S Q L S Q F M D Q N N P L S E I T H K R R I S A L G P G G  537 (SEQ ID NO:55)
                     * Δ                          *
            399  F F G T S Q L S Q F M D Q N N P L S G L T H K R R L S A L G P G G  431 (SEQ ID NO:56)
                                    ↑                                     ↘↓↙
                                    FK                                    L F M
M.Leprae                             1                                    6 1 1
Frequence
```

FIG. 11B

```
ValProGlyAlaProAsnArgIleSerPheAlaLysLeuArgGluProLeuGluValPro
GTGCCCGGCGCGCCCAACCGAATTTCATTTGCCAAGCTCCGCGAACCGCTTGAGGTTCCG                60

GlyLeuLeuAspValGlnThrAspSerPheGluTrpLeuIleGlySerProCysTrpArg
GGGCTACTTGATGTGCAGACTGATTCATTTGAGTGGTTGATCGGATCGCCGTGCTGGCGT               120

AlaAlaAlaAlaSerArgGlyAspLeuLysProValGlyGlyLeuGluGluValLeuTyr
GCAGCGGCCGCAAGCCGCGGCGATCTCAAGCCGGTGGGTGGTCTCGAAGAGGTGCTCTAC               180

GluLeuSerProIleGluAspPheSerGlySerMetSerLeuSerPheSerAspProArg
GAGCTGTCGCCGATCGAGGATTTCTCCGGCTCAATGTCATTGTCTTTCTCCGATCCCCGT               240

PheAspGluValLysAlaProValGluGluCysLysAspLysAspMetThrTyrAlaAla
TTTGACGAAGTCAAGGCGCCCGTCGAAGAGTGCAAAGACAAGGACATGACGTACGCGGCC               300

ProLeuPheValThrAlaGluPheIleAsnAsnAsnThrGlyGluIleLysSerGlnThr
CCGCTGTTCGTCACGGCCGAGTTCATCAACAACAACACCGGGGAGATCAAGAGCCAGACG               360

ValPheMetGlyAspPheProMetMetThrGluLysGlyThrPheIleIleAsnGlyThr
GTGTTTATGGGCGACTTCCCTATGATGACTGAGAAGGGAACCTTCATCATCAACGGGACC               420

GluArgValValValSerGlnLeuValArgSerProGlyValTyrPheAspGluThrIle
GAGCGTGTCGTCGTTAGCCAGCTGGTGCGCTCCCCTGGAGTATACTTCGACGAGACGATC               480

AspLysSerThrGluLysThrLeuHisSerValLysValIleProSerArgGlyAlaTrp
GACAAGTCCACAGAAAAGACGCTGCATAGTGTCAAGGTGATTCCCAGCCGCGGTGCCTGG               540

LeuGluPheAspValAspLysArgAspThrValGlyValArgIleAspArgLysArgArg
TTGGAATTCGATGTCGATAAACGCGACACCGTCGGTGTCCGCATTGACCGGAAGCGCCGG               600

GlnProValThrValLeuLeuLysAlaLeuGlyTrpThrSerGluGlnIleThrGluArg
CAACCCGTCACGGTGCTTCTCAAAGCGCTAGGTTGGACCAGTGAGCAGATCACCGAGCGT               660

PheGlyPheSerGluIleMetArgSerThrLeuGluLysAspAsnThrValGlyThrAsp
TTCGGTTTCTCCGAGATCATGCGCTCGACGCTGGAGAAGGACAACACAGTTGGCACCGAC               720

GluAlaLeuLeuAspIleTyrArgLysLeuArgProGlyGluProProThrLysGluSer
GAGGCGCTGCTAGACATCTATCGTAAGTTGCGCCCAGGTGAGCCGCCGACTAAGGAGTCC               780

AlaGlnThrLeuLeuGluAsnLeuPhePheLysGluLysArgTyrAspLeuAlaArgVal
GCGCAGACGCTGTTGGAGAACCTGTTCTTCAAGGAGAAACGCTACGACCTGGCCAGGGTT               840

GlyArgTyrLysValAsnLysLysLeuGlyLeuHisAlaGlyGluLeuIleThrSerSer
GGTCGTTACAAGGTCAACAAGAAGCTCGGGTTGCACGCCGGTGAGTTGATCACGTCGTCC               900

ThrLeuThrGluGluAspValValAlaThrIleGluTyrLeuValArgLeuHisGluGly
ACGCTGACCGAAGAGGATGTCGTCGCCACCATAGAGTACCTGGTTCGTCTGCATGAGGGT               960
```

FIG. 12A

```
GlnSerThrMetThrValProGlyGlyValGluValProValGluThrAspAspIleAsp
CAGTCGACAATGACTGTCCCAGGTGGGGTAGAAGTGCCAGTGGAAACTGACGATATCGAC         1020

HisPheGlyAsnArgArgLeuArgThrValGlyGluLeuIleGlnAsnGlnIleArgVal
CACTTCGGCAACCGCCGGCTGCGCACGGTCGGCGAATTGATCCAGAACCAGATCCGGGTC         1080

GlyMetSerArgMetGluArgValValArgGluArgMetThrThrGlnAspValGluAla
GGTATGTCGCGGATGGAGCGGGTGGTCCGGGAGCGGATGACCACCCAGGACGTCGAGGCG         1140

IleThrProGlnThrLeuIleAsnIleArgProValValAlaAlaIleLysGluPhePhe
ATCACGCCGCAGACGCTGATCAATATCCGTCCGGTGGTCGCCGCTATCAAGGAATTCTTC         1200

GlyThrSerGlnLeuSerGlnPheMetAspGlnAsnAsnProLeuSerGlyLeuThrHis
GGCACCAGCCAGCTGTCGCAGTTCATGGATCAGAACAACCCTCTGTCGGGCCTGACCCAC         1260

LysArgArgLeuSerAlaLeuGlyProGlyGlyLeuSerArgGluArgAlaGlyLeuGlu
AAGCGCCGGCTGTCGGCGCTGGGCCCGGGTGGTTTGTCGCGTGAGCGTGCCGGGCTAGAG         1320

ValArgAspValHisProSerHisTyrGlyArgMetCysProIleGluThrProGluGly
GTCCGTGACGTGCACCCTTCGCACTACGGCCGGATGTGCCCGATCGAGACTCCGGAGGGC         1380

ProAsnIleGlyLeuIleGlySerLeuSerValTyrAlaArgValAsnProPheGlyPhe
CCGAACATAGGTCTGATCGGTTCATTGTCGGTGTACGCGCGGGTCAACCCCTTCGGGTTC         1440

IleGluThrProTyrArgLysValValAspGlyValValSerAspGluIleGluTyrLeu
ATCGAAACACCGTACCGCAAAGTGGTTGACGGTGTGGTCAGCGACGAGATCGAATACTTG         1500

ThrAlaAspGluGluAspArgHisValAlaGlnAlaAsnSerProIleAspGluAla
ACCGCTGACGAGGAAGACCGCCATGTCGTGGCGCAGGCCAACTCGCCGATCGACGAGGCC         1560

GlyArgSerSerSerArgAlaCysTrpValArgArgLysAlaGlyGluValGluTyrVal
GGCCGTTCCTCGAGCCGCGCGTGTTGGGTGCGCCGCAAGGCGGGCGAGGTGGAGTACGTG         1620

AlaSerSerGluValAspTyrMetAspValSerProArgGlnMetValSerValAlaThr
GCCTCGTCCGAGGTGGATTACATGGATGTCTCGCCACGCCAGATGGTGTCGGTGGCCACA         1680

AlaMetIleProPheLeuGluHisAspAspAlaAsnArgAlaLeuMetGlyAlaAsnMet
GCGATGATTCCGTTCCTTGAGCACGACGACGCCAACCGTGCCCTGATGGGCGCTAACATG         1740

GlnArgGlnAlaValProLeuValArgSerGluArgProLeuValGlyThrGlyMetGlu
CAGCGCCAAGCGGTTCCGTTGGTGCGCAGCGAACGACCGTTGGTGGGTACCGGTATGGAG         1800

LeuArgAlaAlaIleAspAlaGlyHisValValValAlaGluLysSerGlyValIleGlu
TTGCGCGCGGCCATCGACGCTGGCCACGTCGTCGTTGCGGAGAAGTCCGGGGTGATCGAG         1860

GluValSerAlaAspTyrIleThrValMetAlaAspAspGlyThrArgArgThrTyrArg
GAGGTTTCCGCCGACTACATCACCGTGATGGCCGATGACGGCACCCGGCGGACTTATCGG         1920
```

FIG. 12B

```
MetArgLysPheAlaArgSerAsnHisGlyThrCysAlaAsnGlnSerProIleValAsp
ATGCGTAAGTTCGCGCGCTCCAACCACGGCACCTGCGCCAACCAGTCCCCGATCGTGGAT      1980

AlaGlyAspArgValGluAlaGlyGlnValIleAlaAspGlyProCysThrGluAsnGly
GCGGGGGATCGGGTCGAGGCCGGCCAAGTGATTGCTGACGGTCCGTGCACTGAGAACGGC      2040

GluMetAlaLeuGlyLysAsnLeuLeuValAlaIleAsnAlaValGlyGlySerThrThr
GAGATGGCGTTGGGCAAGAACTTGCTGGTGGCGATCAATGCCGTGGGAGGGTCAACAACT      2100

AsnGluAspAlaIleIleLeuSerAsnArgLeuValGluGluAspValLeuThrSerIle
AACGAGGATGCGATCATCCTGTCTAACCGACTGGTCGAAGAGGACGTGCTTACTTCGATT      2160

HisIleGluGluHisGluIleAspAlaArgAspThrLysLeuGlyAlaGluGluIleThr
CACATTGAGGAGCATGAGATCGACGCCCGTGACACCAAGCTGGGTGCTGAGGAGATCACC      2220

ArgAspIleProAsnValSerAspGluValLeuAlaAspLeuAspGluArgGlyIleVal
CGGGACATTCCCAACGTCTCCGATGAGGTGCTAGCCGACTTGGACGAGCGGGGCATCGTG      2280

ArgIleGlyAlaGluValArgAspGlyAspIleLeuValGlyLysValThrProLysGly
CGGATTGGCGCGGAGGTTCGTGACGGTGATATCCTGGTTGGCAAGGTCACCCCGAAGGGG      2340

GluThrGluLeuThrProGluGluArgLeuLeuArgAlaIlePheGlyGluLysAlaArg
GAAACTGAGCTGACACCGGAAGAGCGGTTGCTGCGGGCGATCTTCGGCGAAAAGGCCCGC      2400

GluValArgAspThrSerLeuLysValProHisGlyGluSerGlyLysValIleGlyIle
GAGGTCCGTGACACGTCGCTGAAGGTGCCACACGGCGAATCCGGCAAGGTGATCGGCATT      2460

ArgValPheSerHisGluAspAspAspGluLeuProAlaGlyValAsnGluLeuValArg
CGGGTGTTCTCCCATGAGGATGACGACGAGCTGCCCGCCGGCGTCAACGAGCTGGTCCGT      2520

ValTyrValAlaGlnLysArgLysIleSerAspGlyAspLysLeuAlaGlyArgHisGly
GTCTACGTAGCCCAGAAGCGCAAGATCTCTGACGGTGACAAGCTGGCTGGGCGGCACGGC      2580

AsnLysGlyValIleGlyLysIleLeuProAlaGluAspMetProPheLeuProAspGly
AACAAGGGCGTGATCGGCAAGATCCTGCCTGCCGAGGATATGCCGTTTCTGCCAGACGGC      2640

ThrProValAspIleIleLeuAsnThrHisGlyValProArgArgMetAsnValGlyGln
ACCCCGGTGGACATCATCCTCAACACTCACGGGGTGCCGCGGCGGATGAACGTCGGTCAG      2700

IleLeuGluThrHisLeuGlyTrpValAlaLysSerGlyTrpLysIleAspValAlaGly
ATCTTGGAAACCCACCTTGGGTGGGTAGCCAAGTCCGGCTGGAAGATCGACGTGGCCGGC      2760

GlyIleProAspTrpAlaValAsnLeuProGluGluLeuLeuHisAlaAlaProAsnGln
GGTATACCGGATTGGGCGGTCAACTTGCCTGAGGAGTTGTTGCACGCTGCGCCCAACCAG      2820

IleValSerThrProValPheAspGlyAlaLysGluGluGluLeuGlnGlyLeuLeuSer
ATCGTGTCGACCCCGGTGTTCGACGGCGCCAAGGAAGAGGAACTACAGGGCCTGTTGTCC      2880
```

FIG. 12C

```
SerThrLeuProAsnArgAspGlyAspValMetValGlyGlyAspGlyLysAlaValLeu
TCCACGTTGGCCAACCGCGACGGCGATGTGATGGTGGGCGGCGACGGCAAGGCGGTGCTC    2940

PheAspGlyArgSerGlyGluProPheProTyrProValThrValGlyTyrMetTyrIle
TTCGATGGGCGCAGCGGTGAGCCGTTCCCTTATCCGGTGACGGTTGGCTACATGTACATC    3000

MetLysLeuHisHisLeuValAspAspLysIleHisAlaArgSerThrGlyProTyrSer
ATGAAGCTGCACCACTTGGTGGACGACAAGATCCACGCCCGCTCCACCGGCCCGTACTCG    3060

MetIleThrGlnGlnProLeuGlyGlyLysAlaGlnPheGlyGlyGlnArgPheGlyGlu
ATGATTACCCAGCAGCCGTTGGGTGGTAAGGCACAGTTCGGTGGCCAGCGATTCGGTGAG    3120

MetGluCysTrpAlaMetGlnAlaTyrGlyAlaAlaTyrThrLeuGlnGluLeuLeuThr
ATGGAGTGCTGGGCCATGCAGGCCTACGGTGCGGCCTACACGCTGCAGGAGCTGTTGACC    3180

IleLysSerAspAspThrValGlyArgValLysValTyrGluAlaIleValLysGlyGlu
ATCAAGTCCGACGACACCGTCGGTCGGGTCAAGGTTTACGAGGCTATCGTTAAGGGTGAG    3240

AsnIleProGluProGlyIleProGluSerPheLysValLeuLeuLysGluLeuGlnSer
AACATCCCCGAGCCGGGCATCCCCGAGTCGTTCAAGGTGCTGCTCAAGGAGTTACAGTCG    3300

LeuCysLeuAsnValGluValLeuSerSerAspGlyAlaAlaIleGluLeuArgGluGly
CTGTGTCTCAACGTCGAGGTGCTGTCGTCCGACGGTGCGGCGATCGAGTTGCGCGAAGGT    3360

GluAspGluAspLeuGluArgAlaAlaAlaAsnLeuGlyIleAsnLeuSerArgAsnGlu
GAGGATGAGGACCTCGAGCGGGCTGCGGCCAACCTCGGTATCAACTTGTCCCGCAACGAA    3420

SerAlaSerIleGluAspLeuAla***            (SEQ ID NO:58)
TCGGCGTCCATAGAAGATCTGGCTTAG    3447    (SEQ ID NO:57)
```

FIG. 12D

```
GlyAsnArgArgLeuArgThrValGlyGluLeuIleGlnAsnGlnIleArgValGlyMet
GGCAACCGCCGCCTGCGTACGGGTCGGGGAGCTGATCCAAAACCAGATCCGGGTCGGCATG          60

SerArgMetGluArgValValArgMetThrThrGlnAspValGluAlaAlaIleThr
TCGGGGATGGAGCGGGTGGTCCGGGAGCGGATGACCACCCAGGACGTGGAGGCGATCACA         120

ProGlnThrLeuIleAsnIleArgProValValAlaAlaIleLysGluPhePheGlyThr
CCGCAGACGTTGATCAACATCCGGCCGGTGGTCGCCGCGATCAAGGAGTTCTTCGGCACC         180

SerGlnLeuSerGlnPheMetAspGlnAsnAsnProLeuSerGlyLeuThrHisLysArg
AGCCAGCTGAGCCAATTCATGGACCAGAACAACCCGCTGTCGGGGTTGACGCACAAGCGC         240

ArgLeuSerAlaLeuGlyProGlyLeuSerArgGluArgAlaGlyLeuGluValArg
CGACTGTCGGCGCTGGGGCCCGGGCTCTCACGTGAGCGTGCCGGGCTGGAGGTCCGC            300

AspValHisProSerHisTyrGlyArgMetCysProIleGluThrProGluGlyProAsn
GACGTGCACCCGTCGCACTACGGCCGGATGTGCCCGATCGAAACCCTGAGGGGCCCAAC         360

IleGlyLeuIleGlySerLeuSerValTyrAlaArgValAsnProPheGlyPheIleGlu
ATCGGTCTGATCGGCTCGCTGTCGGTGTACGCGCGGGTCAACCCGTTCGGTTCATCGAA         420

ThrProTyrArg                (SEQ ID NO:60)
ACGCCGTACCGC        432     (SEQ ID NO:59)
```

FIG. 13

```
atgcccgatcacagggcactgcggcagggaataattgcactacgccaacatgttaacaac      20752

1
                  M   P   T   I   Q   Q   L   V   R   K   G
gaacacaatttacctgggagccggtatatgcccaccattcagcagctggtacgcaaggggt     20812
                                          c---------
        ML51

R   R   D   K   I   G   K   V   K   T   A   A   L   K   G   N   P   Q   R   R
cgtcgagacaagattggcaaggtcaagactgcggctctgaagggcaacccacagcgtcgc       20872
----g--------ca-t-----------c------------------g---g--------t
              S                                           S G   V   C   T   R   V   Y   T   S   P   K   K   P   N   S   A   L   R   K
ggtgtttgcacccgtgtgtacacttccaccccgaagaagccgaactcggcgcttcgcaag       20932
----a---------c---------ca----t--------------------------g---
                                T V   A   R   V   K   L   T   S   Q   V   E   V   T   A   Y   I   P   G   E   G
gttgcccgcgtgaagctgacgagtcaggttgaggtcacagcgtacataccaggcgagggt       20992
----------------t-------------c--------g--------t--c-------cg
                                                            A (SEQ ID NO:64)

H   N   L   Q   E   H   S   M   V   L   V   R   G   G   R   V   K   D   L   P
cacaacctacaggaacactccatggtgttggtgcgtggtggccgggtgaaagatctgcct       21052
--------g-----g-----g------c--------c--c-----------g--c------

G   V   R   Y   K   I   I   R   G   S   L   D   T   Q   G   V   K   N   R   K
ggtgtgcgttacaaaatcattcgcggttcgctcgacacccagggtgtcaagaaccggaag       21112
--------c-----g_____ (SEQ ID NO:63)
                                ML52

Q   A   R   S   R   Y   G   A   K   K   E   K   S   *          (SEQ ID NO:62)
caggctcgtagccgctatggagccaagaaggagaagagctga         21154         (SEQ ID NO:61)
```

FIG. 14

```
                          10
 R   K   G    R   R   D   K    I   G   K    V   K   T    A   A   L   K
CGCAAGGGTC  GTCGAGACAA  GATTGGCAAG  GTCAAGACCG  CGGCTCTGAA
    10          15           20          25

G   N   P    Q   R   R    G   V   C    T   R   V   Y    T   S   T
GGGCAGCCCG  CAGCGTCGTG  GTGTATGCAC  CCGCGTGTAC  ACCACCACTC
                30          35                      40

42
 P   K   K   P    N   S   A    L   R   K    V   A   R    V   K   L   T
CGAAGAAGCC  GAACTCGGCG  CTTCGGAAGG  TTGCCCGCGT  GAAGTTGACG
    45                      50          55

S   Q   V    E   V   T    A   Y   I    P   G   E   G    H   N   L   Q
AGTCAGGTCG  AGGTCACGGC  GTACATTCCC  GGCGAGGCGC  ACAACCTGCA
    60          65          70                      75

E   H   S    M   V   L    V   R   G    G   R   V   K    D   L   P
GGAGCACTCG  ATGGTGCTGG  TGCGCGGCGG  CCGGGTGAAG  GACCTGCCTG
                80          85                      90

G   V   R   Y   K        (SEQ ID NO:66)
   GTGTGCGCTAC  AAG.         (SEQ ID NO:67)
        95
```

FIG. 15

RAPID DETECTION OF ANTIBIOTIC RESISTANCE IN MYCOBACTERIUM TUBERCULOSIS

This is a continuation application of U.S. application Ser. No. 08/313,185, filed Oct. 12, 1994, now U.S. Pat. No. 5,851,763, which was the National Stage of International Application No. PCT/EP/01063, filed Apr. 30, 1993, which is a continuation of U.S. application Ser. No. 07/929,206, filed Aug. 14, 1992, now U.S. Pat. No. 5,633,131, which is a continuation-in-part of U.S. application Ser. No. 07/875,940, filed Apr. 30, 1992, now abandoned.

This invention relates to the rapid detection of strains of *Mycobacterium tuberculosis* that are resistant to antibiotics, particularly isoniazid, rifampicin and streptomycin. More particularly, this invention relates to a method of detecting antibiotic resistance in *Mycobacterium tuberculosis*, e.g. either as a result of mutations in the relevant genes or by nucleic acid hybridization. This invention also relates to a nucleic acid probe and a kit for carrying out the nucleic acid hybridization. The invention further relates to the chromosomal location of the katG gene (SEQ ID NO: 45) and its nucleotide sequence.

BACKGROUND OF THE INVENTION

Despite more than a century of research since the discovery of *Mycobacterium tuberculosis*, the aetiological agent of tuberculosis, by Robert Koch, this disease remains one of the major causes of human morbidity and mortality. There are an estimated 3 million deaths annually attributable to tuberculosis (Snider, 1989), and although the majority of these are in developing countries, the disease is assuming renewed importance in the West due to the increasing number of homeless people and the impact of the AIDS epidemic (Chaisson et al., 1987; Snider and Roper, 1992).

Isonicotinic acid hydrazide or isoniazid (INH) has been used in the treatment of tuberculosis for the last forty years due to its exquisite potency against the members of the "tuberculosis" groups—*Mycobacterium tuberculosis, M. bovis* and *M. africanum* (Middlebrook, 1952; Youatt, 1969). Neither the precise target of the drug, nor its mode of action, are known, and INH treatment results in the perturbation of several metabolic pathways. There is substantial evidence indicating that INH may act as an antimetabolite of NAD and pyridoxal phosphate (Bekierkunst and Bricker, 1967; Sriprakash and Ramakrishnan, 1970; Winder and Collins, 1968, 1969, 1970), and other data indicating that the drug blocks the synthesis of the mycolic acids, which are responsible for the acid-fast character of mycobacterial cell walls (Winder and Collins 1970; Quemard et al., 1991). Shortly after its introduction, INH-resistant isolates of *Mycobacterium tuberculosis* emerged and, on characterization, were often found to have lost catalase-peroxidase activity and to show reduced virulence in guinea pigs (Middlebrook et al., 1954; Kubica et al., 1968; Sriprakash and Ramakrishnan, 1970).

Very recently, INH-resistance has acquired new significance owing to a tuberculosis epidemic in the USA due to multidrug resistant (MDR) variants of *M. tuberculosis* (CDC, 1990; 1991a, b) and the demonstration that such strains were responsible for extensive nosocomial infections of HIV-infected individuals and health care workers (Snider and Roper, 1992). In view of the gravity of this problem, there exists a need in the art to determine the relationship between INH-resistance and catalase-peroxidase production.

More particularly, there is a need in the art to understand the molecular mechanisms involved in drug sensitivity. In addition, there is a need in the art to develop a simple test permitting the rapid identification of INH-resistant strains. Further, there is a need in the art for reagents to carry out such a test.

Rifampicin too is a major antibiotic used for the treatment of infections by mycobacterium, particularly *Mycobacterium tuberculosis* and *Mycobacterium leprae*. Because some mycobacteria grow slowly, possible rapid and efficient tests for the testing of resistance to rifampicin or analogues thereof must be made available. Likewise the invention aims at a rapid detection of strands of *Mybobacterium tuberculosis* which are resistant to streptomycin. Because of the development of resistance to streptomycin, the latter antibiotic has been used together with other antibiobics, e.g. isoniazid. Thus adequat treatment of tuberculosis should be preceded by rapid and efficient detection of resistances to the three majeur antibiotics, isoniazid, rifampicin and streptomycin.

SUMMARY OF THE INVENTION

Accordingly, this invention aids in fulfilling these needs in the art by providing a process for detecting in vitro the presence of cells of a *Mycobacterium tuberculosis* resistant to isoniazid and other drugs, such as rifampicin or analogues thereof, and streptomycin.

By analogues of rifampicin, a particularly meant derivatives of 3-formyl-rifamycin, particularly as a result of substitution the rein for the sustituant present either in the naphtofuranonyl group or of the site chain at position 7 of the naphtofuranonyl group, or by the introduction or removal of a double band in the lateral chain.

In accordance with the invention, the detection of a resistance to isoniazid involves the detection of one or several mutations in the katG gene (SEQ ID NO:45) of *Mycobacterium tuberculosis*, particularly with respect to the nucleotide sequence of that same katG gene (SEQ ID NO:45) in mycobacterium tuberculosis that are not resistant to isoniazid.

Another process alternative for detecting in vitro the presence of nucleic acids of a *Mycobacterium tuberculosis* resistant to isoniazid, wherein the process comprises the steps of:

contacting said nucleic acids previously made accessible to a probe if required under conditions permitting hybridization;

detecting any probe that had hybridized to said nucleic acids;

wherein said probe comprises a nucleic acid sequence, which is 2.5 kb EcoRV-KpnI fragment of plasmid pYZ56 or of part thereof, and wherein said fragment contains a BamHI cleavage site, wherein said part is nonetheless sufficiently long to provide for the selectivity of the in vitro detection of a *Mycobacterium tuberculosis* resistant to isoniazid.

For instance, this process alternative comprises the steps of (A) depositing and fixing nucleic acids of the cells on a solid support, so as to make the nucleic acids accessible to a probe;

(B) contacting the fixed nucleic acids from step (A) with a probe under conditions permitting hybridization;

(C) washing the filter resulting from step (B), so as to eliminate any non-hybridized probe; and then (D) detecting any hybridized probe on the washed filter resulting from step (C).

The probe comprises a nucleic acid sequence which is present in a 2.5 kb EcoRV-EnI fragment of plasmid pYZ56, wherein said fragment contains a BamHI cleavage site. This fragment has been found to be associated with intracellular DNA of isoniazid-sensitive *Mycobacterium tuberculosis* and is capable of distinguishing such anti-biotic sensitive microorganisms from isoniazid-resistant *Mycobacterium tuberculosis*, which do not contain DNA that hybridizes with this fragment under the conditions described hereinafter.

This invention further provides nucleotide sequences, such as RNA and DNA, of isoniazid-resistant *Mycobacterium tuberculosis* encoding the region of the katG gene of *Mycobacterium tuberculosis* (SEQ ID NO:45) that imparts isoniazid sensitivity absent from isoniazid-resistant cells.

This invention also provides a probe consisting of a label, such as a radionuclide, bonded to a nucleotide sequence of the invention.

In addition, this invention provides a hybrid duplex molecule consisting essentially of a nucleotide sequence of the invention hydrogen bonded to a nucleotide sequence of complementary base sequence, such as DNA or RNA.

Also, this invention provides a process for selecting a nucleotide sequence coding for a catalase-peroxidase gene of *Mycobacterium tuberculosis*, or for a portion of such a nucleotide sequence, from a group of nucleotide sequences, which comprises the step of determining which of the nucleotide sequences hybridizes to a nucleotide sequence of the invention. The nucleotide sequence can be a DNA sequence or an RNA sequence. The process can include the step of detecting a label on the nucleotide sequence.

Further, this invention provides a kit for the detection of *Mycobacterium tuberculosis* resistant to isoniazid. The kit comprises a container means containing a probe comprising a nucleic acid sequence, which is a 2.5 kb EcoRV-KpnI fragment of plasmid pYZ56, wherein the fragment contains a BamHI cleavage site. The kit also includes a container means containing a control preparation of nucleic acid.

The invention also covers compounds obtained as products of the action of the enzyme catalase, or a similar enzyme on isoniazid. The katG gene (SEQ ID NO:45) or a derivative of this gene which retains a similar activity can be used as a source of catalase protein. The new compounds are selected by reactivity on INH-resistant-mycobacterial strains by the antibiogram method such as described in H. David et al.'s "Methodes de laboratoire pour Mycobacteriologie clinique" edited by Pasteur Institute, ISBN N·0995-2454.

BRIEF DESCRIPTION OF THE DRAWINGS

This invention will be described in greater detail by reference to the drawings in which:

FIGS. 2A–C shows extracts from *M. tuberculosis* H37Rv and from E. coli strains transformed with a variety of plasmid constructs that were prepared for activity gel analysis as described previously (Zhang et al., 1991). Non-denaturing gels containing 8% polyacrylamide were stained for catalase (FIG. A) and peroxidase (FIG. B) activities as described by Wayne and Diaz (Wayne et al., 1986). Lane 1, *M. tuberculosis* H37Rv; 2, *E. coli* UM2 (katE. katG: 3, *E. coli* UM2/pYZ55; 4, *E. coli* UM2/pYZ56 (the 2.9 kb EcoRV-Krnl fragment in pUC19, corresponding to pBAK-KE+ in FIG. 1); 5, *E. coli* UM2/pYZ57 (pYZ55 with a BamHl-Kpnl deletion, corresponding to pBAK-KB+ in FIG. 1). *M. tuberculosis* catalase and peroxidase activities migrated as two bands under these conditions (lane 1); the same pattern was seen for the recombinant enzyme expressed by pYZ55 (lane 3). pYZ56 (lane 4) expresses a protein of increased molecular weight due to a fusion between katG and lacZ' from the vector as shown in panel C. Panel C also shows partial sequence alignment with *E. coli* HPI (SEQ ID NOS:42–44).

FIG. 6A. Nucleotide sequence of the KpnI fragment bearing katg. This sequence has been deposited in the EMBL data-library under accession number X68081. The deduced protein sequence is shown in the one letter code.

FIG 6B. Alignment of the two copies of the 700 bp direct repeat with identities shown as * and—denoting pads introduced to optimize the alignment. (SEQ ID NO:46–47) Numbering refers to the positions in FIG. 2A.

FIG. 8. Primary structure alignment of catalase-peroxidases (SEQ ID NO:48–53). The sequences are from *M. tuberculosis* H37RV, mtkatg (SEQ ID NO:48) ; *E.coli*, eckatg (SEQ ID NO:49) (Triggs-Raine et al., 1988); *S. typhimurium*, stkatg (SEQ ID NO:50); *B. stearothermophilus*, bspera (SEQ ID NO:51) (Loprasert et al., 1988) and yeast cytochrome c peroxidase (SEQ ID NO:52) (ccp; Finzel et al., 1984). The alignment was generated using PILEUP and PRETTY (Devereux et al., 1984) and . denote gaps introduced to maximize the homology. Key residues from the active site and the peroxidase motifs (Welinder, 1991), discussed in the text, are indicated below the consensus.

Figure 1:
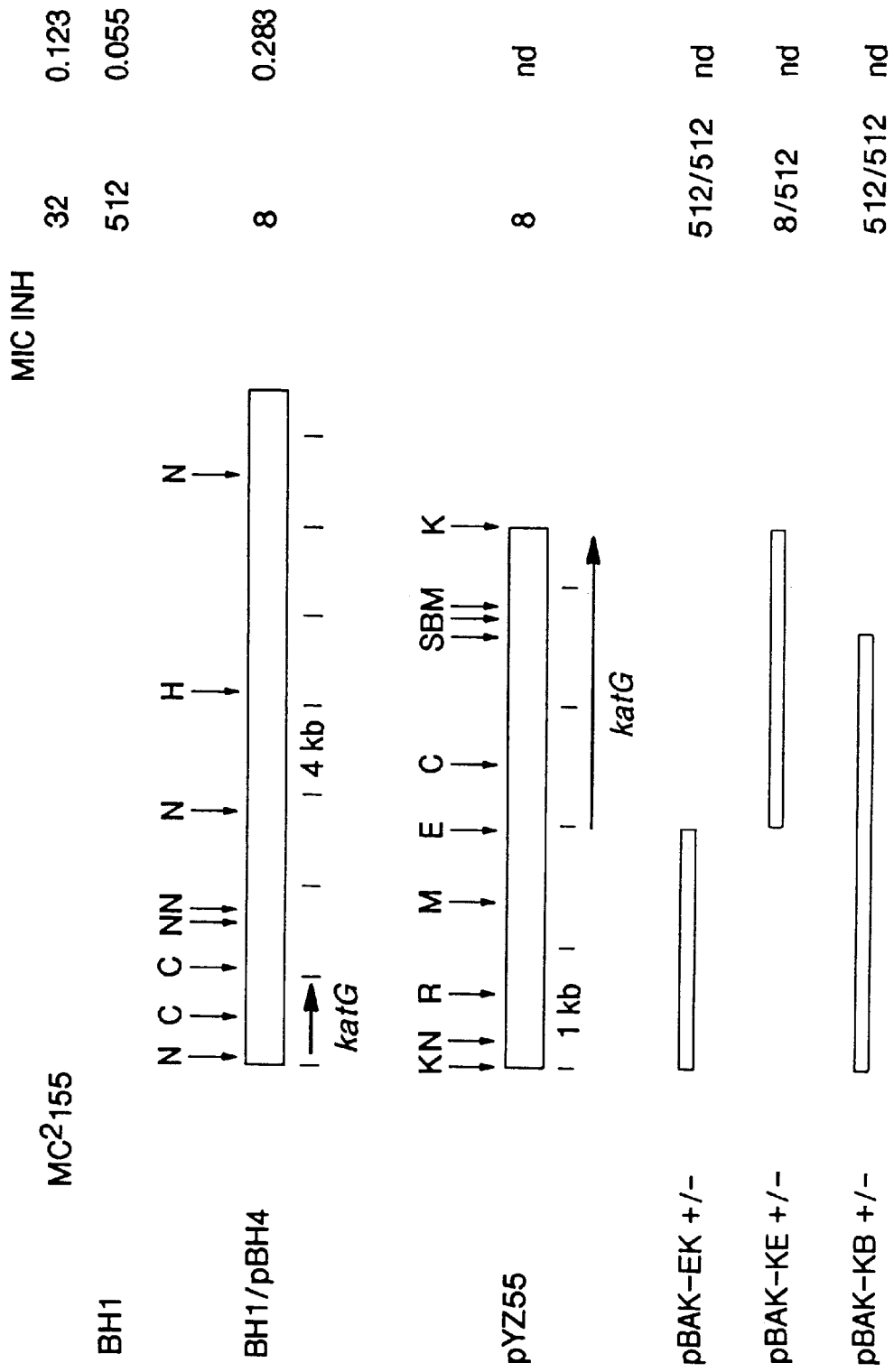
FIG. 1 shows the INH-resistant *M. smegmatis* strain, BH1 (Gayathri et al., 1975) (a derivative of strain $MC^2$-155) was transformed with a pool of *M. tuberculosis*-H37Rv shuttle cosmids (kindly provided by Dr. W. R. Jacobs, New York) and individual clones were scored for INH-susceptibility. Cosmid pBH4 consistently conferred drug susceptibility and the transformant overproduced catalase (assayed as in Heym, 1992). The restriction map of the DNA insert from pBH4 is shown along with that of the insert from pYZ55—a plasmid containing katG of *M. tuberculosis* H37Rv, isolated on the basis of hybridization with an oligonucleotide probe (5'-TTCATCCGCATGGCCTGGCA-CGGCGCGGGCACCTACCGC-31') (SEQ ID NO:1) designed to match the amino acid sequence from a conserved region of *E. coli* hydroperoxidase I (HPI). Restriction sites for the following enzymes are indicated : B, BamHl C, ClaI, E, EcoRV; H, HindIII, K, Kpnl; M, Smal; N, Notl; R, EcoRl; S, SacI. Transformation of BH1 with a mycobacterial shuttle plasmid, pBAK14, Zhang et al., 1991, containing the 4.5 kb insert from pYZ55 similarly conferred INH-susceptibility. MIC's are also shown for BH1 transformed with subfragments derived from pYZ55 and inserted into pBAK14 in one (+) or other (−) orientation. The katG gene (SEQ ID NO:45) and the ability to confer INH-susceptibility both mapped to a 2.9 kb EcoRV-Kpnl fragment (pBAK-KE+).
Figure 2A:
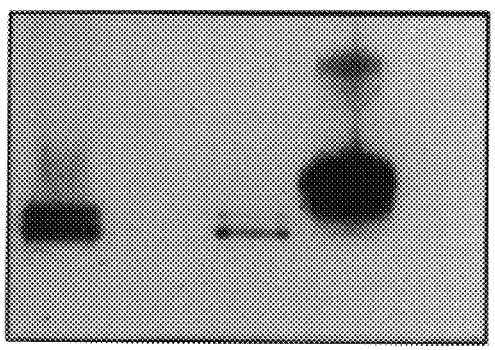
Figure 2B:
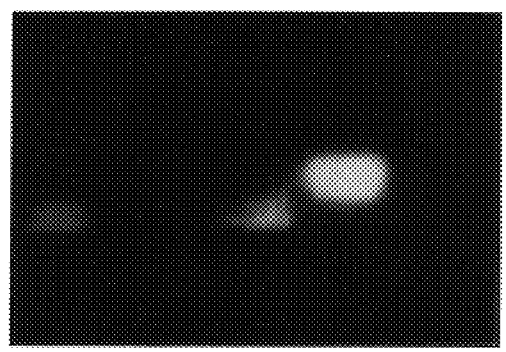
Figure 3:
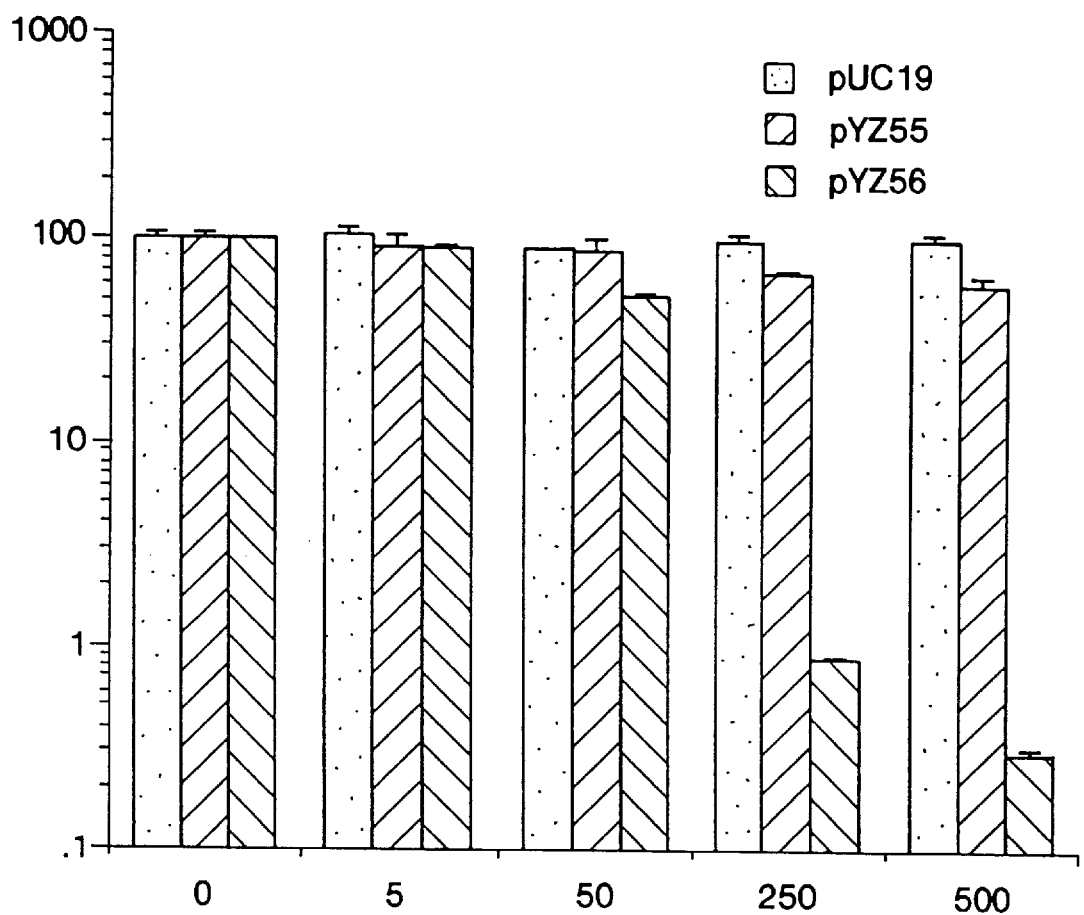
FIG. 3 shows an *E.coli* strain with mutations in both katG and katE (UM2 Mulvey et al., 1988) that was transformed with pUCl9 vector alone, pYZ55 expressing *M. tuberculosis* katG and pYZ56 with high level expression of *M. tuberculosis* katG. Overnight cultures in Luria-Bertani broth supplemented with appropriate antibiotics were plated out in the presence of varying concentrations of INH and colony forming units were assessed. Results of a representative experiment are shown with error bars indicating the standard deviation observed in triplicate samples. Overexpression of *M. tuberculosis* katG similarly conferred susceptibility to high concentrations of INH in *E.coli* UM255 (katG, katE, Mulvey et al., 1988), but had no effect on catalase-positive strains such as *E.coli* TG1. In some experiments, high concentrations of INH had detectable inhibitory effect on growth of UM2 and UM255, alone, but in all experiments inhibition of pYZ56-transformants was at least 10–100 fold greater than that observed in the corresponding vector controls.

Lane 1, soluble extract of *M. tuberculosis* H37Rv; lane 2, *M. smegmatis* MC$^2$155 harboring the vector pBAK14; lane 3, MC$^2$155 harboring pBAR-KK (katG+); lane 4, *E.coli* UM2 (katE, katG), lane 5, UM2 harboring pYZ55 (katG$^+$); lane 6, UM2 harboring pYZ56 (lacZ'::katG).

FIG. 10 represents diagrammatically the PCR strategy used for the study of different *M. Leprae* isolates showing the coding sequence of rpoB sequence. The sequenced regions are shown by hatched parts. The position and reference of the amplification primers used are indicated on the upper line. The sequencing primers are indicated below it.

FIG. 11 represents (A) the nucleotide sequence of a short region of rpoB (SEQ ID NO: 54) carrying mutations that confer resistance to rifampicin with an indication of the changes of bases in the corresponding alleles and (B) a comparison between the amino acid sequences of domain I of region II of the β-subunit of the RNA polymerase of *E.coli* (SEQ ID NO: 55) and *M. Leprae* (SEQ ID NO: 56). The numbers of the residues and the differences in the mutated amino acids have been indicated. The mutated amino acid residues associated with rifampicin resistance as well as the frequency of its occurrences have also been represented.

FIG. 12 shows a complete sequence of the rpoB gene of M. Leprae (SEQ ID NO: 56).

FIG. 13 represents the sequence of part of the rpoB gene of *M. tuberculosis* (SEQ ID NOS: 59–60).

FIG. 14 represents the sequence of a part of the rpsL gene of *M. tuberculosis* (SEQ ID NOS: 63–64). Both the sequence of the full rpsL gene of *M. Leprae* and that of its expression product (SEQ ID NOS: 61–62), that is the S12 protein (whose starting amino acid is noted by 1), are indicated. The positions of the ML51 (SEQ ID NO:40) and ML52 (SEQ ID NO:41) primers, as well as sequences of part of the rpsL gene of *M. tuberculosis*, are provided below those of *M. Leprae*. Only those positions that are different and the corresponding amino acid changes are indicated.

FIG. 15 represents the wild DNA sequence of the rpsL gene (SEQ ID NO:65) fragment coding for the S12 protein of the small ribosome subunit, which is responsible for the resistance to streptomycin, as well as the corresponding amino acid sequence of the S12 protein (SEQ ID NO:66).

DETAILED DESCRIPTION OF PREFERRED EMBODIMENT

The recent emergence of large numbers of strains of *M. tuberculosis* showing multidrug resistance in the United States is a most alarming development given the extreme contagiousness of this organism. This danger has been strikingly illustrated by several small tuberculosis epidemics in which a single patient infected with MDR *M. tuberculosis* has infected both HIV-positive individuals, prison guards and healthy nursing staff (CDC 1990, 1991; Daley et al., 1992; Snider and Roper, 1992). Given the gravity of the current worldwide HIV epidemic, it is conceivable that if AIDS patients in the West, like those in Africa, were to be infected with MDR *M. tuberculosis* strains (rather than members of the *M. avium/M. intracellulare* complex) widespread dissemination of the disease would result.

Isoniazid (INH) is a bactericidal drug which is particularly potent against the tuberculosis group of mycobacteria—*Mycobacterium tuberculosis, M. bovis,* and M. africanum—and, in consequence, it has been particularly effective in the treatment of tuberculosis. Standard antituberculosis regimens generally include INH and rifampicin, often in combination with the weaker drugs, pyrazinamide, ethambutol or streptomycin. Besides its use in therapy INH is also given to close contacts of patients as a prophylactic measure.

INH-resistant mutants of *M. tuberculosis*, the agent of the human disease, show two levels of resistance: low (1 to 10 μg/ml) and high (10 to 100 μg/ml). INH-resistance is often associated with loss of catalase activity and virulence. Recently, owing to the AIDS epidemic, increased homelessness and declining social conditions, tuberculosis has reemerged as a major public health problem in developed countries, particularly the USA. An alarming feature of the disease today is the emergence of multiple drug-resistant organisms and rapid nosocomial transmission to health care workers and HIV-infected patients. This has prompted CDC to propose new recommendations for the treatment of multiple resistant strains (at least INH and rifampicin) and the prevention of transmission. To obtain fresh insight into the problem of INH-resistance and to develop a rapid diagnostic test the following study was performed.

Clearly, it is essential to understand the mechanisms of resistance to INH and rifampicin, the main anti-tuberculosis agents, as this will allow novel chemotherapeutic strategies to be developed and facilitate the design of new compounds active against MDR strains.

This invention demonstrates that it is the catalase-peroxidase enzyme, HPI, which is the INH target, and it is suggested that this enzyme alone mediates toxicity. Compelling evidence of this conclusion was obtained by expression of the M. tuberculosis katg gene (SEQ ID NO:45) in a catalase-negative mutant of E.coli as this resulted in this bacterium becoming sensitive to INH. Moreover, the isolation of the M. tuberculosis INH-sensitivity gene, katG, (SEQ ID NO:45) is important as it will facilitate the rapid detection of INH-resistant strains by means of hybridization and PCR-based approaches. The high frequency of katG deletions in clinical strains, as shown here, should simplify this procedure.

Identification of an *M. tuberculosis* Gene Involved in INH-Sensitivity

A heterologous approach was employed to isolate *M. tuberculosis* gene(s) involved in INH-sensitivity. BH1 is a spontaneous mutant of the easily transformable *M. smegmatis* strain $MC^2155$ (Snapper et al., 1990), that is resistant to 512 $\mu$g/ml of the INH and lacks catalase-peroxidase activity (Heym et al., 1992). As there is a strict correlation between INH-sensitivity and these enzyme activities, transformation of BH1 with a plasmid carrying the appropriate gene from *M. tuberculosis* should lead to their restoration and concomitant INH-sensitivity.

Consequently, DNA was prepared from a pool of *M. tuberculosis* shuttle cosmids in *Escherichia coli* and introduced into BH1 by electro-transformation. Over 1000 kanamycin-resistant transformants were then scored for INH-sensitivity, and four clones that failed to grow on medium containing 32 g/ml of INH, the MIC from wild type strain $MC^2155$, were obtained.

After re-transformation of BH1, only one of these, pBH4, consistently conferred the INH-sensitive phenotype. Restriction digests with BamHI, KpnI, NotI, ClaI and HindIII showed the *M. tuberculosis* chromosomal DNA carried by pBH4 to be about 30 kb in size. A map produced with the last three enzymes is presented in FIG. 1.

When pBH4 was used as a hybridization probe to detect homologous clones in the library, a further eight shuttle cosmids were isolated. On transformation into BH1, five of these (T35, T646, T673, T79, T556) restored INH-sensitivity, and showed similar restriction profiles to pBH4. In particular, a KpnI fragment of 4.5 kb was present in all cases.

Attempts to subclone individual SamHI fragments did not give rise to transformants capable of complementing the lesion in BH1 suggesting that a BamHI site might be located in the gene of interest. In contrast, pBH5, a derivative of pBH4, was constructed by deletion of EcoRI fragments and this showed that a 7 kb segment was not required for restoration of INH-sensitivity.

Transformants harboring shuttle cosmids that complemented the INH-resistant mutation of BHI were examined carefully and the MICs for several antibiotics were established. In all cases, the MIC for INH had been reduced from 512 to 8 $\mu$g/ml, a value lower than that of the sensitive strain $MC^2155$ (32 $\mu$g/ml). This hypersensitive phenotype suggested that the recombinant clones might be overproducing an enzyme capable of enhancing INH-toxicity. Enzymological studies showed that these transformants all produced about 2-fold more peroxidase and catalase than the wild type strain $MC^2155$, which is INH-sensitive.

In addition to INH, many MDR-strains of *M. tuberculosis* are no longer sensitive to rifampicin, streptomycin, ethambutol and pyrazinamide. To examine the possibility that there might be a relationship between resistance to INH and these compounds, the MICs of several drugs for various *M. smegmatis* strains and their pBH4 transformants were determined, but no differences were found.

Cloning the *M. tuberculosis* Catalase Gene

A 45-mer oligonucleotide probe was designed based on the primary sequences of highly conserved regions in the catalase-peroxidase enzymes, HPI, of *E.coli* (Triggs-Raine et al., 1989), and *Bacillus stearothermophilus* (Loprasert et al., 1988). When genomic blots of *M. tuberculosis* DNA were probed with this oligonucleotide, specific bands were detected in most cases. As KpnI generated a unique fragment of 4.5 kb that hybridized strongly, this enzyme was used to produce a size selected library in pUC19.

Upon screening with the oligonucleotide probe, an appropriate clone, pYZ55, was obtained. A restriction map of the insert DNA is presented in FIG. 1 where it can be seen that this corresponds exactly to part of pBH4. Independent confirmation was also obtained by cross-hybridization.

By means of various subcloning experiments the smallest fragment expressing *M. tuberculosis* catalase-peroxidase activity in *E.coli* was found to be a 2.5 kb EcoRV-KpnI fragment which, as expected, contained a cleavage site for BamHI. Partial DNA sequence analysis showed that the katG gene carried by pYZ56 encodes a catalase-peroxidase enzyme that is highly homologous to the HPI enzymes of *E. coli* and *B. stearothermophilus: M. tuberculosis* APLNSWPDNASLDKARRLLWPSKMKYGKKLSWADLIV (SEQ ID NO:12) *E. coli* *******V*********I*Q***Q*I*****FI (SEQ ID NO:3) *B. stearothermophilus********N****C*GR**RNT*T*—*LGPICS (SEQ ID NO:4) (FIG. 2; Triggs-Raine et al., 1988); (Loprasert et al., 1988). Identical residues are indicated by *. HPI activity was detected in both *E.coli* and *M. smegmatis by staining (see below).*

Catalase-peroxidase Involvement in INH-Sensitivity

Having cloned the *M. tuberculosis* katG gene, (SEQ ID NO:45) it was of immediate interest to investigate the genetic basis of the association between catalase-negativity and isoniazid resistance. A series of constructs was established in the shuttle vector pBAK14 and used to transform the INH-resistant *M. smegmatis* mutant BH1. Only those plasmids carrying a complete katG gene produced HPI and restored INH-sensitivity. The smallest of these, pBAK14, carried a 2.5 kb EcoRV-KnI fragment thus demonstrating that the 2 kb region upstream of katG was not involved, and that catalase-peroxidase activity alone was sufficient to render mycobacteria susceptible to INH.

Cell-free extracts were separated by non-denaturating polyacrylamide gel electrophoresis and stained for peroxidase and catalase activity. Under these conditions, the *M. tuberculosis* enzyme gave two bands of peroxidase activity (lane 1) which comigrated with catalase activity (Heym et al., 1992).

When introduced into *E.coli*, the katG gene (SEQ ID NO:45) directed the synthesis of the same proteins, whereas pYZ56 produced proteins slightly larger in size. This is due to the construction of an in-frame lacZ::katG gene fusion. Activity stains were also performed with cell extracts of *M. smegmatis.* The presence of the katG gene (SEQ ID NO:45) from the *M. tuberculosis* in BH1 led to the production of catalase-peroxidase enzyme, which displayed the same electrophoretic mobility as the enzyme made in *M. tuberculosis,* or in *E.coli*, and the native HPI of *M. smegmatis.*

Basis of INH-resistance in *M. tuberculosis*

It has been known for many years that a subset of INH-resistant strains, particularly those resistant to the highest drug concentrations, are of lower virulence in the guinea pig and devoid of catalase activity. Genomic DNA was prepared from several clinical isolates of *M. tuberculosis* and analyzed by Southern blotting using the 4.5 kb KpnI fragment (SEQ ID NO:45) as a probe. In two highly resistant strains, B1453 and 24, the catalase gene has been deleted from the chromosome whereas in others (FIG. 3), such as strain 12, showing low level resistance it is still present but not expressed. Additional studies showed that the region immediately prior to katG was highly prone to rearrangements.

*M. tuberculosis* HPI Renders *E.coli* Sensitive to INH

To determine whether the HPI enzyme of *M. tuberculosis* could confer INH sensitivity on *E.coli*, a series of catalase mutants was transformed with pYZ56 and the MICs determined. Wild type strains were not susceptible to INH, but mutants lacking both endogenous catalase activities, but harboring pYZ56, showed growth inhibition when high levels of INH (500 μg/ml) were present, whereas untransformed strains were insensitive.

For purposes of this invention, a plasmid containing the restriction endonuclease map shown in FIG. 1 was deposited in strain with the National Collection of Cultures of Microorganisms (C.N.C.M.) of the Institut Pasteur, in Paris, France on May 18, 1992, under culture collection accession No. I-1209. This plasmid contains the nucleic acid sequence of the invention, namely, the 4.5 kb KpnI-KpnI fragment (SEQ ID NO:45) of plasmid pYZ56 having the BamHI cleavage site in the fragment.

In general, the invention features a method of detecting the presence of isoniazid-resistant *Mycobacterium tuberculosis* in a sample including providing at least one DNA or RNA probe capable of selectively hybridizing to isoniazid-sensitive *Mycobacterium tuberculosis* DNA to form detectable complexes. Detection is carried out with a sample under conditions which allow the probe to hybridize to isoniazid-sensitive *Mycobacterium tuberculosis* DNA present in the sample to form hybrid complexes and detecting the hybrid complexes as an indication of the presence of isoniazid-sensitive *Mycobacterium tuberculosis* in the sample. (The term "selectively hybridizing", as used herein, refers to a DNA or RNA probe which hybridizes only to isoniazid-sensitive *Mycobacterium tuberculosis* and not to isoniazid-insensitive *Mycobacterium tuberculosis*.) The sample can be comprised of the *Mycobacterium tuberculosis* cells or a portion of the cells or cell contents enriched in *Mycobacterium tuberculosis* nucleic acids, especially DNA. Hybridization can be carried out using conventional hybridization reagents. The particular hybridization conditions have not been found to be critical to the invention.

More particularly, DNA sequences from *Mycobacterium tuberculosis* can be analyzed by Southern blotting and hybridization. The techniques used for the present invention are described in Maniatis et al. (1989). DNA fragments can be separated on agarose gels and denatured in situ. The fragments can then be transferred from the gel to a water insoluble solid, porous support, such as a nitrocellulose filter, a nylon membrane, or an activated cellulose paper, where they are immobilized for example, the Hybond® membrane commercialized by Amersham can be used. After prehybridization to reduce non-specific hybridization with the probe, the solid support is hybridized to the nucleic acid probe of the invention. The solid support is washed to remove unbound and weakly binding probe, and the resulting hybrid duplex molecule is examined. A convenient alternative approach is to hybridize oligonucleotides to the DNA denatured in the gel.

The amount of labeled probe which is present in the hybridization solution will vary widely, depending upon the nature of the label, the amount of the labeled probe which can reasonably bind to the filter, and the stringency of the hybridization. Generally, substantial excesses of the probe over stoichiometric will be employed to enhance the rate of binding of the probe to the fixed DNA.

Various degrees of stringency of hybridization can be employed. The more severe the conditions, the greater the complementarity that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

Unlike Southern hybridization where DNA fragments are transferred from an agarose gel to a solid support, the method of the invention can also be carried out by oligonucleotide hybridization in dried agarose gels. In this procedure, the agarose gel is dried and hybridization is carried out in situ using an oligonucleotide probe of the invention. This procedure is preferred where speed of detection and sensitivity may be desirable. The procedure can be carried out on agarose gels containing genomic or cloned DNA of *Mycobacterium tuberculosis.*

In addition, the method of this invention can be carried out by transfer of *Mycobacterium tuberculosis* DNA from polyacrylamide gels to nylon filters by electroblotting. Electroblotting may be desirable where time is of the essence, because electroblotting is typically faster than capillary blotting developed to transfer DNA from agarose gels. This method can be carried out in conjunction with UV-crosslinking. The polyacrylamide gel containing the samples to be tested is placed in contact with an appropriately prepared nylon filter. These are then sandwiched into an electro-blotting apparatus and the DNA is transferred from the gel onto the filter using electric current. After a buffer rinse, the filter is ready to be prehybridized and hybridized or UV-crosslinked.

The method of the invention can be carried out using the nucleic acid probe of the invention for detecting *Mycobacterium tuberculosis* resistant to isoniazid. The probe can be detected using conventional techniques. The method of the invention can also detect point mutations in the KatG gene, (SEQ ID NO:45) as well as a partial deletion of that gene.

The nucleotides of the invention can be used as probes for the detection of a nucleotide sequence in a biological sample of *M. tuberculosis*. The polynucleotide probe can be labeled with an atom or inorganic radical, most commonly using a radionuclide, but also perhaps with a heavy metal. Radioactive labels include $^{32}$p, $^{3}$H, $^{14}$C, or the like. Any radioactive label can be employed, which provides for an adequate signal and has sufficient half-life. Other labels include ligands that can serve as a specific binding member to a labeled antibody, fluorescers, chemiluminescers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

In preferred embodiments of the invention, the probe is labeled with a radioactive isotope, e.g., $^{32}$p or 125I, which can be incorporated into the probe, e.g., by nick-translation.

In other preferred embodiments, the probe is labeled with biotin, which reacts with avidin to which is bonded a chemical entity which, when the avidin is bonded to the biotin, renders the hybrid DNA complex capable of being detected, e.g., a fluorophore, which renders the hybrid DNA complex detectable fluorometrically; an electron-dense compound capable of rendering the hybrid DNA complexes detectable by an electron microscope; an antibody capable of rendering the hybrid DNA complexes immunologically detectable; or one of a catalyst/substrate pair capable of rendering the hybrid DNA complexes enzymatically detectable. Prior to contacting the bacteria with the probe, the *M. tuberculosis* bacteria can be lysed to release their DNA, which is then denatured and immobilized on an appropriate solid, DNA-binding support, such as a nitrocellulose membrane.

Another detection method, which does not require the labeling of the probe, is the so-called sandwich hybridization technique. In this assay, an unlabeled probe, contained in a single-stranded vector, hybridizes to isoniazid-sensitive *Mycobacterium tuberculosis* DNA, and a labeled, single-stranded vector, not containing the probe, hybridizes to the probe-containing vector, labeling the whole hybrid complex.

The sequences of the invention were derived by dideoxynucleotide sequencing. The base sequences of the nucleotides are written in the 5'→3' direction. Each of the letters shown is a conventional designation for the following nucleotides:

A Adenine

G Guanine

T Thymine

C Cytosine.

The nucleotides of the invention can be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

The nucleotides of the invention are in a purified form. For instance, the nucleotides are free of human blood-derived proteins, human serum proteins, viral proteins, nucleotide sequences encoding these proteins, human tissue, and human tissue components. In addition, it is preferred that the nucleotides are free of other nucleic acids, extraneous proteins and lipids, and adventitious microorganisms, such as bacteria and viruses. This invention of course includes variants of the nucleotide sequences of the invention or serotypic variants of the probes of the invention exhibiting the same selective hybridization properties as the probes identical herein.

The nucleotide sequences of the present invention can be employed in a DNA amplification process known as the polymerase chain reaction (PCR). See. e.g., Kwok et al. (1987). PCR is advantageous because this technique is rapid.

DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the PBMC DNA. The PCR reaction mixture can contain the PBMC DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the PBMC DNA at an elevated temperature, cooling of the reaction mixture, and polymerization with the DNA polymerase.

Amplified sequences can be detected by the use of a technique termed oligomer restriction (OR). Single-strand conformation polymorphism (SSCP) analysis can be used to detect DNA polymorphisms and point mutations in a variety of positions in DNA fragments. See, Saiki et al. (1985); Orita et al. (1989). For example, after amplification, a portion of the PCR reaction mixture can be separated and subjected to hybridization with an end-labeled nucleotide probe, such as a $^{32}$p labelled adenosine triphosphate end-labeled. probe. In OR, an end-labeled oligonucleotide probe hybridizes in solution to a region of the amplified sequence and, in the process, reconstitutes a specific endonuclease site. Thus, hybridization of the labeled probe with the amplified katG sequence yields a double-stranded DNA form that is sensitive to selective restriction enzyme digestion. After restriction with an endonuclease, the resulting samples can be analyzed on a polyacrylamide gel, and autoradiograms of the portion of the gel with the diagnostic labeled fragment can be obtained. The appearance of a diagnostic fragment (e.g., 10–15 bases in length) in the autoradiogram indicates the presence of katG sequences (SEQ ID NO:45) in the PBMCS.

Since it may be possible to increase the sensitivity of detection by using RNA instead of chromosomal DNA as the original template, this invention contemplates using RNA sequences that are complementary to the DNA sequences described herein. The RNA can be converted to complementary DNA with reverse transcriptase and then subjected to DNA amplification.

EXPERIMENTAL PROCEDURES

Bacterial strains and plasmids

Table 1 outlines the properties of the bacterial strains and plasmids used in this invention.

TABLE 1

Bacterial Strains And Plasmids

| Strains/plasmids | Characteristics |
|---|---|
| *E. coli* NM554 | |
| *E. coli* TG1 | supE hsd5 thi delta (lac-proAB) [traD36 proAB+ $lacI^g$ lacZ delta M15] |
| *E. coli* UM2 | KatE |
| *E. coli* UM255 | KatE |
| *M. tuberculosis* H37Rv | Virulent strain originally isolated from tuberculosis patient |
| *M. tuberculosis* 12 | Clinical isolate resistant to low levels of INH (1–2 μg/ml) |
| *M. tuberculosis* B1453 | Clinical isolate resistant to high levels of INH (>50 μg/ml) |
| *M. tuberculosis* 24 | Clinical isolate resistant to high levels of INH (>50 μg/ml) |
| *M. tuberculosis* 79112 | Clinical isolate sensitive to INH |
| *M. tuberculosis* 12646 | Clinical isolate sensitive to INH |
| *M. tuberculosis* 79665 | Clinical isolate sensitive to INH |
| *M. smegmatis* $MC^2155$ | $MC^26$ het |
| *M. smegmatis* BH1 | $MC^2155$ het katG |

TABLE 1-continued

Bacterial Strains And Plasmids

Characteristics

Plasmids

| | |
|---|---|
| pBH4 | Shuttle cosmid, katG+, based on pYUB18 |
| pBH5 | Deleted version of pBH4, katG+, (7 kb-EcoRI) |
| pYZ55 | pUC19 derivative with 4.5 kb KpnI fragment, kat+ |
| pYZ56 | pUC19 derivative with 2.5 kb EcoRV-KpnI fragment (kat+) |
| pYZ57 | pUC19 derivative with 3.1 kb KpnI-BamHI fragment, kat− |
| pBAK14 | Mycobacterial shuttle vector (Zhang et al., 1991) |
| pBAK15 | Mycobacterial shuttle vector carrying 4.5 kb KpnI fragment (kat+) |
| pBAK16 | Mycobacterial shuttle vector carrying 2.5 kb EcoRV-KpnI fragment (kat+) |
| pBAK17 | Mycobacterial shuttle vector carrying 3.1 kb KpnI-BamHI fragment (kat−) |

The *M. tuberculosis* H37 RV genomic library was constructed in the shuttle cosmid pYUB18 (Snapper et al., 1988) and kindly supplied by Dr. W. R. Jacobs. Other shuttle vectors employed were pYUB12 (Snapper et al., 1988) and pBAK14 (Zhang et al., 1991).

Microbiological Techniques and Enzymology

Details of antibiotics used, growth conditions, enzymology and MIC determinations can be found in Heym et al., (1992).

Nucleic Acid Techniques

Standard protocols were used for subcloning, Southern blotting, DNA sequencing, oligonucleotide biosynthesis, etc. (Maniatis et al., 1989; Eiglmeier et al., 1991).

Activity Staining

The preparation of cell-free extracts of *E.coli* and mycobacteria has been described (Heym et al., 1992; Zhang et al., 1991). Native protein samples were separated by polyacrylamide gel electrophoresis as described by Laemmli (1970) except that SDS was omitted from all buffers, samples were not boiled and betamercaptoethanol was not included in the sample buffer. After electrophoresis of 50–100 μg protein samples on 7.5% polyacrylamide gels, catalase activity was detected by soaking the gel in 3mM $H_2O_2$ for 20 minutes with gentle shaking. An equal volume of 2% ferric chloride and 2% potassium ferricyanide was added and clear bands of catalase activity revealed by illumination with light. Peroxidase activity was detected as brown bands after soaking gels in a solution containing 0.2–0.5 mg/ml diaminobenzidine and 1.5 mM $H_2O_2$ for 30–120 minutes.

To generate a highly toxic compound it seems most likely that the *M. tuberculosis* HPI enzyme peroxidatively activates INH (Youatt, 1969; Gayathri-Devi et al., 1975). Now that the katG gene (SEQ ID NO:45) has been isolated and characterized, it should be possible to make new derivatives of INH, which can be activated in a similar manner.

EXAMPLE 1

Point Mutations in the katG Gene Associated with the Isoniazid-Resistance of *M. tuberculosis*

It has been shown in a recent study that the catalase-peroxidase of *Mycobacterium tuberculosis*, encoded by the katG gene, is involved in mediating the toxicity of the potent anti-tuberculosis drug isoniazid or INH. Mutants resistant to clinical levels of INH show reduced catalase-peroxidase activity and, in some cases, this results from the deletion of the katG gene (SEQ ID NO:45) from the chromosome. Transformation of INH-resistant strains of *Mycobacterium smegmatis* and *M. tuberculosis* with the cloned katG gene leads to restoration of drug-sensitivity. Expression of katG (SEQ ID NO:45) in some strains of *Escherichia coli* renders this naturally resistant organism susceptible to high concentrations of INH.

As some INH-resistant clinical isolates of *M. tuberculosis* have retained an intact katG gene, the molecular basis of their resistance was investigated. This study was facilitated by the availability of the nucleotide sequence of a 4.7 kb KpnI fragment from the katG region (SEQ ID NO:45) of the chromosome as this allowed primers suitable for PCR analysis to be designed. Eleven pairs of oligonucleotide primers were synthesized (SEQ ID NOS:5–26) (see Table 2) and used to generate PCR-products, of around 280 bp, that covered the complete katG gene (SEQ ID NO:45) and some of the flanking sequences. In control experiments all experiments all eleven primer pairs generated PCR products of the expected size, highly suitable for SSCP-analysis, so a panel of 36 INH-resistant strains of *M. tuberculosis*, of Dutch or French origin, was examined. Many of these strains are multidrug resistant and were isolated from patients who were HIV-seropositive.

Table 2

Sequences of primer pairs used for PCR-SSCP analysis of the katG gene (SEQ ID NO:45) of M.tuberculosis

| Primer Pair # | 1 | 5' | 3' | Length | G+C(%) | Tm | Production |
|---|---|---|---|---|---|---|---|
| OLIGO1: | GCGGGGTTATCGCCGATG (SEQ ID NO:5) | 1765 | 1782 | 18 | 66 | 61.8 | 288 |
| OLIGO2: | GCCCTCGACGGGGTATTTC (SEQ ID NO:6) | 2052 | 2034 | 19 | 63 | 61.9 | |
| Primer Pair # | 2 | | | | | | |
| OLIGO1: | AACGGCTGTCCCGTCGTG (SEQ ID NO:7) | 2008 | 2025 | 18 | 66 | 61.9 | 300 |
| OLIGO2: | GTCGTGGATGCGGTAGGTG (SEQ ID NO:8) | 2307 | 2289 | 19 | 63 | 61.9 | |
| Primer Pair # | 3 | | | | | | |
| OLIGO1: | TCGACTTGACGCCCTGACG (SEQ ID NO:9) | 2169 | 2187 | 19 | 63 | 61.9 | 280 |
| OLIGO2: | CAGGTCCGCCCATGACAG (SEQ ID NO:10) | 2448 | 2431 | 18 | 66 | 61.9 | |
| Primer Pair # | 4 | | | | | | |
| OLIGO1: | CCACAACGCCAGCTTCGAC (SEQ ID NO:11) | 2364 | 2382 | 19 | 53 | 61.9 | 284 |
| OLIGO2: | GGTTCACGTAGATCAGCCCC (SEQ ID NO:12) | 2647 | 2628 | 20 | 50 | 61.9 | |
| Primer Pair # | 5 | | | | | | |
| OLIGO1: | GCAGATGGGGCTGATCTACG (SEQ ID NO:13) | 2622 | 2641 | 20 | 60 | 51.9 | 288 |

Table 2-continued Sequences of primer pairs used for PCR-SSCP analysis of the katG gene (SEQ ID NO:45) of M.tuberculosis

```
OLI

TABLE 3-continued

Preliminary results of PCT-SSCP analysis of katG from *M. tuberculosis* strains
x denotes altered mobility; del denotes deletion

| N° | Strain | MIC (INH) | 1<br>1765–<br>2034 | 2<br>2008–<br>2289 | 3<br>2169–<br>2431 | 4<br>2364–<br>2628 | 5<br>2622–<br>2892 | 6<br>2829–<br>3097 | 7<br>3088–<br>3367 |
|---|---|---|---|---|---|---|---|---|---|
| 39 | 9582 | 1 | | | | | x | | |
| 41 | H37Rv | — | | | | | | | |
| 42 | Ass | — | | | | | | | |
| 43 | Mou | — | | | | | | | |
| 44 | 13632 | >20 | del | del | del | del | del | del | del |
| 45 | 13549 | >5 | del | del | del | del | del | del | del |
| 46 | 13749 | >20 | | | | | | | |
| 47 | 14006 | 10 | | | | | | | x |
| 48 | 13711 | >5 | | | | | | | |
| 49 | 13681 | >5 | | | | | x | | |
| 50 | 14252 | >5 | | | | | | | |

On examination of a 200 bp segment of the katG gene from five independent strains (9188, 9106, 9441, 9444, 9363), a single base difference was found. This was the same in all cases, a G to T transversion at position 3360, resulting in the substitution of Arg-461 by Leu. Thus, in addition to inactivation of katG, INH-resistance can stem from missense mutations that result in an altered catalase peroxidase. This mutation may define a site of interaction between the drug and the enzyme. The results of DNA sequence studies with the remaining mutants are eagerly awaited.

Another conclusion that can be drawn from this study concerns the molecular basis of the multidrug resistance associated with various *M. tuberculosis* strains. The same mutations are found irrespective of whether a given patient is seropositive or seronegative for HIV. For example, strain 9291, isolated from an HIV-seropositive tuberculosis patient, harbors mutations conferring resistance to INH, rifampin and streptomycin in the katG (R461L), rpoB (S425L) and rpsL (K42R) genes, respectively. The same mutations have been found separately, or in combination, in strains from HIV-seronegative individuals. This means that, for the set of strains studied, there is no novel, single mechanism conferring resistance to several drugs, but rather, multidrug resistance results from the accumulation of mutations in the genes for distinct drug targets.

EXAMPLE 2

Nucleotide Sequence and Chromosomal Location of the katG Locus of *M. tuberculosis*

Bacterial strains, plasmids and growth conditions. The following bacterial strains from our laboratory collections were used in this study: *M. tuberculosis* H37Rv: *M. smegmatis* MC²155 (Snapper et al., 1990); *E.coli* K-12 UM2 (katE katG; Mulvey et al., 1988). The recombinant plasmids, pYZ55 (pUC19, katG⁺), pYZ56 (pUC19, lacZ'::katG) and the shuttle clones, pBH4 (pYUB18, katG⁺) and PBAK-KK- (pBAK14, katG⁺) have been described recently (Zhang et al. 1992, *Nature*) and the katG locus of *M. tuberculosis* is schematized in FIG. 5. Mycobacteria were grown at 37° C. in Middlebrook 7H9 medium, while *E.coli* strains were cultivated in L-broth, with appropriate enrichments and antibiotics.

Nucleic acid techniques. Standard techniques were employed for the preparation, labelling and hybridization of DNA (Eiglmeier et al. 1991; Zhang et al. 1992, *Infect. Immun.*; Zhang et al. 1992, *Nature*). A shotgun library of random fragments of pYZ55 was prepared in M13mp18 as described previously (Garnier et al., 1986) and sequenced using the modified dideoxy technique (Biggin et al. 1983). Sequences were compiled and assembled into contigs using SAP, and analyzed with NIP, SIP and PIP (Staden 1987) running on a Vax 3100 workstation. Gap closure was obtained by using synthetic oligonucleotide primers, synthesized on an ABI 381 apparatus, and T7 DNA polymerase (Pharmacia) to obtain sequences directly from pYZ55. To search for related sequences in the GenBank database (release 73.1) the FASTA (Pearson et al. 1988) and BLAST (Altschul et al. 1990) programs were used. The PROSITE (Bairoch 1992) catalog was screened to detect possible motifs present in protein sequences and alignments were done with the PILEUP and PRETTY modules of the GCG sequence analysis package (Devereux et al. 1984).

Western blotting and catalase-peroxidase activity staining. Immunoblotting of polypeptides resolved by SDS-polyacrylamide gel electrophoresis and detection with polyclonal antibodies (purchased from DAKO) raised against *M. bovis* BCG, were as described (Zhang et al. 1992, *Infect. Immun., Nature, Mol. Microbiol.*). Procedures for detecting catalase and peroxidase activities have been outlined recently (Heym et al. 1992; Zhang et al. 1992, *Nature*).

RESULTS

Nucleotide Sequence of the katG Locus (SEQ ID NO:45) of *M. tuberculosis*.

Figure 5:
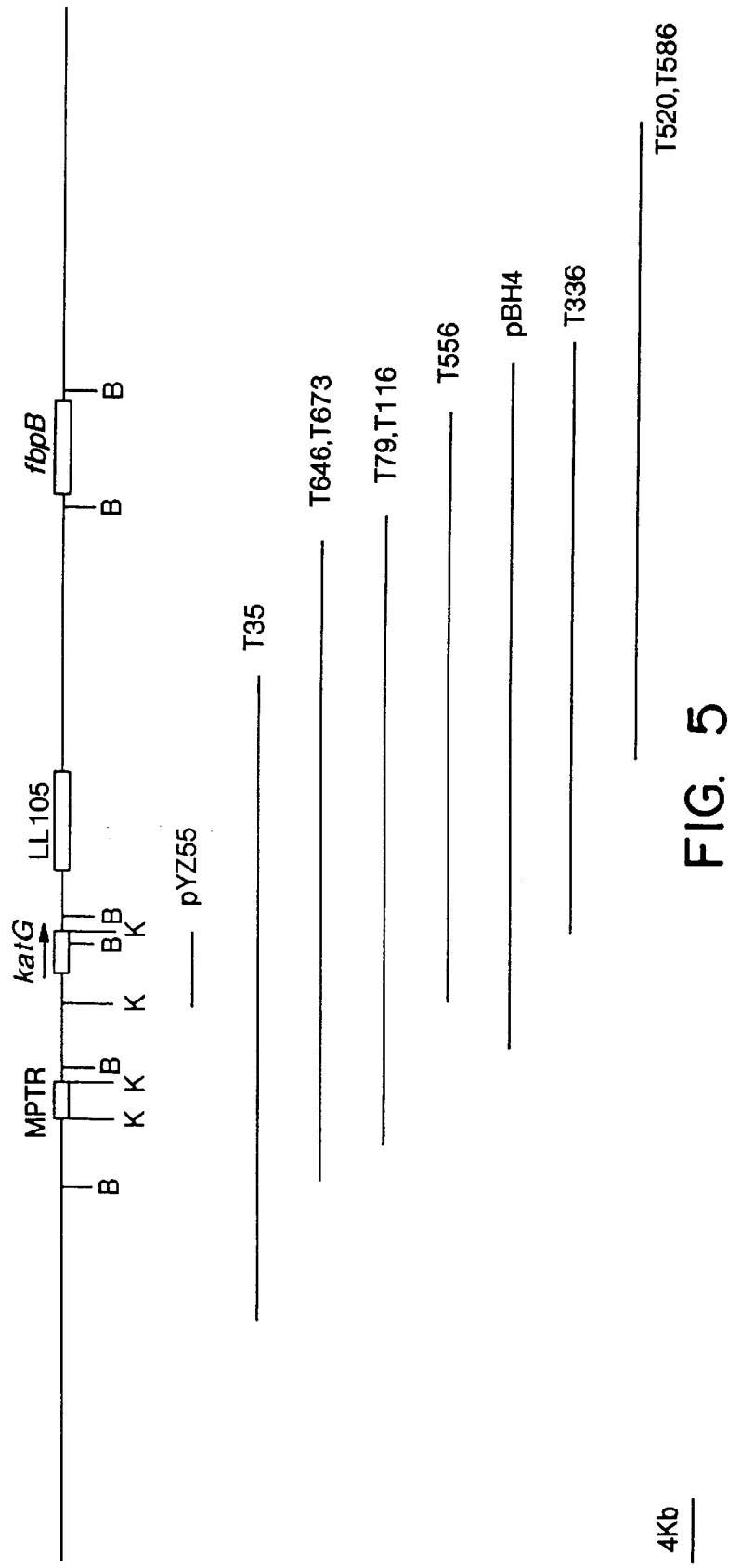
FIG. 5. Organization of the katG locus. The upper bar corresponds to a stretch of the *M. tuberculosis* chromosome spanning the katG region and the positions of individual cosmids used to construct the map are shown below together with the original shuttle cosmid pBH4 and pYZ55. The locations of some key restriction sites (B, BamnHI; K, KpnI) are shown together with the approximate location of the known genetic markers: fbpB encoding the alpha or 85-B antigen (Matsuo et al., 1988); katG, catalase-peroxidase; LL105, an anonymous λgtll clone kindly supplied by Å Andersen; MPTR, major polymorphic tandem repeat (Hermans et al., 1992).

In previous studies, the complete katG gene (SEQ ID NO:45) was cloned independently in *E.coli* on a shuttle cosmid, pBH4, and on a 4.5 kb KpnI restriction fragment thus giving rise to pYZ55 (FIG. 5; Zhang et al. 1992, *Nature*). The structural gene for catalase-peroxidase was subsequently localized to a 2.5 kb EcORV-KpnI fragment by sub-cloning. To deduce the primary structure of this important enzyme and thereby gain some insight into its putative role in the conversion of INH into a potent anti-tuberculous derivative, the nucleotide sequence of the complete insert from pYZ55 was determined. This was achieved by the modified dideoxy-shotgun cloning procedure (Biggin et al. 1993) and gaps between the contigs were closed by using specific primers.

On inspection of the resultant sequence which is shown in FIG. 6A, the 4.5 kb fragment (SEQ ID NO:45) was found to contain 4795 nucleotides with an overall dG+dC content of 64.4%. When this was analyzed for the presence of open reading frames, with high coding-probability values, a single candidate was detected and, from its size, composition and location, this was identified as katG (SEQ ID NO:45). The absence of any additional open reading frames, on either strand of the KIn fragment, ruled out the possibility that genes other than katG were involved in conferring INH-susceptibility.

Further analysis of the sequence showed katG (SEQ ID NO:45) to be preceded by two copies of a 700 bp direct repeat which were 68% identical, with the longest stretch of identity comprising 58 bp (FIG. 6B) (SEQ ID NO:46–47). When the databases were screened with this sequence no significant homologies were detected. To test the possibility that it could correspond to a new repetitive element in *M. tuberculosis*, a 336 bp probe, encompassing the 58 bp repeat, was used to probe a partially-ordered cosmid library. Positive hybridization signals were only obtained from clones that were known to carry katG. Likewise, a single restriction fragment was detected in Southern blots of *M. tuberculosis* DNA digested with restriction enzymes BamHI, kpnI and RsrII thereby indicating that this repetitive sequence is not dispersed.

Chromosomal location of katG (SEQ ID NO:45). As part of the *M. tuberculosis* genome project, most of the genes for which probes are available have been positioned on the contig map. From the series of overlapping cosmids shown in FIG. 5 it can be seen that the markers linked to katG are LL105 and fbpB encoding an anonymous antigen and the putative fibronectin binding protein, or alpha antigen (Matsuo et al. 1988), respectively. None of the known insertion sequences IS6110 and IS1081 (Collins et al. 1991; McAdam et al. 1990; Thierry et al. 1990, *J. Clin. Microbiol.*; Thierry et al. 1990, *Nucleic Acids Res.*), map to this area of the chromosome although the region upstream of katG (SEQ ID NO:45) is densely populated with copies of the major polymorphic tandem repeat, MPTR (Hermans et al. 1992; Zhang and Young 1993).

Presence of katG (SEQ ID NO:45) homologues in other mycobacteria. INH is exquisitely potent against members of the tuberculosis complex yet shows little, if any, activity against other mycobacteria. To determine whether genes homologous to katG (SEQ ID NO:45) were present in other mycobacteria Southern blots of DNA digested with RsrII were hybridized with a probe prepared from a 2.5 kb EcoRV-KpnI restriction fragment carrying katG (SEQ ID NO:45) from *M. tuberculosis*. Under conditions of high stringency good signals were obtained from *M. leprae* and *M. avium* (FIG. 7) while barely discernible hybridization was observed with *M. gordonae* and *M. szulgai*. It has been shown recently that katG homologues are also present in *M. Smegmatis* and *M. aurum* (Heym et al. 1992).

Predicted properties of catalase-peroxidase from *M. tuberculosis*. The primary structure of catalase-peroxidase, deduced from the nucleotide sequence of katG (SEQ ID NO:45), is shown in FIG. 6 (SEQ ID NO:49). The enzyme is predicted to contain 735 amino acids, and to display a molecular weight of 80,029 daltons. A protein of this size has been observed in *M. tuberculosis* (SEQ ID NO:48), and both recombinant *M. smegmatis* and *E.coli* (SEQ ID NO:49) (see below).

Primary structures are available for several other bacterial catalase-peroxidases including those from *E.coli*, *salmonella tylhimurium* (SEQ ID NO:50) and *Bacillus stearothermohilus* (SEQ ID NO:51) (Loewen et al. 1990; Loprasert et al. 1988; Triggs-Raine et al. 1988) and these have been shown to be distantly related to yeast cytochrome c peroxidase (SEQ ID NO:52) (Welinder 1991). As the crystal structure of the latter has been determined (Finzel et al. 1984) this can be used to interpret the sequences of the bacterial enzymes. The *M. tuberculosis* enzyme (SEQ ID NO:48) shows 53.3% conservation with the enterobacterial HPI enzymes, and shares 45.7% identity with the protein from *B. stearothermophilus*(SEQ ID NO:51). An alignment of the sequences of these four enzymes is shown in FIG. 8 (SEQ ID NOS:48–51), along with that of yeast cytochrome c peroxidase (SEQ ID NO:52) (Welinder 1991). It is apparent that the $NH_2$ terminus, which has no counterpart in the yeast enzyme, is the most divergent part suggesting that this domain of the protein can tolerate extensive deviation and is not required for catalysis. Experimental support for this interpretation is provided in the form of a LacZ-KatG fusion protein which contains an additional 40 amino acid residues (FIG. 9, lane 6; Zhang et al. 1992, *Nature*). Addition of this $NH_2$-terminal segment does not noticeably interfere with either the catalase or peroxidase reactions effected by KatG (SEQ ID NO:48) as judged by activity staining (Zhang et al. 1992, *Nature*). Bacterial catalase-peroxidases are believed to have evolved by means of a gene duplication event and consist of two modules, both showing homology to the yeast enzyme, fused to a unique $NH_2$-terminal sequence of about 50 amino acid residues (Welinder 1991). The *M. tuberculosis* enzyme (SEQ ID NO:48) conforms to this pattern and when searched for internal homology using SIP (Staden 1987) it was clear that the region between residues 55–422 was related to the carboxy terminal domain, consisting of amino acids 423–735. Only one of the two active site motifs typical of peroxidases, present in the PROSITE catalog (Bairoch 1992) was found when the *M. tuberculosis* catalase-peroxidase. primary structure (SEQ ID NO:48) was screened as there are two deviations from the consensus around $His^{269}$ where the second motif should be. (Consensus pattern for peroxidase 1: [DET]-[LIVMT]-x(2)-[LIVM]-[LIVMSTAG]-[SAG]-[LIVMSTAG]-H-[STA]-[LIVMFY](SEQ ID NO:27); consensus pattern for peroxidase 2: [SGAT]-x(3)-[LIVMA]-R-[LIVMA]-x-[FW]-H-x-[SAC](SEQ ID NO:28); (Bairoch 1992). In addition, a possible ATP-binding motif (G-x-x-x-x-G-K-T) was detected (Balroch 1992) but as this partially overlaps the active site its presence may be purely fortuitous (FIG. 8).

Figure 4A:
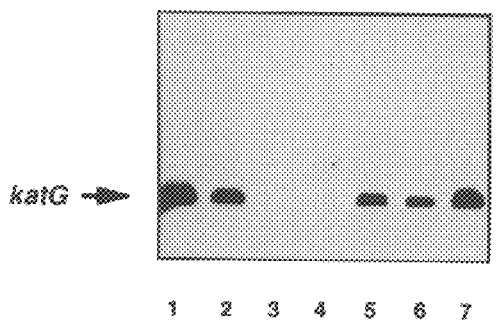
FIGS. 4A and 4B shows Southern blots prepared using genomic DNA from different *M. tuberculosis* strains, digested with Kpnl, that were probed with (A) katG (the 4.5 kb Kpnl fragment), (SEQ ID NO:45) and (B) the SOD gene (1.1 kb EcoRl-Kpnl fragment, Zhang et al., 1991). Labelling of probes and processing of blots was performed as described previously (Eiglmeier et al., 1991; Maniatis et al., 1989). Lane 1, H37Rv; 2, strain 12—MIC 1.6 $\mu$g/ml INH; 3, B1453—MIC >50 $\mu$g/ml INH (Jackett et al., 1978); 4, strain 24—MIC >50 $\mu$g/ml INH; 5, 79112—INH-sensitive (Mitchison et al., 1963); 6, 12646—INH-sensitive (Mitchison et al., 1963); 7, 79665—INH-sensitive (Mitchinson et al., 1963). INH susceptibilities were confirmed by inoculation of Lowenstein-Jensen slopes containing differing concentrations of INH.
Figure 4B:
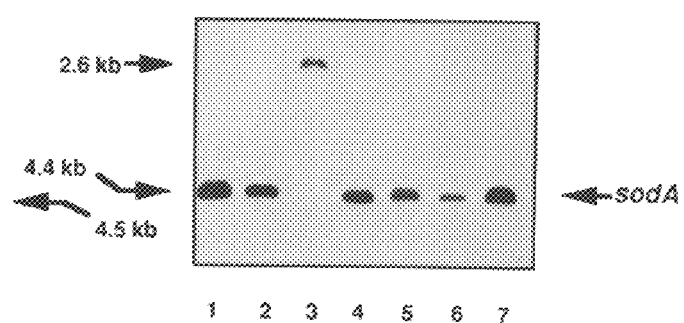

By analogy with yeast cytochrome c peroxidase (SEQ ID NO:52) (Welinder 1991), it was possible to predict a number of structurally and catalytically important residues all of which are located in the $NH_2$-terminal repeat. $His^{269}$ should serve as the fifth ligand of the heme-iron while $Asp^{380}$ should be its hydrogen-bonded partner. Other residues predicted to be involved in active site modulation and $H_2O_2$ binding are $Arg^{104}$, $Trp^{107}$, $His^{108}$, $Asn^{138}$, $Thr^{274}$ and $His^{275}$ (FIG. 4). According to Welinder's predictions (Welinder 1991), $Trp^{320}$ should be a key residue and be required for forming the protein-radical site (Sivaraja et al. 1989).

Figure 9:
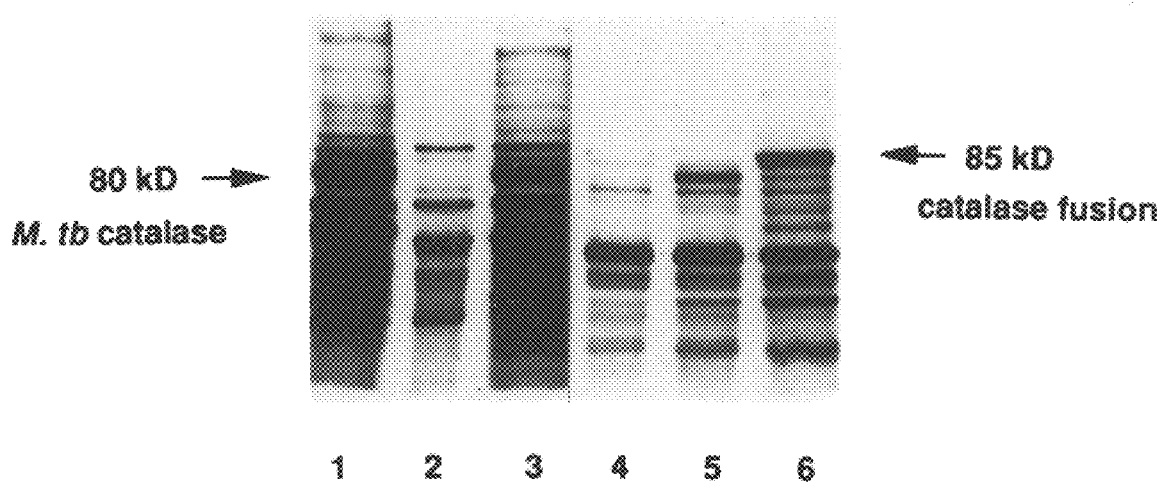
FIG. 9. Western blot analysis of *M. tuberculosis* KatG (SEQ ID NO:45) produced in different bacteria. Proteins were separated by SDS-polyacrylamide gel electrophoresis then subjected to immunoblotting, and detection with antiserum raised against BCG, as described in Zhang et al., 1991.

Antibody response to *M. tuberculosis* KatG (SEQ ID NO:48). To evaluate the possible value of KatG (SEQ ID NO:48) as an immunogen, Western blots were probed with anti-serum raised against *M. bovis* BCG in rabbits. As shown in FIG. 9, the 80 kD catalase-peroxidase is one of the prominent antigens recognized in cell-free extracts of *M. tuberculosis*, and *M. smegatis* expressing the cloned katG gene (SEQ ID NO:45) (lanes 1, 3). Likewise, on introduction of the gene into *E.coli* significant levels of catalase-peroxidase were produced a striking increase in expression was obtained from the lacZ'-katG gene fusion which directed the synthesis of an 85 kD fusion protein (FIG. 9, lane 6).

The aim of the present study was to determine the nucleotide sequence of the katG gene (SEQ ID NO:45) and to use the information obtained to try and understand how its product (SEQ ID NO:48) mediates the INH-susceptibility of *M. tuberculosis* and, possibly, to explain the apparent instability of the katg region of the genome (SEQ ID NO:45). Repetitive DNA is often a source of chromosomal rearrangements and analysis of the DNA sequence upstream of katG (SEQ ID NO:45) revealed two copies of a 700 bp direct repeat (SEQ ID NO:46–47). Since this element appears to be confined to this locus it is unlikely to serve as a target for an event, such as homologous recombination, which could lead to the deletion of the gene that is observed so frequently (Zhang et al. 1992, Nature; Zhang and Young 1993). Likewise, as a 70 kb stretch of the chromosome of *M. tuberculosis* H37Rv, encompassing katG (SEQ ID NO:45), is devoid of copies of IS6110 and IS1081, these insertion sequences do not appear to be likely sources of instability. Rather, the presence of a cluster of major polymorphic tandem repeats, MPTR (FIG. 5; Hermans et al. 1992) situated upstream of katG (SEQ ID NO:45), suggests that this might act as a recombinational hotspot. It may remove both the MPTR cluster and katg (SEQ ID NO:45) (Zhang and Young 1993). The availability of the sequence of the katG (SEQ ID NO:45) region will allow primers suitable for the polymerase chain reaction to be designed and thus facilitate studies aimed at both rapid detection of INH-resistance and understanding the molecular basis of chromosomal instability.

Figure 7A:
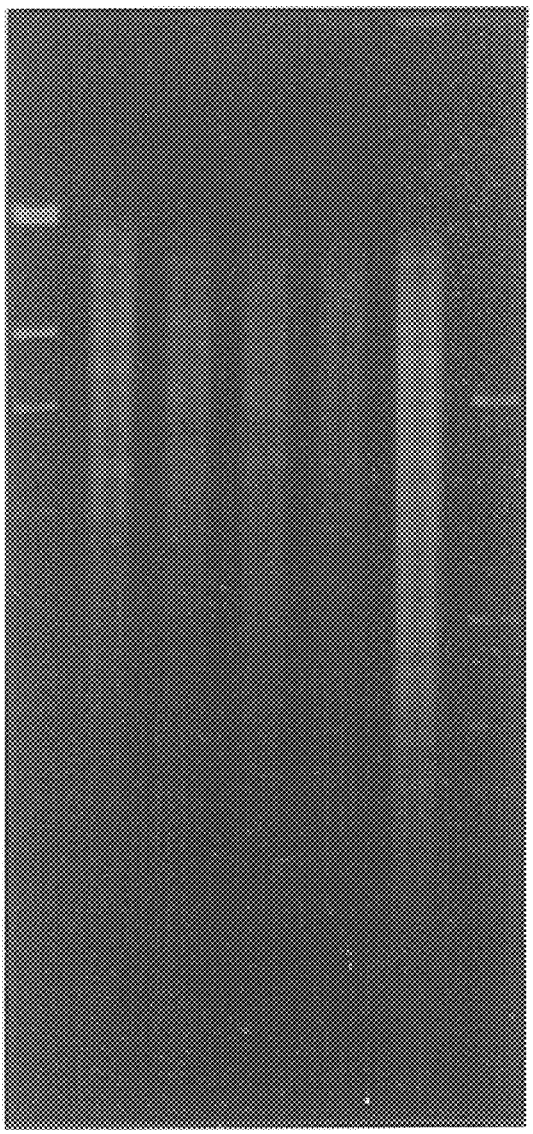
FIG. 7. Distribution of katG in mycobacteria. A. Samples of different bacterial DNAs (1.5 μg) were digested with RsrII, separated by agarose gel electrophoresis and stained with ethidium bromide; lanes 1 and 7, size markers; *M. leprae*; lane 3, *M. tuberculosis* H37Rv; lane 4, *M. gordonae*; lane 5, *M. szulaai*; lane 6, *M. avium*. B. Hybridization of the gel in A, after Southern blotting, with a katG specific probe.
Figure 7B:
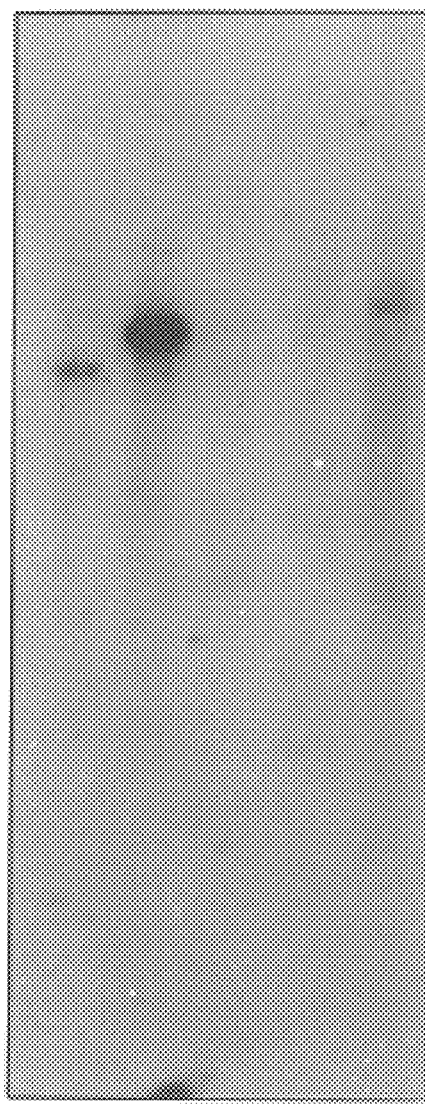

Perhaps the most intriguing feature of the *M. tuberculosis* catalase-peroxidase (SEQ ID NO:48) is its ability to mediate INH-susceptibility. In our current working hypothesis, the drug interacts with the enzyme and is converted by the peroxidase activity into a toxic derivative which acts at a second, as yet unknown, site (Zhang et al. 1992, *Nature*). Although horse radish peroxidase can effect this reaction (Pearson et al. 1988; Shoeb et al. 1985), and produce hydroxyl and organic free radicals, very few bacteria, including other mycobacteria, are sensitive to INH. This is intriguing as they contain genes homologous to katG (SEQ ID NO:45) (FIG. 7). One explanation for this could be provided by the fact that most bacterial contain two catalases, one of which is a broad spectrum enzyme endowed with peroxidase activity, and that the second catalase, by preferentially removing $H_2O_2$, limits the ability of the catalase-peroxidase to oxidize INH. As *M. tuberculosis* lacks the latter activity its KatG enzyme (SEQ ID NO:48) can convert INH to the lethal form without competition for the electron acceptor.

Alternatively, there may be some unique features of the *M. tuberculosis* enzyme which promote toxicity or favor the interaction with the drug. Examination of the primary structures of the bacterial catalase-peroxidases was not instructive in this respect as they all share extensive sequence identities and contain two motifs characteristic of the active sites of peroxidases. Furthermore, it has been shown recently that expression of the *E.coli* katG gene (SEQ ID NO:49) can partially restore INH-susceptibility to drug-resistant mutants of *M. tuberculosis* suggesting that the endogenous enzyme may not possess any drug-specific properties (Zhang et al. 1993). Sequence comparison with the cytochrome c peroxidase (SEQ ID NO:52) from yeast has provided important information about the structural and functional organization of the KatG protein (SEQ ID NO:48) and led to the identification of the putatively-important catalytic residues (FIG. 8).

Now that the complete sequence of katg (SEQ ID NO:48) is available it will be possible to test some of these hypotheses by site-directed mutagenesis and to overproduce the enzyme so that detailed analysis of the enzymatic reaction, and its products, can be performed in vitro. Likewise, it should be a relatively simple matter to isolate mutants that have retained enzymatic activity but are unable to bind or oxidize INH. Of particular interest is the repetitive structure of the enzyme and the prediction that the $NH_2$-terminal repeat contains the active site for peroxidases. This raises the possibility that katG (SEQ ID NO:45) genes, mutated, or truncated at the 3'-end, could arise. It is conceivable that their products, lacking the normal COOH-terminus which may be required for subunit-subunit interactions (Welinder 1991), would be unstable but still retain low enzyme activity. They would thus confer an intermediate level of INH-susceptibility, between that of $katG^+$ strains and mutants completely lacking the gene, as is often observed in clinical settings.

The invention may of course make use of a part of the above described 2.5 kb EcoRV-KpnI fragment, said part being nonetheless sufficiently long to provide for the selectivity of the in vitro detection of a *Mycobacterium tuberculosis* resistant to isoniazid. The invention also relates to a kit for detecting multidrug resistant variants of *M. tuberculosis* wherein the kit comprises:

(a) a container means containing a probe for the gene encoding drug resistance; and (b) a container means containing a control preparation of nucleic acid.

Needless to say that use can be made of any detection method alternative bringing into play the nucleodic sequence specific of nucleic acids of a Mycobacterium resistant to isoniazid, e.g. a method using an amplification technique and primers, whereby said primers may either be contained within said specific nucleotidic sequence, in order to provide for amplification fragments containing at least a part of the nucleotide sequence of the above mentioned probe, nonetheless sufficiently long to provide for the selectivity of the in vitro detection of a *Mycobacterium tuberculosis* resistant to isoniazid, and finally detecting a possible mutation in any of the amplified sequences.

A preferred process alternative (oligotyping) for the detection of resistance to the selected antibiotic comprises:

fragmenting the relevant gene or part thereof likely to carry the mutation into a plurality of fragments, such as by digestion of said relevant gene by selected restriction enzymes, hybridizing these fragments to complementary oligonucleotide probes, preferably a series of labelled probes recognizing under stringent conditions, all of the parts of the relevant gene of a corresponding control DNA of a strain non-resistant to the corresponding antibiotic, and relating the absence of hybridization of at least one of said oligonucleotide probes to any of the DNA fragments of the relevant gene of the mycobacterium under study as evidence of the presence of a mutation and, possibly, of a resistance to the corresponding antibiotic, particularly as compared to the runing of the test under the same conditions with the same oligonucleotides on the relevant gene(s) obtained from a strain (strains) not resistant to said antibiotic.

Another process alternative (SSCP analysis, i.e. analysis of Single Stranded Conformation Polymorphisms) comprises:

digesting the DNA to be analyzed, particularly of the relevant gene, amplifying the fragments obtained, e.g. by PCR, recovering the amplified fragments, and separating them from one another according to sizes, e.g. by causing them to migrate, for instance on an electrophoretic gel, comparing the sizes of the different fragments with those obtained from the DNA(S) of one or several control strains not resistant to the antibiotic, which had been subjected to a similar assay, and relating the polymorphism possibly detected to the existence of a mutation in the relevant gene, accordingly to a possible resistance to the corresponding antibiotic of the strain from which the DNA under study had been obtained.

Needless to say that any other method, including classical sequencing techniques, can resorted to for the achievement of the same purpose.

This method includes that known under the expression "oligotyping" for the detection of polymorphisms, reference is advantageously made to the method discloses by Orita et al. (reference was already made thereto herebefore) for the detection of polymorphisms based on the conformation of single strands.

The relevant gene in the case of resistance to isoniazid is of course the katG (SEQ ID NO:45) gene or a fragment thereof.

In the case of resistance to rifampicin, the relevant gene happens to be the rpoB, gene (SEQ ID NO:59) which codes for the βsub-unit of the RNA polymerases of said mycobacteria, or when only part of that gene is being used, preferably that part which includes the codons 400 to 450 of that rpoB gene.

Finally, in the case of resistance to steptomycin, the relevant gene contemplated is that of the rpsL gene (SEQ ID NO:63) that codes for the S12 protein of the small ribosome sub-unit or, when only part of said fragment is being used, preferably that part which includes the codon at the 43 position.

A preferred procedure, particularly in relation to the process alternative making use of PCR amplification is disclosed hereafter.

DNA is obtained from a biological sample (e.g. blood or sputum) after removal of the cellular debris and lysis of the bacterial cells with an appropriate lysis buffer. PCR application can be carried out by classical methods, using a pair of primers, whose sequences are respectively complementary to fragments of each of the strands of the DNA to be amplified.

The procedure may be run further as follows:

the amplification products (comprising e.g. from 100 to 300 nucleotides) are digested by means of suitable restriction endonuclease, the ADN strands obtained from the amplification medium are subjected to denaturation, the monostranded DNA strands are deposited on a neutral 5% polyacrylamid gel, the monostranded DNA strands are caused to migrate on said gel by means of electrophoresis, the DNA fragments that migrated on the polyacrilamid gel are transferred onto a nylon membrane according to a usual electrophoretic blotting technique and hybridized to labelled probes, for instance $^{32}$p labelled probes, and the migration distances of the DNA fragments subjected to analysis are compared to those obtained from controls obtained under the same conditions of amplification, digestion, denaturation electrophoresis and transfer onto a nylon membrane, whereby said DNA had been obtained from an identical bacterial strain yet sensitive to the antibiotic under study.

For the production of the PCR primers as well as of the polygonucleotides probes used in the above disclosed "oligotyping" procedures, use is advantageously made of those complementary to the rpoB gene (SEQ ID NO:59) of wild M. tuberculosis inserted in a plasmid deposited under number I-12167 at the CNCM on Sep. 15, 1992.

The invention also relates more particularly to the nucleotidic sequence of a fragment of rpsL gene (SEQ ID NO:63) of *Mycobacterium tuberculosis* coding for the S12 protein of the small ribosome sub-unit, as well as to the nucleotidic sequence of a mutated rpsL gene fragment deemed responsible of the resistance to streptomycin.

By amplification of that nucleotidic sequence, the nucleotide sequence of the full rpsL gene can be obtained.

Example

The sensitivity to rifampicin has been determined in mice as disclosed by Grosset et al. (and Int. J. Lepr. 57:607–614). The cells of *M. Leprae* were obtained from mouse paws according to classic procedures. All resistant strains were able to grow in mice which received daily doses of 20 mg/Kg of rifampicin, whereas sensitive strains were killed at low rifampicin concentrations, less than 2 mg/Kg.

Relevant regions of the rpoB gene of extracted DNA was initiated upon using two pairs of biotinylated primers, whose sequences appear in the following table 4.

Table 4

| Primer | Sequence | |
|---|---|---|
| Brpo22 | CAGGACGTCGAGGCGATCAC | (SEQ ID NO:30) |
| rpo23 | AACGACGACGTGGCCAGCGT | (SEQ ID NO:31) |
| Brpo24 | CAGACGGTGTTTATGGGCGA | (SEQ ID NO:32) |
| rpo25 | TCGGAGAAACCGAAACGCTC | (SEQ ID NO:33) |
| rpo32 | TCCTCGTCAGCGGTCAAGTA | (SEQ ID NO:34) |
| rpo33 | CTTCCCTATGATGACTG | (SEQ ID NO:35) |
| rpo34 | GGTGATCTGCTCACTGG | (SEQ ID NO:36) |
| rpo35 | GCCGCAGACGCTGATCA | (SEQ ID NO:37) |
| rpo36 | TTGACCGCTGACGAGGA | (SEQ ID NO:38) |
| rpo37 | GCCAGCGTCGATGGCCG | (SEQ ID NO:39) |

Upon using conventional techniques, amplification products comprising 310 and 710 bp were respectively obtained as shown in FIG. 1. The localization of the sequences of the different primers used in the table is also indicated on FIG. 10.

The DNAs obtained have been sequenced on the basis of the rpoB sequence of isolates sensitive to rifampicin (SEQ ID NO:59). A plasmid containing the sequence of that gene has been deposited at CNCM on Sep. 15, 1992 under number I-1266. Biotinylated PCR products were concentrated from the PCR reaction mixtures by contacting with streptavidin coated beads under agitation. The biotinylated strands attached to the beads were then recovered and sequenced. The sequences obtained were compared to the sequence of the rpoB gene of a wild type (SEQ ID NO:59) stain. Significant results were obtained as a result of sequencing of the wild gene (SEQ ID NO:59) (of a mycobacterium sensitive to rifampicin) and of corresponding sequences of the B-sub-unit of four mutant strains resistant to rifampicin (FIG. 11).

Results were obtained starting from 102 strands obtained from patients infected with *M. tuberculosis.* Among this 102 strands 53 were sensitive to rifampicin and 49 resistant to rifampicin. The mutation was localized in the region 400–450 in 43 of the mutants and among the latter, the mutation occured in the region of $^{425}$Ser into leu.

Example of Detection of the Resistance of Mycobacteria to Streptomycin

The culture of *M. tuberculosis* strains and the test of their sensitivity to streptomycin have been carried out by the method of proportions on a Löwenstein-Ierva medium (Laboratory Method for Clinical Mycobacteriology—Hugo David —Véronique Lévy Frébault, M. F. Thorel, published by Institut Pasteur).

The nucleotide sequence of the rpsL gene (SEQ ID NO:61) of *M. Leprae* led, by sequence analogy, to the construction of two primers, ML51 (CCCACCATTCAGCAGCTGGT) (SEQ ID NO:40) et ML52 (GTCGAGCGAACCGCGAATGA) (SEQ ID NO:41) surounding regions including putative mutation sites liable of being responsible for the streptomycin resistance and suitable for the PCR reaction. The DNA of the used *M. tuberculosis* used as a matrix has enabled one to obtain a rpsL fragment of 306 pb (SEQ ID NO:63). The nucleotide sequence of the sequenced fragments exhibited 28 differences with that of *M. Leprae*.

The rpsL genes or 43 strands of *M. tuberculosis*, among which 28 were resistant, have been amplified both by PCR and the SSCP technique.

DNA was extracted from 200 µl aliquots of *M. tuberculosis* samples (in average $10^4$ to $10^5$ bacteria) covered by 100µl of mineral oil by a congelation-decongelation technique (Woods and Cole, 1989 FEBS. Microbiol. Lett, 65:305–308).

After electrophoresis of the DNA strands tested a mutation was shown in 16 of the mutants. In order to establish the nature of the mutation in the 16 strands under consideration, the corresponding rpsL gene fragments were amplified by PCR using the ML51 (SEQ ID NO:40) and the ML52 (SEQ ID NO:41) primers and their respective nucleotide sequences were determined.

The sequences obtained were compared to the sequence of the wild type rpsL gene (SEQ ID NO:65). The single difference was found with the wild sequence ; codon 43, AAG, was mutated into AGG and, consequently, the lys-42 aminoacid was replaced by Arg.

The invention relates also to the "mutated" DNA fragments. They can in turn be used as hybridization probes for use for the dectection in suitable hybridization procedures and for the detection of similar mutation in DNA extracted from a *M. tuberbulosis* strain suspected to include resistance to any one of the above illustrated antibiotics.

The invention further relates to kits for the resistance of mycobacteriae to isoniazid, rifampicin or analogues thereof, and streptomycin.

The invention further relates to a kit for the in vitro diagnostic of the resistance of a bacteria of a mycobacterium genus to isoniazid, characterized in that it comprises: means for carrying out for a genic amplification of the DNA of the katG gene (SEQ ID NO:45) or of a fragment thereof, means to bring into evidence one or several mutations on the amplification products so obtained, a preparation of control DNA of a katG gene (SEQ ID NO:45) of a strain of said bacteria sensitive to isoniazid or of a fragment thereof, optionally, a control preparation of a DNA of the katG gene (SEQ ID NO:45) of an isoniazid-resistant mycobacterium strain.

The invention further relates to a kit for the in vitro diagnostic of the resistance of a bacteria of a mycobacterium genus to rifampicin or its analogues, characterized in that it comprises:

means for carrying out for a genic amplification of the DNA of the rpoB gene (SEQ ID NO:59) or of the β-sub-unit of the RNA polymerase (SEQ ID NO:60) of said mycobacteria, or of a fragment thereof, means to bring into evidence one or several mutations on the amplification products so obtained, a preparation of control DNA of a rpoB gene coding for the β-sub-unit of the RNA polymerase of a strain of said bacteria sensitive to rifampicin or of a fragment thereof, optionally, a control preparation of a DNA of the rpoB gene (SEQ ID NO:59) of an isoniazid-resistant mycobacterium strain.

Similarly, the invention pertains to a kit for the in vitro diagnostics of the resistance of the *M. tuberculosis* to streptomycin, characterized in that it includes:

means for carrying out a genic amplification of the rpsL gene (SEQ ID NO:63) coding for the S12 protein of the small ribosome subunit, or fragment thereof, means which enable the bringing to evidence of one or several mutations on the amplification products obtained, a control preparation of a DNA sequence of the rose gene (SEQ ID NO:65) coding for the S12 protein of the small sub-unit of the ribosome (SEQ ID NO:66) of a *M. tuberculosis* strain sensitive to streptomycin, and optionally, a control preparation of a DNA sequence of a rpsL gene (SEQ ID NO:63) coding for the S12 protein of the small sub-unit of the ribosome (SEQ ID NO:64) of a strain of *M. tuberculosis* resistant to streptomycin.

REFERENCES CITED IN THE SPECIFICATION

Altschul, S., Gish, W., Miller, W., Myers, E., and Lipman, D. (1990). A basic local alignment search tool. *Proc. Natl. Acad. Sci. USA* 215:403–410.

Bekierkunst, A. & Bricker, A. (1967). Studies on the mode of action of isoniazid on mycobacteria. *Arch. Biochem. Biophys.* 122:385–392.

Biggin, M. D., Gibson T. J., and Hong G. F. (1983). Buffer gradient gels and $^{35}$S-label as an aid to rapid DNA sequence determination. *Proc. Natl. Acad. Sci. USA* 80:3963–3965.

Bairoch, A., (1992). Prosite: a dictionary of sites and patterns in proteins. *Nucleic Acids Res.* 20:2013–2018.

C.D.C. Outbreak of multidrug-resistant tuberculosis—Texas, California, and Pennsylvania. MMWR 1990, 39:369–372.

C.D.C. Nosocomial transmission of multidrug-resistant tuberculosis among HIV-infected persons—Florida and New York 1988–1991. MMWR 1991(a) 40:585–591.

C.D.C. Transmission of multidrug-resistant tuberculosis from an HIV-positive client in a residential substance abuse treatment facility. Michigan. MMWR 1991(b), 40:129–131.

Chaisson, R. E., Schecter, G. F., Theuer, C. P., Rutherford, G. W., Echenberg, D. F., Hopewell, P. C. (1987). Tuberculosis in patients with the acquired immunodeficiency syndrome. *Am. Rev. Respir. Dis.,* 23:56–74.

Collins, D. M., and Stephens, D. M. (1991). Identification of an insertion sequence, 1S1081, in *Mycobacterium bovis*. *FEMS Microbiol. Lett.* 83:11–16.

Daley, C. L., Small, P. M., Schecter, G. F., Schoolnik, G. K., McAdam, R. A., Jacobs, W. R., and Hopewell, P. C. (1992). An outbreak of tuberculosis with accelerated progression among persons infected with the human immunodeficiency virus. An analysis using restriction-fragment-length-polymorphism. *N. Encl. J. Med.,* 326:231–235.

Devereux, J., Haeberli, P. and Smithies, 0. (1984) A comprehensive set of sequence analysis programs for the VAX. *Nucl. Acids Res.* 12:387–395.

Eiglmeier, K., Honore, N., and Cole, S. T. (1991). Towards the integration of foreign DNA into the chromosome of *Mycobacterium leprae*. *Research in Microbiology*, 142:617–622.

Finzel, B. C., Poulos, T. L. and Kraut, J. (1984). Crystal structure of yeast cytochrome C peroxidase at 1.7 Å resolution. *J. Biol. Chem.* 259:13027–13036.

Garnier, T., and Cole, S. T., (1986). Characterization of a bacteriocinogenic plasmid from *Clostridium perfringens* and molecular genetic analysis of the bacteriocin-encoding gene. *J. Bacteriol.,* 168:1189–1196.

Gayathri Devi, B., Shaila, M. S., Ramakrishnan, T., and Gopinathan, K. P. (1975). The purification and properties of peroxidase in *Mycobacterium tuberculosis* H37RV and its possible role in the mechanism of action of isonicotinic acid hydrazide. *Biochem. J.,* 149:187–197.

Hermans, P. W. M., van Soolingen, D. and van Embden, J. D. A. (1992). Characterization of a major polymorphic tandem repeat in *Mycobacterium tuberculosis* and its potential use in the epidemiology of *Mycobacterium kansasii* and *Mycobacterium Agordonae. J. Bacteriol.* 174:4157–4165.

Heym, B. and Cole, S. T. (1992). Isolation and characterization of isoniazid-resistant mutants of *Mycobacterium smegmatis* and *M. aurum. Res. Microbiol.,* submitted.

Jackett, P. S., Aber, V. and Lowrie, D. (1978). *J. Gen Microbiol.,* 104:37–45.

Kubica, G. P., Jones Jr., W. D., Abbott, V. D., Beam, R. E., Kilburn, J. O., and Cater Jr., J. C. (1966). Differential identification of mycobacteria. I. Tests on catalase activity. *Am. Rev. Resp. Dis.,* 94:400–405.

Kwok et al., S., *J. Virol.* 61:1690–1694 (1987). Multidrug resistance results from the accumulation of mutations in the genes for distinct drug targets.

Laemmli, U.K., (1970). Cleavage of structural proteins during the assembly of the head of bacteriophage-T4. Nature (London) 227:680–685.

Loewen, P. C., and Stauffer, G. V. (1990). Nucleotide sequence of katG of Salmonella typhimurium LT2 and characterization of its product, hydroperoxidase I. *Mol. Gen. Genet.* 224:147–151.

Loprasert, S., Negoro, S. and Okada, H. (1988). Thermostable peroxidase from *Bacillus stearothermorhilus. J. Gen. Microbiol.,* 134:1971–1976.

Loprasert, S., Negoro, S., and Okada, H. (1989). Cloning, nucleotide sequence, and expression in *Escherichia coli* of the *Bacillus stearotherrmophilus* peroxidase gene (perA). *J. Bacteriol.,* 171:4871–4875.

Maniatis, T., Sambrook, J., and Fritsch, E. F. (1989). Molecular cloning. A laboratory manual. Second Edition 1989. Cold Spring Harbor Laboratory Press.

Matsuo, K., Yamaguchi, R., Yamazaki, R. A., Tasaka, H. and Yamada, T. (1988). Cloning and expression of the *Mycobacterium bovis* BCG gene for extracellular α antigen. *J. Bacteriol.,* 170:3847–3854.

Middlebrook, G. (1954). Isoniazid-resistance and catalase activity of tubercle bacilli. *Am. Rev. Tuberc.,* 69:471–472.

Middlebrook, G., Cohn, M. L., and Schaefer, W. B. (1954).—Studies on isoniazid and tubercle bacilli. III. The isolation, drug-susceptibility, and catalase-testing of tubercle bacilli from isoniazid-treated patients. *Am. Rev. Tuberc.,* 70:852–872.

Mitchison, D. A., Selkon, J. B. and Lloyd, S. (1963). *J. Path. Bact.* 86:377–386.

Mulvey, M. R., Sorby PA, Triggs-Raine BL and Loewen PC. *Gene* 73:337–345 (1988).

Orita, M., Iwahana, I., Kanazawa, H., Itayashi, K., and Sekiya, J. (1989). *PNAS* 86:2766–2770.

Pearson, W., and Lipman, D. (1988). Improved tools for biological sequence comparisons. *Proc. Natl. Acad. Sic. USA.* 85:2444–2448.

Quemard, A., Lacave, C., and Laneelle, G. (1991). Isoniazid inhibition of mycolic acid synthesis by cell extracts of sensitive and resistant strains of *Mycobacterium aurum. Antimicrob. Ac. Chem.,* 35:1035–1039.

Saiki et al., R. K., *Bio/Technology* 3:1008–1012 (1985).

Shoeb, H. A., Bowman B. U. J., Ottolenghi, A. C., and Merola, A. J. (1985). Peroxidase-mediated oxidation of isoniazid. *Antimicrobial Agents and Chemotherapy,* 27:399–403.

Shoeb, H. A., Bowman, B. U. J., Ottolenghi, A. C., and Merola, A. S. (1985). Evidence for the generation of active oxygen by isoniazid treatment of extracts of *Mycobacterium tuberculosis* H37Ra. *Antimicrobial Agents and Chemotherapy,* 27:404–407.

Sivaraja, M., Goodin, D. B., Smith, M., and Hoffman, B. M., (1989). Identification by ENDOR of $Trp^{191}$ as the free-radical site in cytochrome c peroxidase Compound Es. *Science,* 245:738–740.

Snapper, S. B., Lugosi, L., Jekkel, A., Melton, R. E., Kieser, T., Bloom, B. R., and Jacobs, W. R. (1988). Lysogeny and transformation in mycobacteria: stable expression of foreign genes. *Proc. Natl. Acad. Sci. USA,* 85:6987–6991.

Snapper, S. B., Melton, R. E., Mustafa, S., Kieser, T., and Jacobs, W. R. (1990). Isolation and characterization of efficient plasmid transformation mutants of *Mycobacterium smegmatis. Mol. Microbiol.,* 4:1911–1919.

Snider, D. (1989). *Rev. Inf. Dis.,* S335.

Snider Jr., D. E. and Roper, W. L. (1992). The new tuberculosis. *The New England Journal of Medicine,* 326:703–705.

Sriprakash, K. S. and Ramakrishnan, T. (1970). Isoniazid-resistant mutants of *Mycobacterium tuberculosis* H37Rv: Uptake of isoniazid and the properties of NADase inhibitor. *J. Gen. Microbiol.,* 60:125–132.

Staden, R. (1987). Computer handling of sequence projects. In Nucleic acid and protein sequence analysis: A practical approach. Bishop, M. J. and Rawlings, C. J. (eds.) Oxford: IRL Press, pp. 173–217.

Thierry, D., Brisson-Noël, A., Vincent-Levy-Frebault, V., Nguyen, S., Guesdon, J., and Gicquel, B. (1990). Characterization of a *Mycobacterium tuberculosis* insertion sequence, IS6110, and its application in diagnosis. *S. Clin. Microbiol.,* 28:2668–2673.

Thierry, D., Cave, M. D., Eisenach, K. D., Crawford, S. T., Bates, S. H., Gicquel, B., and Guesdon, J. L. (1990). IS6110, an IS-like element of *Mycobacterium tuberculosis* complex. *Nucleic Acids Res.,* 18:188.

Triggs-Raine, B. L., Doble, B. W., Mulvey, M. R., Sorby, P. A., and Loewen, P. C. (1988). Nucleotide sequence of kaqG, encoding catalase HPI of *Escherichia coli. J. Bacteriol.,* 170:4415–4419.

Wayne, L. G. and Diaz, G. A. (1986). *Analyt. Biochem.* 157:89–92.

Welinder, K. G. (1991). Bacterial catalase-peroxidases are gene duplicated members of the plant peroxidase superfamily. *Biochim. Biophys. Acta* 1080:215–220.

Winder, F. and Collins, P. (1968). The effect of isoniazid on nicotinamide nucleotide levels in *Mycobacterium bovis,* strain BCG. *Amer. Rev. Respir. Dis.,* 97:719–720.

Winder, F. and Collins, P. (1969). The effect of isoniazid on nicotinamide nucleotide concentrations in tubercle bacilli. *Amer. Rev. Respir. Dis.,* 100:101–103.

Winder, F. and Collins, P. (1968). Inhibition by isoniazid of synthesis of mycolic acids in *Mycobacterium tuberculosis, J. Gen. Microbiol.,* 63:41–48.

Youatt, J. (1969). A review of the action of isoniazid. *Am. Rev. Respir. Dis.,* 99:729–749.

Zhang, Y., Garbe, T., and Young, D. (1993). Transformation with katG restores isoniazid-sensitivity in *Mycobacterium tuberculosis* isolates resistant to a range of drug concentrations. *Mol. Microbiol.,* submitted.

Zhang, Y., and Young, D. B. (1993) Characterization of a variable genetic element from the katG region of *Mycobacterium tuberculosis*—in preparation.

Zhang, Y., Lathigra, R., Garbe, T., Catty, D., and Young, D. (1991) Genetic analysis of superoxide dismutase, the 23 kilodalton antigen of *Mycobacterium tuberculosis. Mol. Microbiol.,* 5:381–391.

Zhang, Y., Heym, B., Allen, B., Young, D., and Cole, S. T. (1992). The catalase-peroxidase gene and isoniazid resistance of *Mycobacterium tuberculosis. Nature.* 358:591–593.

Zhang, Y., Garcia, M. J., Lathigra, R., Allen, B., Moreno, C., van Embden, D. A., and Young, D. (1992). Alterations in the superoxide dismutase gene of an isoniazid-resistant strain of *Mycobacterium tuberculosis. Infect. Immun.,* 60:2160–2165.

SEQUENCE LISTING (1) GENERAL INFORMATION:

(iii) NUMBER OF SEQUENCES: 66

(2) INFORMATION FOR SEQ ID NO:1:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

TTCATCCGCA TGGCCTGGCA CGGCGCGGGC ACCTACCGC      39

(2) INFORMATION FOR SEQ ID NO:2:

(i) SEQUENCE CHARACTERISTICS:
      (A) LENGTH: 37 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Ala Pro Leu Asn Ser Trp Pro Asp Asn Ala Ser Leu Asp Lys Ala Arg
1          5                 10              15

Arg Leu Leu Trp Pro Ser Lys Lys Lys Tyr Gly Lys Lys Leu Ser Trp
         20               25             30

Ala Asp Leu Ile Val
     35

(2) INFORMATION FOR SEQ ID NO:3:

(i) SEQUENCE CHARACTERISTICS:
      (A) LENGTH: 37 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Ala Pro Leu Asn Ser Trp Pro Asp Asn Val Ser Leu Asp Lys Ala Arg
1          5                 10              15

Arg Leu Leu Trp Pro Ile Lys Gln Lys Tyr Gly Gln Lys Ile Ser Trp
         20               25             30

Ala Asp Leu Phe Ile
     35

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Pro Leu Asn Ser Trp Pro Asp Asn Ala Asn Leu Asp Lys Ala Arg
1               5                   10                  15

Arg Cys Leu Gly Arg Ser Lys Arg Asn Thr Gly Thr Lys Ser Leu Gly
            20                  25                  30

Pro Ile Cys Ser
     35

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCGGGGTTAT CGCCGATG                                                18

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCCCTCGACG GGGTATTTC                                               19

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AACGGCTGTC CCGTCGTG                                                18

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear

```
        (ii) MOLECULE TYPE: DNA (genomic)

(xi) SEQUENCE DESCRIPTION: SEQ ID NO:8:

GTCGTGGATG CGGTAGGTG                                                    19

(2) INFORMATION FOR SEQ ID NO:9:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

TCGACTTGAC GCCCTGACG                                                    19

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

CAGGTCCGCC CATGACAG                                                     18

(2) INFORMATION FOR SEQ ID NO:11:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CCACAACGCC AGCTTCGAC                                                    19

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GGTTCACGTA GATCAGCCCC                                                   20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:
```

GCAGATGGGG CTGATCTACG                                                20

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

ACCTCGATGC CGCTGGTG                                                  18

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCTGGAGCAG ATGGGCTTG                                                 19

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

ATCCACCCGC AGCGAGAG                                                  18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GCCACTGACC TCTCGCTG                                                  18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGCCCATGCG GTCGAAAC                                                  18

(2) INFORMATION FOR SEQ ID NO:19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

GCGAAGCAGA TTGCCAGCC                                                    19

(2) INFORMATION FOR SEQ ID NO:20:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

ACAGCCACCG AGCACGAC                                                     18

(2) INFORMATION FOR SEQ ID NO:21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

CAAACTGTCC TTCGCCGACC                                                   20

(2) INFORMATION FOR SEQ ID NO:22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

CACCTACCAG CACCGTCATC                                                   20

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

TGCTCGACAA CGCGAACCTG                                                   20

(2) INFORMATION FOR SEQ ID NO:24:

(i) SEQUENCE CHARACTERISTICS:
            (A) LENGTH: 20 base pairs
            (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:24:

TCCGAGTTGG ACCCGAAGAC                                                        20

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

TACCAGGGCA AGGATGGCAG                                                        20

(2) INFORMATION FOR SEQ ID NO:26:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

GCAAACACCA GCACCCCG                                                          18

(2) INFORMATION FOR SEQ ID NO:27:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: one-of(9, 10)
            (D) OTHER INFORMATION: /note= "Xaa=unknown."

(xi) SEQUENCE DESCRIPTION: SEQ ID NO:27:

Asp Glu Thr Leu Ile Val Met Thr Xaa Xaa Leu Ile Val Met Leu Ile
1               5                   10                  15

Val Met Ser Thr Ala Gly Ser Ala Gly Leu Ile Val Met Ser Thr Ala
            20                  25                  30

Gly His Ser Thr Ala Leu Ile Val Met Phe Tyr
            35                  40

(2) INFORMATION FOR SEQ ID NO:28:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site (B) LOCATION: one-of(5, 6, 7, 19, 23)
        (D) OTHER INFORMATION: /note= "Xaa=unknown."

(xi) SEQUENCE DESCRIPTION: SEQ ID NO:28:

Ser Gly Ala Thr Xaa Xaa Xaa Leu Ile Val Met Ala Arg Leu Ile Val
1               5                   10                  15

Met Ala Xaa Phe Trp His Xaa Ser Ala Cys
            20                  25

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: one-of(2, 3, 4, 5)
        (D) OTHER INFORMATION: /note= "Xaa=unknown."

(xi) SEQUENCE DESCRIPTION: SEQ ID NO:29:

Gly Xaa Xaa Xaa Xaa Gly Lys Thr
1               5

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CAGGACGTCG AGGCGATCAC                                            20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

AACGACGACG TGGCCAGCGT                                            20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CAGACGGTGT TTATGGGCGA                                            20

(2) INFORMATION FOR SEQ ID NO:33:

```
        (i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

TCGGAGAAAC CGAAACGCTC                                             20

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

TCCTCGTCAG CGGTCAAGTA                                             20

(2) INFORMATION FOR SEQ ID NO:35:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

CTTCCCTATG ATGACTG                                                17

(2) INFORMATION FOR SEQ ID NO:36:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

GGTGATCTGC TCACTGG                                                17

(2) INFORMATION FOR SEQ ID NO:37:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:37:

GCCGCAGACG CTGATCA                                                17

(2) INFORMATION FOR SEQ ID NO:38:

(i) SEQUENCE CHARACTERISTICS:
            (A) LENGTH: 17 base pairs
            (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:38:

TTGACCGCTG ACGAGGA                                                      17

(2) INFORMATION FOR SEQ ID NO:39:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

GCCAGCGTCG ATGGCCG                                                      17

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CCCACCATTC AGCAGCTGGT                                                   20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

GTCGAGCGAA CCGCGAATGA                                                   20

(2) INFORMATION FOR SEQ ID NO:42:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

ATGACCATGA TTACGCCAAG CTTGCATGCC TGCAGGTCGA CTCTAGAGGA TCCCCATCCG        60

ACACTTCGCG ATCACATCCG TGATCACAGC CCGATAACAC CAACTCCTGG AAGGAATGCT      120

GTGCCCGAGC AACACCCACC CATTACAGAA ACCACCACCG GAGCCGCTAG CAACGGCTGT      180

CCCGTCGTGG GTCATATGAA ATACCCCGTC GAGGGCGGCG GAAACCAGGA CTGGTGGCCC      240

AACCGGCTCA ATCTGAAGGT ACTGCACCAA AACCCGGCCG TCGCTGACCC GATGGGTGCG      300

GCGTTCGACT ATGCCGCGGA GGTCGCGACC AGTCGACTTG ACGCCCTGAC GCGGGACATC      360
```

(2) INFORMATION FOR SEQ ID NO:43:

(i) SEQUENCE CHARACTERISTICS:
       (A) LENGTH: 120 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:43:

```
Met Thr Met Ile Thr Pro Ser Leu His Ala Cys Arg Ser Thr Leu Glu
1               5                  10                  15

Asp Pro His Pro Thr Leu Arg Asp His Ile Arg Asp His Ser Pro Ile
            20                  25                  30

Thr Pro Thr Pro Gly Arg Asn Ala Met Pro Glu Gln His Pro Pro Ile
        35                  40                  45

Thr Glu Thr Thr Thr Gly Ala Ala Ser Asn Gly Cys Pro Val Val Gly
    50                  55                  60

His Met Lys Tyr Pro Val Glu Gly Gly Asn Gln Asp Trp Trp Pro
65                  70                  75                  80

Asn Arg Leu Asn Leu Lys Val Leu His Gln Asn Pro Ala Val Ala Asp
                85                  90                  95

Pro Met Gly Ala Ala Phe Asp Tyr Ala Ala Glu Val Ala Thr Ser Arg
            100                 105                 110

Leu Asp Ala Leu Thr Arg Asp Ile
        115                 120
```

(2) INFORMATION FOR SEQ ID NO:44:

(i) SEQUENCE CHARACTERISTICS:
       (A) LENGTH: 78 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:44:

```
Met Ser Thr Ser Asp Asp Ile His Asn Thr Thr Ala Thr Gly Lys Cys
1               5                  10                  15

Pro Phe His Gln Gly Gly His Asp Gln Ser Ala Gly Ala Gly Thr Thr
            20                  25                  30

Thr Arg Asp Trp Trp Pro Asn Gln Leu Arg Val Asp Leu Leu Asn Gln
        35                  40                  45

His Ser Asn Arg Ser Asn Pro Leu Gly Glu Asp Phe Asp Tyr Arg Lys
    50                  55                  60

Glu Phe Ser Lys Leu Asp Tyr Tyr Gly Leu Lys Lys Asp Leu
65                  70                  75
```

(2) INFORMATION FOR SEQ ID NO:45:

(i) SEQUENCE CHARACTERISTICS:
       (A) LENGTH: 4795 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:45:

GGTACCGTGA GGCGATGGGT GGCCCGGGGC CCGGCTGTCT GGTAAGCGCG GCCGCAAAAC    60

-continued

```
AGCTGTACTC TCGAATCCCA GTTAGTAACA ATGTGCTATG GAATCTCCAA TGACGAGCAC      120

ACTTCACCGA ACCCCATTAG CCACCGCGGG GCTGGCGCTC GTAGTGGCGC TGGGTGGCTG      180

CGGGGGCGGG GGCGGTGACA GTCGAGAGAC ACCGCCATAC GTGCCGAAAG CGACGACCGT      240

CGACGCAACA ACGCCGGCGC CGGCCGCCGA GCCACTGACG ATCGCCAGTC CCATGTTCGC      300

CGACGGCGCC CCGATCCCGG TGCAATTCAG CTGCAAGGGG GCCAACGTGG CCGCCACCGT      360

TGACGTGGTC GTCGCCCGCG GCGAGCGAAC TGGCACTCGT CGTCGATGAC CCCGACGCGG      420

TCGGCGGACT GTACGTGCAC TGGATCGTGA CCGGAATCGC CCCTGGCTCT GGCAGCACGG      480

CGGATGGTCA GACTCCTGCT GGTGGGCACA GCGTGCCGAA TTCTGGTGGT CGGCAAGGAT      540

ACTTCGGTCC ATGCCCGCCG GCGGGCACCG GGACACACCA CTACCGGTTT ACCCTCTACC      600

ACCTTCCTGT CGCGCTCCAG CTGCCACCGG GAGCCACGGG AGTCCAAGCG GCACAGGCGA      660

TAGCACAGGC CGCCAGCGAC AGGCCCGGCT CGTCGGCACA TTCGAAGGCT GACGCCGCGG      720

CATCCCTGGC GAGGTGGTCG AAACCCTGGC TTCTCCAATT GCGCCTGGCG ACAATGATCA      780

ATATGGAATC GACAGTGGCG CACGCATTTC ACCGGTTCGC ACTGGCCATC TTGGGGCTGG      840

CGCTCCCCGT GGCGCTAGTT GCCTACGGTG GCAACGGTGA CAGTCGAAAG GCGGCGGCCG      900

TGGCGCCGAA AGCAGCAGCG CTCGGTCGGA GTATGCCCGA AACGCCTACC GGCGATGTAC      960

TGACAATCAG CAGTCCGGCA TTCGCCGACG GTGCGCCGAT CCCGGAACAG TACACCTGCA     1020

AAGGAGCCAA TATCGCGGCC TCCGTTGACC TGGTCGGCGC CGTTTGGCGG CGCACTCGTT     1080

GTCGATGATC CGGACCACCT CGCGAACCTT ACGTCCATTG GATCGTGATC GGGATCGCCC     1140

CTGGTGCTGG CAGCAGCCGA TGGTGAGACT CCCGGTGGCG GAATCAGCCT GCCGAACTCC     1200

AGCGGTCAGC CCGCATACAC CGGCCCCTGC CCGCCGGCGG GCACCGGGAC ACACCACTAC     1260

CGGTTTACCC TCTACCACCT TCCTGCCGTG CCTCCACTCG CGGGACTGGC TGGGACACAA     1320

GCGGCGCGGG TGATCGCGCA GGCCGCCACC ATGCAGGCCC GGCTCATCGG AACATACGAA     1380

GGCTGATCCA CCCGCCATCC CACGATCCAG CGGCCCCGGG CGATCGGGTC CTAGCAGACG     1440

CCTGTCACGC TAGCCAAAGT CTTGACTGAT TCCAGAAAAG GGAGTCATAT TGTCTAGTGT     1500

GTCCTCTATA CCGGACTACG CCGAACAGCT CCGGACGGCC GACCTGCGCG TGACCCGACC     1560

GCGCGTCGCC GTCCTGGAAG CAGTGAATGC GCATCCACAC GCCGACACGG AAACGATTTT     1620

CGGTGCCGTG CGTTTTGCGC TGCCCGACGT ATCCGGCAAG CCGTGTACGA CGTGCTGCAT     1680

GCCCTGACCG CCGCGGGCTT GGTGCGAAAG ATCCAACCCT CGGGCTCCGT CGCGCGCTAC     1740

GAGTCCAGGG TCGGCGACAA CCACCATCAC ATCGTCTGCC GGTCTTGCGG GGTTATCGCC     1800

GATGTCGACT GTGCTGTTGG CGAGGCACCC TGTCTGACGG CCTCGGACCA TAACGGCTTC     1860

CTGTTGGACG AGGCGGAGGT CATCTACTGG GGTCTATGTC CTGATTGTTC GATATCCGAC     1920

ACTTCGCGAT CACATCCGTG ATCACAGCCC GATAACACCA ACTCCTGGAA GGAATGCTGT     1980

GCCCGAGCAA CACCCACCCA TTACAGAAAC CACCACCGGA GCCGCTAGCA ACGGCTGTCC     2040

CGTCGTGGGT CATATGAAAT ACCCCGTCGA GGGCGGCGGA AACCAGGACT GGTGGCCCAA     2100

CCGGCTCAAT CTGAAGGTAC TGCACCAAAA CCCGGCCGTC GCTGACCCGA TGGGTGCGGC     2160

GTTCGACTAT GCCGCGGAGG TCGCGACCAG TCGACTTGAC GCCCTGACGC GGGACATCGA     2220

GGAAGTGATG ACCACCTCGC AGCCGTGGTG GCCCGCCGAC TACGGCCACT ACGGGCCGCT     2280

GTTTATCCGG ATGGCGTGGC ACGCTGCCGG CACCTACCGG ATCACGACG GCCGCGGCGG     2340

CGCCGGGGGC GGCATGCAGC GGTTCGCGCC GCTTAACAGC TGGCCCGACA ACGCCAGCTT     2400
```

-continued

```
GGACAAGGCG CGCCGGCTGC TGTGGCCGGT CAAGAAGAAG TACGGCAAGA AGCTCTCATG    2460

GGCGGACCTG ATTGTTTTCG CCGGCAACCG CTGCGCTCGG AATCGATGGG CTTCAAGACG    2520

TTCGGGTTCG GCTTCGGGCG TCGACCAGTG GGAGACCGAT GAGGTCTATT GGGGCAAGGA    2580

AGCCACCTGG CTCGGCGATG ACGGTTACAG CGTAAGCGAT CTGGAGAACC CGCTGGCCGC    2640

GGTGCAGATG GGGCTGATCT ACGTGAACCC GGAGGCGCCG AACGGCAACC CGGACCCCAT    2700

GGCCGCGGCG GTCGACATTC GCGAGACGTT TCGGCGCATG GCCATGAACG ACGTCGAAAC    2760

AGCGGCGCTG ATCGTCGGCG GTCACACTTT CGGTAAGACC CATGGCGCCG GCCCGGCCGA    2820

TCTGGTCGGC CCCGAACCCG AGGCTGCTCC GCTGGAGCAG ATGGGCTTGG GCTGGAAGAG    2880

CTCGTATGGC ACCGGAACCG GTAAGGACGC GATCACCAGC GGCATCGAGG TCGTATGGAC    2940

GAACACCCCG ACGAAATGGG ACAACAGTTT CCTCGAGATC CTGTACGGCT ACGAGTGGGA    3000

GCTGACGAAG AGCCCTGCTG GCGCTTGGCA ATACACCGCC AAGGACGGCG CCGGTGCCGG    3060

CACCATCCCG GACCCGTTCG GCGGGCCAGG GCGCTCCCCG ACGATGCTGG CCACTGACCT    3120

CTCGCTGCGG GTGGATCCGA TCTATGAGCG GATCACGCGT CGCTGGCTGG AACACCCCGA    3180

GGAATTGGCC GACGAGTTCC GCAAGGCCTG GTACAAGCTG ATCCACCGAG ACATGGGTCC    3240

CGTTGCGAGA TACCTTGGGC CGCTGGTCCC CAAGCAGACC CTGCTGTGGC AGGATCCGGT    3300

CCCTGCGGTC AGCACGACCT CGTCGGCGAA GCAGATTGCC AGCCTTAAGA GCCAGATCCG    3360

GGCATCGGGA TTGACTGTCT CACAGCTAGT TTCGACCGCA TGGGCGGCGG CGTCGTCGTT    3420

CCGTGGTAGC GACAAGCGCG GCGGCGCCAA CGGTGGTCGC ATCCGCCTGC AGCCACAACT    3480

CGGGTGGGAG GTCAACGACC CCGACGGATC TGCGCAAGGT CATTCGCACC CTGAAGAGAT    3540

CCAGGAGTCA TTCACTCGGC GCGGGAACAT CAAAGTGTCC TTCGCCGACC TCGTCGTGCT    3600

CGGTGGCTGT GCGCCACTAG AGAAAGCAGC AAAGGCGGCT GGCCACAACA TCACGGTGCC    3660

CTTCACCCCG GGCCCGCACG ATGCGTCGCA GGAACAAACC GACGTGGAAT CCTTTGCCGT    3720

GCTGGAGCCC AAGGCAGATG GCTTCCGAAA CTACCTCGGA AAGGGCAACC GTTGCCGGCC    3780

GAGTACATCG CTGCTCGACA AGGCGAACCT GCTTACGCTC AGTGCCCCTG AGATGACGGT    3840

GCTGGTAGGT GGCCTGCGCG TCCTCGGCGC AAACTACAAG CGCTTACCGC TGGGCGTGTT    3900

CACCGAGGCC TCCGAGTCAC TGACCAACGA CTTCTTCGTG AACCTGCTCG ACATGGGTAT    3960

CACCTGGGAG CCCTCGCCAG CAGATGACGG GACCTACCAG GGCAAGGATG GCAGTGGCAA    4020

GGTGAAGTGG ACCGGCAGCC GCGTGGACCT GGTCTTCGGG TCCAACTCGG AGTTGCGGGC    4080

GCTTGTCGAG GTCTATGCGC CGATGACGCG GCAGGCGAAG TTCGTGACAG GATTCGTCGC    4140

TGCGTGGGAC AAGGTGATGA ACCTCGACAG GTTCGACGTG CGCTGATTCG GGTTGATCGG    4200

CCCTGCCCGC CGATCAACCA CAACCCGCCG CAGCACCCCG CGAGCTGACC GGCTCGCGGG    4260

GTGCTGGTGT TTGCCCGGCG CGATTTGTCA GACCCCGCGT GCATGGTGGT CGCACGGACG    4320

CACGAGACGG GGATGACGAG ACGGGATGAG GGAGAAAGGG CGCCGAAATG TGCTGGATGT    4380

GCGATCACCC GGAAGCCACC GCCGAGGAGT ACCTCGACGA GGTGTACGGG ATAATGCTCA    4440

TGCATGGCTG GGCGGTACAG CACGTGGAGT GCGAGCGACG GCCATTTGCC TACACGGTTG    4500

GTCTAACCCG GCGCGGCTTG CCCGAACTGG TGGTGACTGG CCTCTCGCCA CGACGTGGGC    4560

AGCGGTTGTT GAACATGCCG TCGAGGGCTC TGGTCGGTGA CTTGCTGACT CCCGGTATGT    4620

AGACCACCCT CAAAGCCGGC CCTCTTGTCG AAACGGTCCA GGCTACACAT CCGGACGCGC    4680

ATTTGTATTG TGCGATCGCC ATCTTTGCGC ACAAGGTGAC GGCCTTGCAG TTGGTGTGGG    4740

CCGACCGCGT GGTCGCTGGC CGTGGGCGGC GGACTTCGAC GAAGGTCGCG GTACC         4795
```

(2) INFORMATION FOR SEQ ID NO:46:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
TTCGAAGGCT GACGCCGCGG CATCCCTGGC GAGGTGGTCG AAACCCTGGC TTCTCCAATT    60
GCGCCTGGCG ACAATGATCA ATATGGAATC GACAGTGGCG CACGCATTTC ACCGGTTCGC   120
ACTGGCCATC TTGGGGCTGG CGCTCCCCGT GGCGCTAGTT GCCTACGGTG GCAACGGTGA   180
CAGTCGAAAG GCGGCGGCCG TGGCGCCGAA AGCAGCAGCG CTCGGTCGGA GTATGCCCGA   240
AACGCCTACC GGCGATGTAC TGACAATCAG CAGTCCGGCA TTCGCCGACG GTGCGCCGAT   300
CCCGGAACAG TACACCTGCA AAGGAGCCAA TATCGCGGCC TCCGTTGACC TGGTCGGCGC   360
CGTTTGGCGG CGCACTCGTT GTCGATGATC CGGACCACCT CGCGAACCTT ACGTCCATTG   420
GATCGTGATC GGGATCGCCC CTGGTGCTGG CAGCAGCCGA TGGTGAGACT CCCGGTGGCG   480
GAATCAGCCT GCCGAACTCC AGCGGTCAGC CCGCATACAC CGGCCCCTGC CCGCCGGCGG   540
GCACCGGGAC ACACCACTAC CGGTTTACCC TCTACCACCT TCCTGCCGTG CCTCCACTCG   600
CGGGACTGGC TGGGACACAA GCGGCGCGGG TGATCGCGCA GGCCGCCACC ATGCAGGCCC   660
GGCTCATCGG AACATACGAA GGCTGATCCA CCCGCCATCC                          700
```

(2) INFORMATION FOR SEQ ID NO:47:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

```
GGTACCGTGA GGCGATGGGT GGCCCGGGGC CCGGCTGTCT GGTAAGCGCG GCCGCAAAAC    60
AGCTGTACTC TCGAATCCCA GTTAGTAACA ATGTGCTATG GAATCTCCAA TGACGAGCAC   120
ACTTCACCGA ACCCCATTAG CCACCGCGGG GCTGGCGCTC GTAGTGGCGC TGGGTGGCTG   180
CGGGGGCGGG GGCGGTGACA GTCGAGAGAC ACCGCCATAC GTGCCGAAAG CGACGACCGT   240
CGACGCAACA ACGCCGGCGC CGGCCGCCGA GCCACTGACG ATCGCCAGTC CCATGTTCGC   300
CGACGGCGCC CCGATCCCGG TGCAATTCAG CTGCAAGGGG GCCAACGTGG CCGCCACCGT   360
TGACGTGGTC GTCGCCCGCG GCGAGCGAAC TGGCACTCGT CGTCGATGAC CCCGACGCGG   420
TCGGCGGACT GTACGTGCAC TGGATCGTGA CCGGAATCGC CCCTGGCTCT GGCAGCACGG   480
CGGATGGTCA GACTCCTGCT GGTGGGCACA GCGTGCCGAA TTCTGGTGGT CGGCAAGGAT   540
ACTTCGGTCC ATGCCCGCCG GCGGGCACCG GGACACACCA CTACCGGTTT ACCCTCTACC   600
ACCTTCCTGT CGCGATCCAG CTGCCACCGG GAGCCACGGG AGTCCAAGCG GCACAGGCGA   660
TAGCACAGGC CGCCAGCGAC AGGCCCGGCT CGTCGGCACA                          700
```

(2) INFORMATION FOR SEQ ID NO:48:

(i) SEQUENCE CHARACTERISTICS:

(A) LENGTH: 735 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:48:

```
Met Pro Glu Gln His Pro Pro Ile Thr Glu Thr Thr Thr Gly Ala Ala
1               5                   10                  15

Ser Asn Gly Cys Pro Val Val Gly His Met Lys Tyr Pro Val Glu Gly
            20                  25                  30

Gly Gly Asn Gln Asp Trp Trp Pro Asn Arg Leu Asn Leu Lys Val Leu
        35                  40                  45

His Gln Asn Pro Ala Val Ala Asp Pro Met Gly Ala Ala Phe Asp Tyr
    50                  55                  60

Ala Ala Glu Val Ala Thr Ser Arg Leu Asp Ala Leu Thr Arg Asp Ile
65                  70                  75                  80

Glu Glu Val Met Thr Thr Ser Gln Pro Trp Trp Pro Ala Asp Tyr Gly
                85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Gly Met Gln Arg
        115                 120                 125

Phe Ala Pro Leu Asn Ser Trp Pro Asp Asn Ala Ser Leu Asp Lys Ala
130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Arg Cys Ala Arg Asn Arg
                165                 170                 175

Trp Ala Ser Arg Arg Ser Gly Ser Ala Ser Gly Val Asp Gln Trp Glu
            180                 185                 190

Thr Asp Glu Val Tyr Trp Gly Lys Glu Ala Thr Trp Leu Gly Asp Asp
        195                 200                 205

Gly Tyr Ser Val Ser Asp Leu Glu Asn Pro Leu Ala Ala Val Gln Met
    210                 215                 220

Gly Leu Ile Tyr Val Asn Pro Glu Ala Pro Asn Gly Asn Pro Asp Pro
225                 230                 235                 240

Met Ala Ala Ala Val Asp Ile Arg Glu Thr Phe Arg Arg Met Ala Met
                245                 250                 255

Asn Asp Val Glu Thr Ala Ala Leu Ile Val Gly Gly His Thr Phe Gly
            260                 265                 270

Lys Thr His Gly Ala Gly Pro Ala Asp Leu Val Gly Pro Glu Pro Glu
        275                 280                 285

Ala Ala Pro Leu Glu Gln Met Gly Leu Gly Trp Lys Ser Ser Tyr Gly
    290                 295                 300

Thr Gly Thr Gly Lys Asp Ala Ile Thr Ser Gly Ile Glu Val Val Trp
305                 310                 315                 320

Thr Asn Thr Pro Thr Lys Trp Asp Asn Ser Phe Leu Glu Ile Leu Tyr
                325                 330                 335

Gly Tyr Glu Trp Glu Leu Thr Lys Ser Pro Ala Gly Ala Trp Gln Tyr
            340                 345                 350

Thr Ala Lys Asp Gly Ala Gly Ala Gly Thr Ile Pro Asp Pro Phe Gly
        355                 360                 365

Gly Pro Gly Arg Ser Pro Thr Met Leu Ala Thr Asp Leu Ser Leu Arg
```

-continued

```
                370                 375                 380
Val Asp Pro Ile Tyr Glu Arg Ile Thr Arg Arg Trp Leu Glu His Pro
385                 390                 395                 400

Glu Glu Leu Ala Asp Glu Phe Arg Lys Ala Trp Tyr Lys Leu Ile His
                405                 410                 415

Arg Asp Met Gly Pro Val Ala Arg Tyr Leu Gly Pro Leu Val Pro Lys
                420                 425                 430

Gln Thr Leu Leu Trp Gln Asp Pro Val Pro Ala Val Ser Thr Thr Ser
            435                 440                 445

Ser Ala Lys Gln Ile Ala Ser Leu Lys Ser Gln Ile Arg Ala Ser Gly
        450                 455                 460

Leu Thr Val Ser Gln Leu Val Ser Thr Ala Trp Ala Ala Ala Ser Ser
465                 470                 475                 480

Phe Arg Gly Ser Asp Lys Arg Gly Gly Ala Asn Gly Gly Arg Ile Arg
                485                 490                 495

Leu Gln Pro Gln Val Gly Trp Glu Val Asn Asp Pro Asp Gly Ser Ala
                500                 505                 510

Gln Gly His Ser His Pro Glu Glu Ile Gln Glu Ser Phe Thr Arg Arg
            515                 520                 525

Gly Asn Ile Lys Val Ser Phe Ala Asp Leu Val Val Leu Gly Gly Cys
        530                 535                 540

Ala Pro Leu Glu Lys Ala Ala Lys Ala Ala Gly His Asn Ile Thr Val
545                 550                 555                 560

Pro Phe Thr Pro Gly Pro His Asp Ala Ser Gln Glu Gln Thr Asp Val
                565                 570                 575

Glu Ser Phe Ala Val Leu Glu Pro Lys Ala Asp Gly Phe Arg Asn Tyr
            580                 585                 590

Leu Gly Lys Gly Asn Arg Cys Arg Pro Ser Thr Ser Leu Leu Asp Lys
        595                 600                 605

Ala Asn Leu Leu Thr Leu Ser Ala Pro Glu Met Thr Val Leu Val Gly
    610                 615                 620

Gly Leu Arg Val Leu Gly Ala Asn Tyr Lys Arg Leu Pro Leu Gly Val
625                 630                 635                 640

Phe Thr Glu Ala Ser Glu Ser Leu Thr Asn Asp Phe Phe Val Asn Leu
                645                 650                 655

Leu Asp Met Gly Ile Thr Trp Glu Pro Ser Pro Ala Asp Asp Gly Thr
            660                 665                 670

Tyr Gln Gly Lys Asp Gly Ser Gly Lys Val Lys Trp Thr Gly Ser Arg
        675                 680                 685

Val Asp Leu Val Phe Gly Ser Asn Ser Glu Leu Arg Ala Leu Val Glu
    690                 695                 700

Val Tyr Ala Pro Met Thr Arg Gln Ala Lys Phe Val Thr Gly Phe Val
705                 710                 715                 720

Ala Ala Trp Asp Lys Val Met Asn Leu Asp Arg Phe Asp Val Arg
                725                 730                 735

(2) INFORMATION FOR SEQ ID NO:49:

(i) SEQUENCE CHARACTERISTICS:
        (A) LENGTH: 726 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO:49:

```
Met Ser Thr Ser Asp Ile His Asn Thr Thr Ala Thr Gly Lys Cys
 1               5                  10                  15

Pro Phe His Gln Gly Gly His Asp Gln Ser Ala Gly Ala Gly Thr Thr
                 20                  25                  30

Thr Arg Asp Trp Trp Pro Asn Gln Leu Arg Val Asp Leu Leu Asn Gln
                 35                  40                  45

His Ser Asn Arg Ser Asn Pro Leu Gly Glu Asp Phe Asp Tyr Arg Lys
             50                  55                  60

Glu Phe Ser Lys Leu Asp Tyr Tyr Gly Leu Lys Lys Asp Leu Lys Ala
 65                  70                  75                  80

Leu Leu Thr Glu Ser Gln Pro Trp Trp Pro Ala Asp Trp Gly Ser Tyr
                 85                  90                  95

Ala Gly Leu Phe Ile Arg Met Ala Trp His Gly Ala Gly Thr Tyr Arg
                100                 105                 110

Ser Ile Asp Gly Arg Gly Gly Ala Gly Arg Gly Gln Gln Arg Phe Ala
                115                 120                 125

Pro Leu Asn Ser Trp Pro Asp Asn Val Ser Leu Asp Lys Ala Arg Arg
            130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
                180                 185                 190

Leu Asp Val Asn Trp Gly Asp Glu Lys Ala Trp Leu Thr His Arg His
            195                 200                 205

Pro Glu Ala Leu Ala Lys Ala Pro Leu Gly Ala Thr Glu Met Gly Leu
210                 215                 220

Ile Tyr Val Asn Pro Glu Gly Pro Asp His Ser Gly Glu Pro Leu Ser
225                 230                 235                 240

Ala Ala Ala Ala Ile Arg Ala Thr Phe Gly Asn Met Gly Met Asn Asp
                245                 250                 255

Glu Glu Thr Val Ala Leu Ile Ala Gly Gly His Thr Leu Gly Lys Thr
                260                 265                 270

His Gly Ala Gly Pro Thr Ser Asn Val Gly Pro Asp Pro Glu Ala Ala
            275                 280                 285

Pro Ile Glu Glu Gln Gly Leu Gly Trp Ala Ser Thr Tyr Gly Ser Gly
290                 295                 300

Val Gly Ala Asp Ala Ile Thr Ser Gly Leu Glu Val Val Trp Thr Gln
305                 310                 315                 320

Thr Pro Thr Gln Trp Ser Asn Tyr Phe Phe Glu Asn Leu Phe Lys Tyr
                325                 330                 335

Glu Trp Val Gln Thr Arg Ser Pro Ala Gly Ala Ile Gln Phe Glu Ala
                340                 345                 350

Val Asp Ala Pro Glu Ile Ile Pro Asp Pro Phe Asp Pro Ser Lys Lys
            355                 360                 365

Arg Lys Pro Thr Met Leu Val Thr Asp Leu Thr Leu Arg Phe Asp Pro
370                 375                 380

Glu Phe Glu Lys Ile Ser Arg Arg Phe Leu Asn Asp Pro Gln Ala Phe
385                 390                 395                 400

Asn Glu Ala Phe Ala Arg Ala Trp Phe Lys Leu Thr His Arg Asp Met
                405                 410                 415
```

Gly Pro Lys Ser Arg Tyr Ile Gly Pro Glu Val Pro Lys Glu Asp Leu
                420                 425                 430

Ile Trp Gln Asp Pro Leu Pro Gln Pro Ile Tyr Asn Pro Thr Glu Gln
            435                 440                 445

Asp Ile Ile Asp Leu Lys Phe Ala Ile Ala Asp Ser Gly Leu Ser Val
        450                 455                 460

Ser Glu Leu Val Ser Val Ala Trp Ala Ser Ala Ser Thr Phe Arg Gly
465                 470                 475                 480

Gly Asp Lys Arg Gly Gly Ala Asn Gly Ala Arg Leu Ala Leu Met Pro
                485                 490                 495

Gln Arg Asp Trp Asp Val Asn Ala Ala Ala Val Arg Ala Leu Pro Val
            500                 505                 510

Leu Glu Lys Ile Gln Lys Glu Ser Gly Lys Ala Ser Leu Ala Asp Ile
        515                 520                 525

Ile Val Leu Ala Gly Val Val Gly Val Glu Lys Ala Ala Ser Ala Ala
530                 535                 540

Gly Leu Ser Ile His Val Pro Phe Ala Pro Gly Arg Val Asp Ala Arg
545                 550                 555                 560

Gln Asp Gln Thr Asp Ile Glu Met Phe Glu Leu Leu Glu Pro Ile Ala
            565                 570                 575

Asp Gly Phe Arg Asn Tyr Arg Ala Arg Leu Asp Val Ser Thr Thr Glu
            580                 585                 590

Ser Leu Leu Ile Asp Lys Ala Gln Gln Leu Thr Leu Thr Ala Pro Glu
        595                 600                 605

Met Thr Ala Leu Val Gly Gly Met Arg Val Leu Gly Gly Asn Phe Asp
        610                 615                 620

Gly Ser Lys Asn Gly Val Phe Thr Asp Arg Val Gly Val Leu Ser Asn
625                 630                 635                 640

Asp Phe Phe Val Asn Leu Leu Asp Met Arg Tyr Glu Trp Lys Ala Thr
                645                 650                 655

Asp Glu Ser Lys Glu Leu Phe Glu Gly Arg Asp Arg Glu Thr Gly Glu
            660                 665                 670

Val Lys Phe Thr Ala Ser Arg Ala Asp Leu Val Phe Gly Ser Asn Ser
        675                 680                 685

Val Leu Arg Ala Val Ala Glu Val Tyr Ala Ser Ser Asp Ala His Glu
690                 695                 700

Lys Phe Val Lys Asp Phe Val Ala Ala Trp Val Lys Val Met Asn Leu
705                 710                 715                 720

Asp Arg Phe Asp Leu Leu
                725

(2) INFORMATION FOR SEQ ID NO:50:

(i) SEQUENCE CHARACTERISTICS:
        (A) LENGTH: 729 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

Met Ser Thr Thr Asp Asp Thr His Asn Thr Leu Ser Thr Gly Lys Cys
1               5                   10                  15

Pro Phe His Gln Gly Gly His Asp Arg Ser Ala Gly Ala Gly Thr Ala
                20                  25                  30

```
Ser Arg Asp Trp Trp Pro Asn Gln Leu Arg Val Asp Leu Leu Asn Gln
     35                  40                  45

His Ser Asn Arg Ser Asn Pro Leu Gly Glu Asp Phe Asp Tyr Arg Lys
 50                  55                  60

Glu Phe Ser Lys Leu Asp Tyr Tyr Ser Ala Leu Lys Gly Asp Leu Lys
65                  70                  75                  80

Ala Leu Leu Thr Asp Ser Gln Pro Trp Trp Pro Ala Asp Trp Gly Ser
             85                  90                  95

Tyr Val Gly Leu Phe Ile Arg Met Ala Trp His Gly Ala Gly Thr Tyr
            100                 105                 110

Arg Ser Ile Asp Gly Arg Gly Gly Ala Gly Arg Gly Gln Gln Arg Phe
            115                 120                 125

Ala Pro Leu Asn Ser Trp Pro Asp Thr Val Ser Leu Asp Lys Ala Arg
130                 135                 140

Arg Leu Leu Trp Pro Ile Lys Gln Lys Tyr Gly Gln Lys Ile Ser Trp
145                 150                 155                 160

Ala Asp Leu Phe Ile Leu Ala Gly Asn Val Ala Leu Glu Asn Ser Gly
            165                 170                 175

Phe Arg Thr Phe Gly Phe Gly Ala Gly Arg Glu Asp Val Trp Glu Pro
            180                 185                 190

Asp Leu Asp Val Asn Trp Gly Asp Glu Lys Ala Trp Leu Thr His Arg
            195                 200                 205

His Pro Glu Ala Leu Ala Lys Ala Pro Leu Gly Ala Thr Glu Met Asp
            210                 215                 220

Leu Ile Tyr Val Thr Pro Glu Gly Pro Asn His Ser Gly Glu Pro Leu
225                 230                 235                 240

Ser Ala Ala Ala Ile Arg Ala Thr Phe Gly Asn Met Gly Met Asn
            245                 250                 255

Asp Glu Glu Thr Val Ala Leu Ile Ala Gly Gly His Thr Leu Gly Lys
            260                 265                 270

Thr His Gly Pro Ala Ala Ser His Val Gly Ala Asp Pro Glu Ala
            275                 280                 285

Ala Pro Ile Glu Ala Gln Gly Leu Gly Trp Ala Ser Ser Tyr Gly Ser
290                 295                 300

Gly Val Gly Ala Asp Ala Ile Thr Ser Gly Leu Glu Val Val Trp Thr
305                 310                 315                 320

Gln Thr Pro Thr Gln Trp Ser Asn Tyr Phe Phe Glu Asn Leu Phe Lys
            325                 330                 335

Tyr Glu Trp Val Gln Thr Arg Ser Pro Ala Gly Ala Ile Gln Phe Glu
            340                 345                 350

Ala Val Asp Ala Pro Asp Ile Ile Pro Asp Pro Phe Asp Pro Ser Lys
            355                 360                 365

Lys Arg Xaa Xaa Lys Pro Thr Met Leu Val Thr Asp Leu Thr Leu Arg
            370                 375                 380

Phe Asp Pro Glu Phe Glu Lys Ile Ser Arg Arg Phe Leu Asn Asp Pro
385                 390                 395                 400

Gln Ala Phe Asn Glu Ala Phe Ala Arg Ala Trp Phe Lys Leu Thr His
            405                 410                 415

Arg Asp Met Gly Pro Lys Ala Arg Tyr Ile Gly Pro Glu Val Pro Lys
            420                 425                 430

Glu Asp Leu Ile Trp Gln Asp Pro Leu Pro Gln Pro Leu Tyr Gln Pro
            435                 440                 445
```

```
Thr Gln Glu Asp Ile Ile Asn Leu Lys Ala Ala Ile Ala Ala Ser Gly
    450                 455                 460

Leu Ser Ile Ser Glu Met Val Ser Val Ala Trp Ala Ser Ala Ser Thr
465                 470                 475                 480

Phe Arg Gly Gly Asp Lys Arg Gly Gly Ala Asn Gly Ala Arg Leu Ala
                485                 490                 495

Leu Ala Pro Gln Arg Asp Trp Asp Val Asn Ala Val Ala Ala Arg Val
            500                 505                 510

Leu Pro Val Leu Glu Glu Ile Gln Lys Thr Thr Asn Lys Ala Ser Leu
        515                 520                 525

Ala Asp Ile Ile Val Leu Ala Gly Val Val Gly Ile Glu Gln Ala Ala
    530                 535                 540

Ala Ala Ala Arg Val Ser Ile His Val Pro Phe Pro Pro Gly Arg Val
545                 550                 555                 560

Asp Ala Arg His Asp Gln Thr Asp Ile Glu Met Phe Ser Leu Leu Glu
                565                 570                 575

Pro Ile Ala Asp Gly Phe Arg Asn Tyr Arg Ala Arg Leu Asp Val Ser
            580                 585                 590

Thr Thr Glu Ser Leu Leu Ile Asp Lys Ala Gln Gln Leu Thr Leu Thr
        595                 600                 605

Ala Pro Glu Met Thr Val Leu Val Gly Gly Met Arg Val Leu Gly Thr
    610                 615                 620

Asn Phe Asp Gly Ser Gln Asn Gly Val Phe Thr Asp Lys Pro Gly Val
625                 630                 635                 640

Leu Ser Thr Asp Phe Phe Ala Asn Leu Leu Asp Met Arg Tyr Glu Trp
                645                 650                 655

Lys Pro Thr Asp Asp Ala Asn Glu Leu Phe Glu Gly Arg Asp Arg Leu
            660                 665                 670

Thr Gly Glu Val Lys Tyr Thr Ala Thr Arg Ala Asp Leu Val Phe Gly
        675                 680                 685

Ser Asn Ser Val Leu Arg Ala Leu Ala Glu Val Tyr Ala Cys Ser Asp
    690                 695                 700

Ala His Glu Lys Phe Val Lys Asp Phe Val Ala Ala Trp Val Lys Val
705                 710                 715                 720

Met Asn Leu Asp Arg Phe Asp Leu Gln
                725

(2) INFORMATION FOR SEQ ID NO:51:

(i) SEQUENCE CHARACTERISTICS:
        (A) LENGTH: 731 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

Met Glu Asn Gln Asn Arg Gln Asn Ala Ala Gln Cys Pro Phe His Glu
1                   5                   10                  15

Ser Val Thr Asn Gln Ser Ser Asn Arg Thr Thr Asn Lys Asp Trp Trp
                20                  25                  30

Pro Asn Gln Leu Asn Leu Ser Ile Leu His Gln His Asp Arg Lys Thr
            35                  40                  45

Asn Pro His Asp Glu Glu Phe Asn Tyr Ala Glu Glu Phe Gln Lys Leu
        50                  55                  60
```

```
Asp Tyr Trp Ala Leu Lys Glu Asp Leu Arg Lys Leu Met Thr Glu Ser
 65                  70                  75                  80

Gln Asp Trp Trp Pro Ala Asp Tyr Gly His Tyr Gly Pro Leu Phe Ile
             85                  90                  95

Arg Met Ala Trp His Ser Ala Gly Thr Tyr Arg Ile Gly Asp Gly Arg
            100                 105                 110

Gly Gly Ala Ser Thr Gly Thr Gln Arg Phe Ala Pro Leu Asn Ser Trp
            115                 120                 125

Pro Asp Asn Ala Asn Leu Asp Lys Ala Arg Arg Cys Tyr Gly Arg Ser
            130                 135                 140

Lys Arg Asn Thr Gly Thr Lys Ser Leu Gly Pro Ile Cys Ser Phe Trp
145                 150                 155                 160

Arg Ala Met Ser Leu Leu Asn Arg Trp Val Glu Lys Arg Leu Asp Ser
                165                 170                 175

Ala Ala Gly Pro Leu Thr Ser Gly Ile Arg Lys Lys Thr Phe Ile Gly
            180                 185                 190

Asp Arg Lys Lys Ser Gly Ser Pro Leu Asn Ala Ile Pro Val Ile Ala
            195                 200                 205

Ser Ser Lys Thr Arg Ser Pro Arg Ala Asn Gly Val Asn Leu Arg Gln
            210                 215                 220

Pro Arg Arg Ala Gly Arg Gln Ala Gly Ser Lys Ser Arg Gly Ile Ser
225                 230                 235                 240

Ala Glu Thr Phe Arg Arg Met Gly Met Asn Asp Glu Glu Thr Val Ala
                245                 250                 255

Leu Ile Ala Gly Gly His Thr Phe Gly Lys Ala His Arg Gly Gly Pro
            260                 265                 270

Ala Thr His Val Gly Pro Glu Pro Glu Ala Ala Pro Ile Glu Ala Gln
            275                 280                 285

Gly Leu Gly Trp Ile Ser Ser Tyr Gly Lys Gly Lys Gly Ser Asp Thr
            290                 295                 300

Ile Thr Ser Gly Ile Glu Gly Ala Trp Thr Pro Thr Pro Thr Gln Trp
305                 310                 315                 320

Asp Thr Ser Tyr Phe Asp Met Leu Phe Gly Tyr Asp Trp Trp Leu Thr
                325                 330                 335

Lys Ser Pro Ala Gly Ala Trp Gln Trp Met Ala Val Asp Pro Asp Glu
            340                 345                 350

Lys Asp Leu Ala Pro Asp Ala Glu Asp Pro Ser Lys Lys Val Pro Thr
            355                 360                 365

Met Met Met Thr Thr Asp Leu Ala Leu Arg Phe Asp Pro Glu Tyr Glu
            370                 375                 380

Lys Ile Ala Arg Arg Phe His Gln Asn Pro Glu Glu Phe Ala Glu Ala
385                 390                 395                 400

Phe Ala Arg Ala Trp Phe Lys Leu Thr His Arg Asp Met Gly Pro Lys
                405                 410                 415

Thr Arg Tyr Leu Gly Pro Glu Val Pro Lys Glu Asp Phe Ile Trp Gln
            420                 425                 430

Asp Pro Ile Pro Glu Val Asp Tyr Glu Leu Thr Glu Ala Glu Ile Glu
            435                 440                 445

Glu Ile Lys Ala Lys Ile Leu Asn Ser Gly Leu Thr Val Ser Glu Leu
            450                 455                 460

Val Lys Thr Ala Trp Ala Ser Ala Ala Arg Ser Ala Thr Arg Ile Ser
465                 470                 475                 480

Ala Ala Thr Asn Gly Arg Arg Ile Arg Leu Ala Pro Gln Lys Asp Trp
```

-continued

```
                485                 490                 495
Glu Val Asn Glu Pro Glu Arg Leu Ala Lys Val Leu Ser Val Leu Arg
                500                 505                 510

Gly His Pro Ala Arg Thr Ala Glu Lys Ser Lys His Arg Arg Leu Asp
            515                 520                 525

Arg Leu Gly Gly Thr Leu Arg Trp Lys Arg Gln Pro Ala Thr Pro Ala
        530                 535                 540

Leu Met Ser Lys Cys His Phe Ser Leu Ala Ala Ala Met Arg His Lys
545                 550                 555                 560

Ser Lys Pro Met Ser Lys Ala Leu Pro Cys Trp Asn Arg Ser Gln Met
                565                 570                 575

Ala Ser Ala Thr Ile Lys Ser Lys Ser Thr Arg Phe Arg Arg Lys Ser
            580                 585                 590

Cys Ser Ser Thr Lys Pro Ser Ser Ser Ala Asp Arg Pro Arg Asn Asp
        595                 600                 605

Gly Leu Ser Trp Arg Phe Ala Arg Val Gly Pro Asn Tyr Arg His Leu
    610                 615                 620

Pro His Gly Val Phe Thr Asp Arg Ile Gly Val Leu Thr Asn Asp Phe
625                 630                 635                 640

Phe Val Asn Leu Leu Asp Met Asn Tyr Glu Trp Val Pro Thr Asp Ser
                645                 650                 655

Gly Ile Tyr Glu Ile Arg Asp Arg Lys Thr Gly Glu Val Arg Trp Thr
            660                 665                 670

Ala Thr Arg Val Asp Leu Ile Phe Gly Ser Asn Ser Ile Leu Arg Ser
        675                 680                 685

Tyr Ala Glu Phe Tyr Ala Gln Asp Asp Asn Gln Glu Lys Phe Val Arg
    690                 695                 700

Asp Phe Ile Asn Ala Trp Val Lys Val Met Asn Ala Asp Arg Phe Asp
705                 710                 715                 720

Leu Val Lys Lys Ala Arg Glu Ser Val Thr Ala
                725                 730

(2) INFORMATION FOR SEQ ID NO:52:

(i) SEQUENCE CHARACTERISTICS:
        (A) LENGTH: 293 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

Thr Thr Pro Leu Val His Val Ala Ser Val Glu Lys Gly Arg Ser Tyr
1               5                   10                  15

Glu Asp Phe Gln Lys Val Tyr Asn Ala Ile Ala Leu Lys Leu Arg Glu
            20                  25                  30

Asp Asp Glu Tyr Asp Asn Tyr Ile Gly Tyr Gly Pro Val Leu Val Arg
        35                  40                  45

Leu Ala Trp His Ile Ser Gly Thr Trp Asp Lys His Asp Asn Thr Gly
    50                  55                  60

Gly Ser Tyr Gly Gly Thr Tyr Arg Phe Lys Lys Glu Phe Asn Asp Pro
65                  70                  75                  80

Ser Asn Ala Gly Leu Gln Asn Gly Phe Lys Phe Leu Glu Pro Ile His
            85                  90                  95

Lys Glu Phe Pro Trp Ile Ser Ser Gly Asp Leu Phe Ser Leu Gly Gly
```

-continued

```
                100                 105                 110
Val Thr Ala Val Glu Met Gln Gly Pro Lys Ile Pro Trp Arg Cys Gly
            115                 120                 125
Arg Val Asp Thr Pro Glu Asp Thr Thr Pro Asp Asn Gly Arg Leu Pro
130                 135                 140
Asp Ala Asp Lys Asp Ala Gly Tyr Val Arg Thr Phe Phe Gln Arg Leu
145                 150                 155                 160
Asn Met Asn Asp Arg Glu Val Val Ala Leu Met Gly Ala His Ala Leu
                165                 170                 175
Gly Lys Thr His Leu Lys Asn Ser Gly Tyr Glu Gly Pro Trp Gly Ala
            180                 185                 190
Ala Asn Asn Val Phe Thr Asn Glu Phe Tyr Leu Asn Leu Leu Asn Glu
            195                 200                 205
Asp Trp Lys Leu Glu Lys Asn Asp Ala Asn Asn Glu Gln Trp Asp Ser
    210                 215                 220
Lys Ser Gly Tyr Met Met Leu Pro Thr Asp Tyr Ser Leu Ile Gln Asp
225                 230                 235                 240
Pro Lys Tyr Leu Ser Ile Val Lys Glu Tyr Ala Asn Asp Gln Asp Lys
                245                 250                 255
Phe Phe Lys Asp Phe Ser Lys Ala Phe Glu Lys Leu Leu Glu Asn Gly
            260                 265                 270
Ile Thr Phe Pro Lys Asp Ala Pro Ser Pro Phe Ile Phe Lys Thr Leu
            275                 280                 285
Glu Glu Gln Gly Leu
        290
```

(2) INFORMATION FOR SEQ ID NO:53:

(i) SEQUENCE CHARACTERISTICS:
        (A) LENGTH: 652 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Met Ser Thr Asp Asp Thr His Asn Thr Thr Lys Cys Pro Phe His Gln
1               5                   10                  15
Gly Gly His Asp Gln Ser Ala Gly Ala Gly Thr Thr Asn Arg Asp Trp
                20                  25                  30
Trp Pro Asn Gln Leu Asp Leu Leu His Gln His Ser Asn Arg Ser Asn
            35                  40                  45
Pro Leu Gly Glu Asp Phe Asp Tyr Lys Glu Phe Ser Lys Leu Asp Tyr
    50                  55                  60
Tyr Ala Leu Lys Asp Leu Lys Ala Leu Leu Thr Glu Ser Gln Pro Trp
65                  70                  75                  80
Trp Pro Ala Asp Tyr Gly Tyr Gly Pro Leu Phe Ile Arg Met Ala Trp
                85                  90                  95
His Gly Ala Gly Thr Tyr Arg Asp Gly Arg Gly Ala Gly Gly Gln
                100                 105                 110
Arg Phe Ala Pro Leu Asn Ser Trp Pro Asp Asn Ala Ser Leu Asp Lys
            115                 120                 125
Ala Arg Arg Leu Leu Trp Pro Ile Lys Lys Tyr Gly Gln Lys Ile Ser
            130                 135                 140
Trp Ala Asp Leu Phe Ile Leu Ala Gly Asn Val Ala Leu Glu Asn Phe
```

-continued

```
            145                 150                 155                 160
      Arg Gly Phe Ala Gly Arg Thr Glu Asp Val Trp Glu Pro Asp Leu Asp
                      165                 170                 175
      Val Asn Trp Gly Glu Lys Ala Trp Leu Thr His Arg His Pro Glu Leu
                      180                 185                 190
      Ala Lys Ala Pro Leu Gly Ala Thr Glu Met Gly Leu Ile Tyr Val Asn
                      195                 200                 205
      Pro Glu Gly Pro Asn His Ser Pro Leu Ser Ala Ala Ala Ile Arg
          210                 215                 220
      Thr Phe Arg Met Gly Met Asn Asp Glu Glu Thr Val Ala Leu Ile Ala
      225                 230                 235                 240
      Gly Gly His Thr Leu Gly Lys Thr His Gly Ala Gly Pro Ala Ser His
                      245                 250                 255
      Val Gly Pro Pro Glu Ala Ala Pro Ile Glu Ala Gln Gly Leu Gly Trp
                      260                 265                 270
      Ala Ser Ser Tyr Gly Ser Gly Val Gly Ala Asp Ala Ile Thr Ser Gly
                      275                 280                 285
      Glu Val Val Trp Thr Gln Thr Pro Thr Gln Trp Asn Phe Phe Glu Asn
          290                 295                 300
      Leu Phe Tyr Glu Trp Val Leu Thr Lys Ser Pro Ala Gly Ala Gln Glu
      305                 310                 315                 320
      Ala Val Asp Gly Ala Pro Asp Ile Ile Pro Asp Pro Phe Asp Pro Ser
                      325                 330                 335
      Lys Lys Arg Lys Pro Thr Met Leu Val Thr Asp Leu Leu Arg Phe Asp
                      340                 345                 350
      Pro Glu Tyr Glu Lys Ile Ser Arg Arg Phe Leu Asn Asp Pro Glu Phe
                      355                 360                 365
      Glu Ala Phe Ala Arg Ala Trp Phe Lys Leu Thr His Arg Asp Met Gly
          370                 375                 380
      Pro Lys Arg Tyr Ile Gly Pro Glu Val Pro Lys Glu Asp Leu Ile Trp
      385                 390                 395                 400
      Gln Asp Pro Pro Gln Tyr Pro Thr Glu Asp Ile Ile Leu Lys Ala Ala
                      405                 410                 415
      Ile Ala Ala Ser Gly Leu Val Ser Glu Leu Val Ser Ala Trp Ala Ser
                      420                 425                 430
      Ala Ser Thr Phe Arg Gly Gly Asp Lys Arg Gly Gly Ala Asn Gly Ala
                      435                 440                 445
      Arg Leu Ala Pro Gln Arg Asp Trp Val Asn Pro Ala Ala Arg Val Leu
          450                 455                 460
      Val Leu Glu Glu Ile Gln Thr Lys Ala Ser Leu Ala Asp Ile Val Leu
      465                 470                 475                 480
      Gly Val Val Gly Glu Lys Ala Ala Ala Ala Gly Leu Ser Ile His
                      485                 490                 495
      Val Pro Phe Ala Pro Gly Arg Asp Ala Arg Gln Asp Gln Thr Asp Ile
                      500                 505                 510
      Glu Met Phe Leu Leu Glu Pro Ile Ala Asp Gly Phe Arg Asn Tyr Arg
                      515                 520                 525
      Ala Leu Asp Val Ser Thr Thr Glu Ser Leu Ile Asp Lys Ala Gln Gln
          530                 535                 540
      Leu Thr Leu Ala Pro Glu Met Thr Val Leu Val Gly Gly Met Arg Val
      545                 550                 555                 560
      Leu Gly Asn Asp Gly Pro Asn Gly Val Phe Thr Asp Arg Gly Val Leu
                      565                 570                 575
```

```
Asn Asp Phe Phe Val Asn Leu Leu Asp Met Arg Tyr Glu Trp Lys Pro
            580                 585                 590

Thr Asp Leu Glu Gly Arg Asp Arg Thr Gly Glu Val Lys Trp Thr Ala
            595                 600                 605

Arg Asp Leu Val Phe Gly Ser Asn Ser Val Leu Arg Ala Leu Ala Glu
            610                 615                 620

Val Tyr Ala Ser Asp Ala Glu Lys Phe Val Lys Asp Phe Val Ala Ala
625                 630                 635                 640

Trp Val Lys Val Met Asn Leu Asp Arg Phe Asp Leu
                645                 650
```

(2) INFORMATION FOR SEQ ID NO:54:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
CAGTTCATGG ATCAGAACAA CCCTCTGTCG GGCCTGACCC ACAAGCGCCG GCTGTCG        57
```

(2) INFORMATION FOR SEQ ID NO:55:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Phe Phe Gly Ser Ser Gln Leu Ser Gln Phe Met Asp Gln Asn Asn Pro
1               5                   10                  15

Leu Ser Glu Ile Thr His Lys Arg Arg Ile Ser Ala Leu Gly Pro Gly
            20                  25                  30

Gly
```

(2) INFORMATION FOR SEQ ID NO:56:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

```
Phe Phe Gly Thr Ser Gln Leu Ser Gln Phe Met Asp Gln Asn Asn Pro
1               5                   10                  15

Leu Ser Gly Leu Thr His Lys Arg Arg Leu Ser Ala Leu Gly Pro Gly
            20                  25                  30

Gly
```

(2) INFORMATION FOR SEQ ID NO:57:

(i) SEQUENCE CHARACTERISTICS:
        (A) LENGTH: 3447 base pairs
        (B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:57:

| | | | | | |
|---|---|---|---|---|---|
| GTGCCCGGCG | CGCCCAACCG | AATTTCATTT | GCCAAGCTCC | GCGAACCGCT | TGAGGTTCCG | 60 |
| GGGCTACTTG | ATGTGCAGAC | TGATTCATTT | GAGTGGTTGA | TCGGATCGCC | GTGCTGGCGT | 120 |
| GCAGCGGCCG | CAAGCCGCGG | CGATCTCAAG | CCGGTGGGTG | GTCTCGAAGA | GGTGCTCTAC | 180 |
| GAGCTGTCGC | CGATCGAGGA | TTTCTCCGGC | TCAATGTCAT | TGTCTTTCTC | CGATCCCCGT | 240 |
| TTTGACGAAG | TCAAGGCGCC | CGTCGAAGAG | TGCAAAGACA | AGGACATGAC | GTACGCGGCC | 300 |
| CCGCTGTTCG | TCACGGCCGA | GTTCATCAAC | AACAACACCG | GGGAGATCAA | GAGCCAGACG | 360 |
| GTGTTTATGG | GCGACTTCCC | TATGATGACT | GAGAAGGGAA | CCTTCATCAT | CAACGGGACC | 420 |
| GAGCGTGTCG | TCGTTAGCCA | GCTGGTGCGC | TCCCCTGGAA | TATACTTCGA | CGAGACGATC | 480 |
| GACAAGTCCA | CAGAAAAGAC | GCTGCATAGT | GTCAAGGTGA | TTCCCAGCCG | CGGTGCCTGG | 540 |
| TTGGAATTCG | ATGTCGATAA | ACGCGACACC | GTCGGTGTCC | GCATTGACCG | GAAGCGCCGG | 600 |
| CAACCCGTCA | CGGTGCTTCT | CAAAGCGCTA | GGTTGGACCA | GTGAGCAGAT | CACCGAGCGT | 660 |
| TTCGGTTTCT | CCGAGATCAT | GCGCTCGACG | CTGGAGAAGG | ACAACACAGT | TGGCACCGAC | 720 |
| GAGGCGCTGC | TAGACATCTA | TCGTAAGTTG | CGCCCAGGTG | AGCCGCCGAC | TAAGGAGTCC | 780 |
| GCGCAGACGC | TGTTGGAGAA | CCTGTTCTTC | AAGGAGAAAC | GCTACGACCT | GGCCAGGGTT | 840 |
| GGTCGTTACA | AGGTCAACAA | GAAGCTCGGG | TTGCACGCCG | GTGAGTTGAT | CACGTCGTCC | 900 |
| ACGCTGACCG | AAGAGGATGT | CGTCGCCACC | ATAGAGTACC | TGGTTCGTCT | GCATGAGGGT | 960 |
| CAGTCGACAA | TGACTGTCCC | AGGTGGGGTA | GAAGTGCCAG | TGGAAACTGA | CGATATCGAC | 1020 |
| CACTTCGGCA | ACCGCCGGCT | GCGCACGGTC | GGCGAATTGA | TCCAGAACCA | GATCCGGGTC | 1080 |
| GGTATGTCGC | GGATGGAGCG | GGTGGTCCGG | GAGCGGATGA | CCACCCAGGA | CGTCGAGGCG | 1140 |
| ATCACGCCGC | AGACGCTGAT | CAATATCCGT | CCGGTGGTCG | CCGCTATCAA | GGAATTCTTC | 1200 |
| GGCACCAGCC | AGCTGTCGCA | GTTCATGGAT | CAGAACAACC | CTCTGTCGGG | CCTGACCCAC | 1260 |
| AAGCGCCGGC | TGTCGGCGCT | GGGCCCGGGT | GGTTTGTCGC | GTGAGCGTGC | CGGGCTAGAG | 1320 |
| GTCCGTGACG | TGCACCCTTC | GCACTACGGC | CGGATGTGCC | CGATCGAGAC | TCCGGAGGGC | 1380 |
| CCGAACATAG | GTCTGATCGG | TTCATTGTCG | GTGTACGCGC | GGGTCAACCC | CTTCGGGTTC | 1440 |
| ATCGAAACAC | CGTACCGCAA | AGTGGTTGAC | GGTGTGGTCA | GCGACGAGAT | CGAATACTTG | 1500 |
| ACCGCTGACG | AGGAAGACCG | CCATGTCGTG | GCGCAGGCCA | ACTCGCCGAT | CGACGAGGCC | 1560 |
| GGCCGTTCCT | CGAGCCGCGC | GTGTTGGGTG | CGCCGCAAGG | CGGGCGAGGT | GGAGTACGTG | 1620 |
| GCCTCGTCCG | AGGTGGATTA | CATGGATGTC | TCGCCACGCC | AGATGGTGTC | GGTGGCCACA | 1680 |
| GCGATGATTC | CGTTCCTTGA | GCACGACGAC | GCCAACCGTG | CCCTGATGGG | CGCTAACATG | 1740 |
| CAGCGCCAAG | CGGTTCCGTT | GGTGCGCAGC | GAACGACCGT | TGGTGGGTAC | CGGTATGGAG | 1800 |
| TTGCGCGCGG | CCATCGACGC | TGGCCACGTC | GTCGTTGCGG | AGAAGTCCGG | GGTGATCGAG | 1860 |
| GAGGTTTCCG | CCGACTACAT | CACCGTGATG | GCCGATGACG | GCACCCGGCG | GACTTATCGG | 1920 |
| ATGCGTAAGT | TCGCGCGCTC | CAACCACGGC | ACCTGCGCCA | ACCAGTCCCC | GATCGTGGAT | 1980 |
| GCGGGGGATC | GGGTCGAGGC | CGGCCAAGTG | ATTGCTGACG | GTCCGTGCAC | TGAGAACGGC | 2040 |
| GAGATGGCGT | TGGGCAAGAA | CTTGCTGGTG | GCGATCAATG | CCGTGGGAGG | GTCAACAACT | 2100 |
| AACGAGGATG | CGATCATCCT | GTCTAACCGA | CTGGTCGAAG | AGGACGTGCT | TACTTCGATT | 2160 |

```
CACATTGAGG AGCATGAGAT CGACGCCCGT GACACCAAGC TGGGTGCTGA GGAGATCACC       2220

CGGGACATTC CCAACGTCTC CGATGAGGTG CTAGCCGACT TGGACGAGCG GGGCATCGTG       2280

CGGATTGGCG CGGAGGTTCG TGACGGTGAT ATCCTGGTTG CAAGGTCAC CCCGAAGGGG        2340

GAAACTGAGC TGACACCGGA AGAGCGGTTG CTGCGGGCGA TCTTCGGCGA AAAGGCCCGC       2400

GAGGTCCGTG ACACGTCGCT GAAGGTGCCA CACGGCGAAT CCGGCAAGGT GATCGGCATT      2460

CGGGTGTTCT CCCATGAGGA TGACGACGAG CTGCCCGCCG GCGTCAACGA GCTGGTCCGT      2520

GTCTACGTAG CCCAGAAGCG CAAGATCTCT GACGGTGACA AGCTGGCTGG GCGGCACGGC      2580

AACAAGGGCG TGATCGGCAA GATCCTGCCT GCCGAGGATA TGCCGTTTCT GCCAGACGGC      2640

ACCCCGGTGG ACATCATCCT CAACACTCAC GGGGTGCCGC GGCGGATGAA CGTCGGTCAG      2700

ATCTTGGAAA CCCACCTTGG GTGGGTAGCC AAGTCCGGCT GGAAGATCGA CGTGGCCGGC      2760

GGTATACCGG ATTGGGCGGT CAACTTGCCT GAGGAGTTGT TGCACGCTGC GCCCAACCAG      2820

ATCGTGTCGA CCCCGGTGTT CGACGGCGCC AAGGAAGAGG AACTACAGGG CCTGTTGTCC      2880

TCCACGTTGC CCAACCGCGA CGGCGATGTG ATGGTGGGCG GCGACGGCAA GGCGGTGCTC      2940

TTCGATGGGC GCAGCGGTGA GCCGTTCCCT TATCCGGTGA CGGTTGGCTA CATGTACATC      3000

ATGAAGCTGC ACCACTTGGT GGACGACAAG ATCCACGCCC GCTCCACCGG CCCGTACTCG      3060

ATGATTACCC AGCAGCCGTT GGGTGGTAAG GCACAGTTCG GTGGCCAGCG ATTCGGTGAG      3120

ATGGAGTGCT GGGCCATGCA GGCCTACGGT GCGGCCTACA CGCTGCAGGA GCTGTTGACC      3180

ATCAAGTCCG ACGACACCGT CGGTCGGGTC AAGGTTTACG AGGCTATCGT TAAGGGTGAG      3240

AACATCCCCG AGCCGGGCAT CCCCGAGTCG TTCAAGGTGC TGCTCAAGGA GTTACAGTCG      3300

CTGTGTCTCA ACGTCGAGGT GCTGTCGTCC GACGGTGCGG CGATCGAGTT GCGCGAAGGT      3360

GAGGATGAGG ACCTCGAGCG GGCTGCGGCC AACCTCGGTA TCAACTTGTC CCGCAACGAA      3420

TCGGCGTCCA TAGAAGATCT GGCTTAG                                         3447
```

(2) INFORMATION FOR SEQ ID NO:58:

(i) SEQUENCE CHARACTERISTICS:
        (A) LENGTH: 1148 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

```
Val Pro Gly Ala Pro Asn Arg Ile Ser Phe Ala Lys Leu Arg Glu Pro
1               5                   10                  15

Leu Glu Val Pro Gly Leu Leu Asp Val Gln Thr Asp Ser Phe Glu Trp
            20                  25                  30

Leu Ile Gly Ser Pro Cys Trp Arg Ala Ala Ala Ser Arg Gly Asp
        35                  40                  45

Leu Lys Pro Val Gly Gly Leu Glu Val Leu Tyr Glu Leu Ser Pro
    50                  55                  60

Ile Glu Asp Phe Ser Gly Ser Met Ser Leu Ser Phe Ser Asp Pro Arg
65              70                  75                  80

Phe Asp Glu Val Lys Ala Pro Val Glu Glu Cys Lys Asp Lys Asp Met
                85                  90                  95

Thr Tyr Ala Ala Pro Leu Phe Val Thr Ala Glu Phe Ile Asn Asn Asn
            100                 105                 110

Thr Gly Glu Ile Lys Ser Gln Thr Val Phe Met Gly Asp Phe Pro Met
```

```
                    115                 120                 125
Met Thr Glu Lys Gly Thr Phe Ile Ile Asn Gly Thr Glu Arg Val Val
130                 135                 140

Val Ser Gln Leu Val Arg Ser Pro Gly Val Tyr Phe Asp Glu Thr Ile
145                 150                 155                 160

Asp Lys Ser Thr Glu Lys Thr Leu His Ser Val Lys Val Ile Pro Ser
                    165                 170                 175

Arg Gly Ala Trp Leu Glu Phe Asp Val Asp Lys Arg Asp Thr Val Gly
                    180                 185                 190

Val Arg Ile Asp Arg Lys Arg Gln Pro Val Thr Val Leu Leu Lys
                195                 200                 205

Ala Leu Gly Trp Thr Ser Glu Gln Ile Thr Glu Arg Phe Gly Phe Ser
210                 215                 220

Glu Ile Met Arg Ser Thr Leu Glu Lys Asp Asn Thr Val Gly Thr Asp
225                 230                 235                 240

Glu Ala Leu Leu Asp Ile Tyr Arg Lys Leu Arg Pro Gly Glu Pro Pro
                245                 250                 255

Thr Lys Glu Ser Ala Gln Thr Leu Leu Glu Asn Leu Phe Phe Lys Glu
                260                 265                 270

Lys Arg Tyr Asp Leu Ala Arg Val Gly Arg Tyr Lys Val Asn Lys Lys
            275                 280                 285

Leu Gly Leu His Ala Gly Glu Leu Ile Thr Ser Thr Leu Thr Glu
            290                 295                 300

Glu Asp Val Val Ala Thr Ile Glu Tyr Leu Val Arg Leu His Glu Gly
305                 310                 315                 320

Gln Ser Thr Met Thr Val Pro Gly Gly Val Glu Val Pro Val Glu Thr
                325                 330                 335

Asp Asp Ile Asp His Phe Gly Asn Arg Arg Leu Arg Thr Val Gly Glu
                340                 345                 350

Leu Ile Gln Asn Gln Ile Arg Val Gly Met Ser Arg Met Glu Arg Val
            355                 360                 365

Val Arg Glu Arg Met Thr Thr Gln Asp Val Glu Ala Ile Thr Pro Gln
            370                 375                 380

Thr Leu Ile Asn Ile Arg Pro Val Val Ala Ala Ile Lys Glu Phe Phe
385                 390                 395                 400

Gly Thr Ser Gln Leu Ser Gln Phe Met Asp Gln Asn Asn Pro Leu Ser
                405                 410                 415

Gly Leu Thr His Lys Arg Arg Leu Ser Ala Leu Gly Pro Gly Gly Leu
                420                 425                 430

Ser Arg Glu Arg Ala Gly Leu Glu Val Arg Asp Val His Pro Ser His
            435                 440                 445

Tyr Gly Arg Met Cys Pro Ile Glu Thr Pro Glu Gly Pro Asn Ile Gly
450                 455                 460

Leu Ile Gly Ser Leu Ser Val Tyr Ala Arg Val Asn Pro Phe Gly Phe
465                 470                 475                 480

Ile Glu Thr Pro Tyr Arg Lys Val Val Asp Gly Val Val Ser Asp Glu
                485                 490                 495

Ile Glu Tyr Leu Thr Ala Asp Glu Glu Asp Arg His Val Val Ala Gln
                500                 505                 510

Ala Asn Ser Pro Ile Asp Glu Ala Gly Arg Ser Ser Arg Ala Cys
            515                 520                 525

Trp Val Arg Arg Lys Ala Gly Glu Val Glu Tyr Val Ala Ser Ser Glu
530                 535                 540
```

```
Val Asp Tyr Met Asp Val Ser Pro Arg Gln Met Val Ser Val Ala Thr
545                 550                 555                 560

Ala Met Ile Pro Phe Leu Glu His Asp Asp Ala Asn Arg Ala Leu Met
            565                 570                 575

Gly Ala Asn Met Gln Arg Gln Ala Val Pro Leu Val Arg Ser Glu Arg
            580                 585                 590

Pro Leu Val Gly Thr Gly Met Glu Leu Arg Ala Ala Ile Asp Ala Gly
            595                 600                 605

His Val Val Ala Glu Lys Ser Gly Val Ile Glu Glu Val Ser Ala
610                 615                 620

Asp Tyr Ile Thr Val Met Ala Asp Asp Gly Thr Arg Arg Thr Tyr Arg
625                 630                 635                 640

Met Arg Lys Phe Ala Arg Ser Asn His Gly Thr Cys Ala Asn Gln Ser
            645                 650                 655

Pro Ile Val Asp Ala Gly Asp Arg Val Glu Ala Gly Gln Val Ile Ala
            660                 665                 670

Asp Gly Pro Cys Thr Glu Asn Gly Glu Met Ala Leu Gly Lys Asn Leu
            675                 680                 685

Leu Val Ala Ile Asn Ala Val Gly Gly Ser Thr Thr Asn Glu Asp Ala
690                 695                 700

Ile Ile Leu Ser Asn Arg Leu Val Glu Glu Asp Val Leu Thr Ser Ile
705                 710                 715                 720

His Ile Glu Glu His Glu Ile Asp Ala Arg Asp Thr Lys Leu Gly Ala
            725                 730                 735

Glu Glu Ile Thr Arg Asp Ile Pro Asn Val Ser Asp Glu Val Leu Ala
            740                 745                 750

Asp Leu Asp Glu Arg Gly Ile Val Arg Ile Gly Ala Glu Val Arg Asp
            755                 760                 765

Gly Asp Ile Leu Val Gly Lys Val Thr Pro Lys Gly Glu Thr Glu Leu
770                 775                 780

Thr Pro Glu Glu Arg Leu Leu Arg Ala Ile Phe Gly Glu Lys Ala Arg
785                 790                 795                 800

Glu Val Arg Asp Thr Ser Leu Lys Val Pro His Gly Glu Ser Gly Lys
            805                 810                 815

Val Ile Gly Ile Arg Val Phe Ser His Glu Asp Asp Glu Leu Pro
            820                 825                 830

Ala Gly Val Asn Glu Leu Val Arg Val Tyr Val Ala Gln Lys Arg Lys
            835                 840                 845

Ile Ser Asp Gly Asp Lys Leu Ala Gly Arg His Gly Asn Lys Gly Val
850                 855                 860

Ile Gly Lys Ile Leu Pro Ala Glu Asp Met Pro Phe Leu Pro Asp Gly
865                 870                 875                 880

Thr Pro Val Asp Ile Ile Leu Asn Thr His Gly Val Pro Arg Arg Met
            885                 890                 895

Asn Val Gly Gln Ile Leu Glu Thr His Leu Gly Trp Val Ala Lys Ser
            900                 905                 910

Gly Trp Lys Ile Asp Val Ala Gly Gly Ile Pro Asp Trp Ala Val Asn
            915                 920                 925

Leu Pro Glu Glu Leu Leu His Ala Ala Pro Asn Gln Ile Val Ser Thr
            930                 935                 940

Pro Val Phe Asp Gly Ala Lys Glu Glu Leu Gln Gly Leu Leu Ser
945                 950                 955                 960
```

-continued

```
Ser Thr Leu Pro Asn Arg Asp Gly Asp Val Met Val Gly Gly Asp Gly
                965                 970                 975

Lys Ala Val Leu Phe Asp Gly Arg Ser Gly Glu Pro Phe Pro Tyr Pro
            980                 985                 990

Val Thr Val Gly Tyr Met Tyr Ile Met Lys Leu His His Leu Val Asp
        995                1000                1005

Asp Lys Ile His Ala Arg Ser Thr Gly Pro Tyr Ser Met Ile Thr Gln
    1010                1015                1020

Gln Pro Leu Gly Gly Lys Ala Gln Phe Gly Gln Arg Phe Gly Glu
1025                1030                1035                1040

Met Glu Cys Trp Ala Met Gln Ala Tyr Gly Ala Ala Tyr Thr Leu Gln
               1045                1050                1055

Glu Leu Leu Thr Ile Lys Ser Asp Asp Thr Val Gly Arg Val Lys Val
           1060                1065                1070

Tyr Glu Ala Ile Val Lys Gly Glu Asn Ile Pro Glu Pro Gly Ile Pro
       1075                1080                1085

Glu Ser Phe Lys Val Leu Leu Lys Glu Leu Gln Ser Leu Cys Leu Asn
   1090                1095                1100

Val Glu Val Leu Ser Ser Asp Gly Ala Ala Ile Glu Leu Arg Glu Gly
1105                1110                1115                1120

Glu Asp Glu Asp Leu Glu Arg Ala Ala Ala Asn Leu Gly Ile Asn Leu
               1125                1130                1135

Ser Arg Asn Glu Ser Ala Ser Ile Glu Asp Leu Ala
           1140                1145
```

(2) INFORMATION FOR SEQ ID NO:59:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

```
GGCAACCGCC GCCTGCGTAC GGTCGGCGAG CTGATCCAAA ACCAGATCCG GGTCGGCATG     60

TCGCGGATGG AGCGGGTGGT CCGGGAGCGG ATGACCACCC AGGACGTGGA GGCGATCACA    120

CCGCAGACGT TGATCAACAT CCGGCCGGTG GTCGCCGCGA TCAAGGAGTT CTTCGGCACC    180

AGCCAGCTGA GCCAATTCAT GGACCAGAAC AACCCGCTGT CGGGGTTGAC GCACAAGCGC    240

CGACTGTCGG CGCTGGGGCC CGGCGGTCTG TCACGTGAGC GTGCCGGGCT GGAGGTCCGC    300

GACGTGCACC CGTCGCACTA CGGCCGGATG TGCCCGATCG AAACCCCTGA GGGGCCCAAC    360

ATCGGTCTGA TCGGCTCGCT GTCGGTGTAC GCGCGGGTCA ACCCGTTCGG GTTCATCGAA    420

ACGCCGTACC GC                                                        432
```

(2) INFORMATION FOR SEQ ID NO:60:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

```
Gly Asn Arg Arg Leu Arg Thr Val Gly Glu Leu Ile Gln Asn Gln Ile
```

```
   1               5                  10                 15
Arg Val Gly Met Ser Arg Met Glu Arg Val Val Arg Glu Arg Met Thr
                    20                 25                 30

Thr Gln Asp Val Glu Ala Ile Thr Pro Gln Thr Leu Ile Asn Ile Arg
            35                  40                 45

Pro Val Ala Ala Ile Lys Glu Phe Phe Gly Thr Ser Gln Leu Ser
 50                      55                  60

Gln Phe Met Asp Gln Asn Asn Pro Leu Ser Gly Leu Thr His Lys Arg
 65                  70                  75                  80

Arg Leu Ser Ala Leu Gly Pro Gly Gly Leu Ser Arg Glu Arg Ala Gly
                85                  90                  95

Leu Glu Val Arg Asp Val His Pro Ser His Tyr Gly Arg Met Cys Pro
                100                 105                 110

Ile Glu Thr Pro Glu Gly Pro Asn Ile Gly Leu Ile Gly Ser Leu Ser
            115                 120                 125

Val Tyr Ala Arg Val Asn Pro Phe Gly Phe Ile Glu Thr Pro Tyr Arg
            130                 135                 140
```

(2) INFORMATION FOR SEQ ID NO:61:

(i) SEQUENCE CHARACTERISTICS:
      (A) LENGTH: 462 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:61:

```
ATGCCCGATC ACAGGGCACT GCGGCAGGGA ATAATTGCAC TACGCCAACA TGTTAACAAC      60

GAACACAATT TACCTGGGAG CCGGTATATG CCCACCATTC AGCAGCTGGT ACGCAAGGGT     120

CGTCGAGACA AGATTGGCAA GGTCAAGACT GCGGCTCTGA AGGGCAACCC ACAGCGTCGC     180

GGTGTTTGCA CCCGTGTGTA CACTTCCACC CCGAAGAAGC CGAACTCGGC GCTTCGCAAG     240

GTTGCCCGCG TGAAGCTGAC GAGTCAGGTT GAGGTCACAG CGTACATACC AGGCGAGGGT     300

CACAACCTAC AGGAACACTC CATGGTGTTG GTGCGTGGTG GCCGGGTGAA AGATCTGCCT     360

GGTGTGCGTT ACAAAATCAT TCGCGGTTCG CTCGACACCC AGGGTGTCAA GAACCGGAAG     420

CAGGCTCGTA GCCGCTATGG AGCCAAGAAG GAGAAGAGCT GA                       462
```

(2) INFORMATION FOR SEQ ID NO:62:

(i) SEQUENCE CHARACTERISTICS:
      (A) LENGTH: 124 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:62:

```
Met Pro Thr Ile Gln Gln Leu Val Arg Lys Gly Arg Arg Asp Lys Ile
 1               5                  10                 15

Gly Lys Val Lys Thr Ala Ala Leu Lys Gly Asn Pro Gln Arg Arg Gly
                20                  25                  30

Val Cys Thr Arg Val Tyr Thr Ser Thr Pro Lys Lys Pro Asn Ser Ala
            35                  40                  45

Leu Arg Lys Val Ala Arg Val Lys Leu Thr Ser Gln Val Glu Val Thr
 50                  55                  60
```

```
Ala Tyr Ile Pro Gly Glu Gly His Asn Leu Gln Glu His Ser Met Val
 65                  70                  75                  80

Leu Val Arg Gly Gly Arg Val Lys Asp Leu Pro Gly Val Arg Tyr Lys
                 85                  90                  95

Ile Ile Arg Gly Ser Leu Asp Thr Gln Gly Val Lys Asn Arg Lys Gln
                100                 105                 110

Ala Arg Ser Arg Tyr Gly Ala Lys Lys Glu Lys Ser
            115                 120
```

(2) INFORMATION FOR SEQ ID NO:63:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

```
CCCACCATTC AGCAGCTGGT CCGCAAGGGT CGTCGGGACA AGATCAGTAA GGTCAAGACC      60

GCGGCTCTGA AGGGCAGCCC GCAGCGTCGT GGTGTATGCA CCCGCGTGTA CACCACCACT     120

CCGAAGAAGC CGAACTCGGC GCTTCGGAAG GTTGCCCGCG TGAAGTTGAC GAGTCAGGTC     180

GAGGTCACGG CGTACATTCC CGGCGAGGCG CACAACCTGC AGGAGCACTC GATGGTGCTG     240

GTGCGCGGCG GCCGGGTGAA GGACCTGCCT GGTGTGCGCT ACAAGATCAT TCGCGGTTCG     300

CTCGAC                                                               306
```

(2) INFORMATION FOR SEQ ID NO:64:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

```
Pro Thr Ile Gln Gln Leu Val Arg Lys Gly Arg Arg Asp Lys Ile Ser
  1               5                  10                  15

Lys Val Lys Thr Ala Ala Leu Lys Gly Ser Pro Gln Arg Arg Gly Val
                 20                  25                  30

Cys Thr Arg Val Tyr Thr Thr Thr Pro Lys Lys Pro Asn Ser Ala Leu
             35                  40                  45

Arg Lys Val Ala Arg Val Lys Leu Thr Ser Gln Val Glu Val Thr Ala
 50                  55                  60

Tyr Ile Pro Gly Glu Ala His Asn Leu Gln Glu His Ser Met Val Leu
 65                  70                  75                  80

Val Arg Gly Gly Arg Val Lys Asp Leu Pro Gly Val Arg Tyr Lys Ile
                 85                  90                  95

Ile Arg Gly Ser Leu Asp
            100
```

(2) INFORMATION FOR SEQ ID NO:65:

(i) SEQUENCE CHARACTERISTICS:
        (A) LENGTH: 264 base pairs
        (B) TYPE: nucleic acid
        (C) STRANDEDNESS: single

```
            (D) TOPOLOGY: linear (ii) MOLECULE TYPE: DNA (genomic)

(xi) SEQUENCE DESCRIPTION: SEQ ID NO:65:

CGCAAGGGTC GTCGAGACAA GATTGGCAAG GTCAAGACCG CGGCTCTGAA GGGCAGCCCG         60

CAGCGTCGTG GTGTATGCAC CCGCGTGTAC ACCACCACTC CGAAGAAGCC GAACTCGGCG        120

CTTCGGAAGG TTGCCCGCGT GAAGTTGACG AGTCAGGTCG AGGTCACGGC GTACATTCCC        180

GGCGAGGCGC ACAACCTGCA GGAGCACTCG ATGGTGCTGG TGCGCGGCGG CCGGGTGAAG        240

GACCTGCCTG GTGTGCGCTA CAAG                                              264

(2) INFORMATION FOR SEQ ID NO:66:

(i) SEQUENCE CHARACTERISTICS:
         (A) LENGTH: 88 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:66:

Arg Lys Gly Arg Arg Asp Lys Ile Gly Lys Val Lys Thr Ala Ala Leu
1               5                   10                  15

Lys Gly Asn Pro Gln Arg Arg Gly Val Cys Thr Arg Val Tyr Thr Ser
            20                  25                  30

Thr Pro Lys Lys Pro Asn Ser Ala Leu Arg Lys Val Ala Arg Val Lys
        35                  40                  45

Leu Thr Ser Gln Val Glu Val Thr Ala Tyr Ile Pro Gly Glu Gly His
    50                  55                  60

Asn Leu Gln Glu His Ser Met Val Leu Val Arg Gly Gly Arg Val Lys
65                  70                  75                  80

Asp Leu Pro Gly Val Arg Tyr Lys
                85
```

What is claimed is:

1. A process for selecting a compound that is toxic to an isoniazid-resistant mycobacterial strain, said process comprising:
   (a) incubating a catalase peroxidase enzyme with an isoniazid to produce a compound; and (b) selecting said compound that is toxic to said isoniazid-resistant mycobacterial strain.

2. The process according to claim 1, wherein said catalase peroxidase enzyme is encoded by a katG gene.

3. The process according to claim 2, wherein said katg gene is a mycobacterial gene.

4. The process according to claim 3, wherein said katG gene is a *Mycobacterium tuberculosis* gene.

5. The process according to claim 4, wherein said katg gene comprises SEQ ID NO:45.

6. The process according to claim 5, wherein said isoniazid resistant mycobacterial strain is *Mycobacterium tuberculosis.*

7. The process according to claim 6, wherein said isoniazid resistant *Mycobacterium tuberculosis* is susceptible to said compound as measured in an antibiogram assay.

8. The process according to claim 1, wherein said isoniazid-resistant mycobacterial strain is *Mycobacterium smegmatis.*

9. The process according to claim 8, wherein said *Mycobacterium smegmatis* strain is BH1.

* * * * *

UNITED STATES PATENT AND TRADEMARK OFFICE
CERTIFICATE OF CORRECTION

PATENT NO. : 6,124,098
DATED : September 26, 2000
INVENTOR(S) : Heym et al.

Page 1 of 1

It is certified that error appears in the above-identified patent and that said Letters Patent is hereby corrected as shown below:

Title page,
Item [63], "Related U.S. Application Data:,
Line 1, "No. 08/313,175", should read "No. 08/313,185, Oct. 12, 1994, --; and
Line 2, "No. PCT/EP01/01063" should read -- No. PCT/EP101063 --.

Item [57], Abstract,
Line 4, "mycobaterial" should read -- mycobacterial --;
Line 6, "susceptability" should read -- susceptibility --; and
Line 7, "mycobaterial" should read -- mycobacterial --.

Claim 3, column 91,
Line 53, "katg" should read -- katG --.

Claim 5, column 92,
Line 43, "katg" should read -- katG --.

Signed and Sealed this

Twenty-third Day of October, 2001

Attest:

*Nicholas P. Godici*

NICHOLAS P. GODICI
*Acting Director of the United States Patent and Trademark Office*

*Attesting Officer*

UNITED STATES PATENT AND TRADEMARK OFFICE
CERTIFICATE OF CORRECTION

PATENT NO.    : 6,124,098
DATED         : September 26, 2000
INVENTOR(S)   : Heym et al.

It is certified that error appears in the above-identified patent and that said Letters Patent is hereby corrected as shown below:

Title page,
Item [63], Related U.S. Application Data:
Line 2, "No. PCT/EP01/01063" should read -- No. PCT/EP93/01063

Signed and Sealed this

Fifth Day of March, 2002

Attest:

Attesting Officer

JAMES E. ROGAN
*Director of the United States Patent and Trademark Office*